United States Patent
Skardal

(10) Patent No.: US 11,629,329 B2
(45) Date of Patent: *Apr. 18, 2023

(54) BIOINK COMPOSITIONS AND METHODS OF PREPARING AND USING THE SAME

(71) Applicant: Wake Forest University Health Sciences, Winston-Salem, NC (US)

(72) Inventor: Aleksander Skardal, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 1197 days.

This patent is subject to a terminal disclaimer.

(21) Appl. No.: 16/156,535

(22) Filed: Oct. 10, 2018

(65) Prior Publication Data

US 2019/0106673 A1 Apr. 11, 2019

Related U.S. Application Data

(60) Provisional application No. 62/570,825, filed on Oct. 11, 2017.

(51) Int. Cl.
| | |
|---|---|
| *C12N 5/00* | (2006.01) |
| *A61L 27/38* | (2006.01) |
| *A61L 27/26* | (2006.01) |
| *A61L 27/52* | (2006.01) |
| *B33Y 70/00* | (2020.01) |
| *A61L 27/50* | (2006.01) |
| *A61L 27/54* | (2006.01) |

(52) U.S. Cl.
CPC .......... *C12N 5/0062* (2013.01); *A61L 27/26* (2013.01); *A61L 27/38* (2013.01); *A61L 27/50* (2013.01); *A61L 27/52* (2013.01); *A61L 27/54* (2013.01); *B33Y 70/00* (2014.12); *A61L 2300/414* (2013.01); *C12N 2513/00* (2013.01); *C12N 2533/54* (2013.01); *C12N 2533/80* (2013.01)

(58) Field of Classification Search
None
See application file for complete search history.

(56) References Cited

U.S. PATENT DOCUMENTS

| | | | |
|---|---|---|---|
| 6,020,422 | A | 2/2000 | Connors et al. |
| 6,479,198 | B2 | 11/2002 | Makino et al. |
| 8,414,739 | B2 | 4/2013 | Kimura et al. |
| 8,575,276 | B2 | 11/2013 | Lee |

(Continued)

FOREIGN PATENT DOCUMENTS

| | | |
|---|---|---|
| JP | S61225138 A | 10/1986 |
| JP | H02293735 A | 12/1990 |

(Continued)

OTHER PUBLICATIONS

Gaudet et al., Biointerphases 7: 25 (2012).*

(Continued)

*Primary Examiner* — Erin M. Bowers
(74) *Attorney, Agent, or Firm* — Myers Bigel, P.A.

(57) ABSTRACT

Described herein are bioink compositions, which may have an elastic modulus similar to a natural tissue and/or tunable mechanical properties, along with methods of preparing and using the compositions. The compositions described herein may be useful as a medium for cell and/or tissue culture and/or for bioprinting, but are not limited thereto.

20 Claims, 19 Drawing Sheets

(56) References Cited

U.S. PATENT DOCUMENTS

| | | |
|---|---|---|
| 8,658,711 B2 | 2/2014 | Shreiber et al. |
| 8,716,355 B2 | 5/2014 | Tsai |
| 10,052,350 B2 | 8/2018 | Niu et al. |
| 10,618,984 B2 | 4/2020 | Buffa et al. |
| 2003/0088885 A1 | 5/2003 | Yang et al. |
| 2007/0087435 A1 | 4/2007 | Skorecki et al. |
| 2010/0143980 A1 | 6/2010 | Balagurunathan et al. |
| 2010/0330413 A1 | 12/2010 | Gong et al. |
| 2013/0226293 A1 | 8/2013 | Venkateswaran |
| 2014/0154735 A1 | 6/2014 | Sundstrom et al. |
| 2014/0342015 A1 | 11/2014 | Murphy et al. |
| 2016/0082038 A1 | 3/2016 | Gooding et al. |
| 2016/0296477 A1 | 10/2016 | Tsai et al. |
| 2017/0107483 A1 | 4/2017 | Pendergraft et al. |
| 2017/0307598 A1 | 10/2017 | Skardal et al. |
| 2017/0312306 A1 | 11/2017 | Ranatunga et al. |
| 2018/0000743 A1 | 1/2018 | Welker et al. |
| 2018/0273904 A1 | 9/2018 | Skardal |
| 2018/0291350 A1 | 10/2018 | Murphy et al. |
| 2018/0320141 A1 | 11/2018 | Atala et al. |
| 2018/0348203 A1 | 12/2018 | Skardal |
| 2019/0187129 A1 | 6/2019 | Skardal et al. |
| 2019/0345096 A1 | 11/2019 | Welker et al. |
| 2019/0345439 A1 | 11/2019 | Skardal et al. |
| 2019/0375860 A1 | 12/2019 | Welker et al. |
| 2020/0048601 A1 | 2/2020 | Skardal et al. |
| 2020/0108172 A1 | 4/2020 | Skardal et al. |
| 2020/0376489 A1 | 12/2020 | Porada et al. |

FOREIGN PATENT DOCUMENTS

| | | | |
|---|---|---|---|
| WO | WO 2010/087912 | * | 8/2010 |
| WO | 2013180458 A1 | | 12/2013 |
| WO | 2016064648 A1 | | 4/2016 |
| WO | 2018071354 A1 | | 4/2018 |
| WO | 2018081425 | | 5/2018 |
| WO | 2019152767 A1 | | 8/2019 |

OTHER PUBLICATIONS

Ahmed, Enas M. "Hydrogel: Preparation, characterization, and applications: A review" Journal of Advanced Research, 6(2):105-121 (2015).

Au et al. "Hepatic organoids for microfluidic drug screening" Lab on a Chip, 14:3290-3299 (2014).

Bartnikowski et al. "Tailoring Hydrogel Viscoelasticity with Physical and Chemical Crosslinking" Polymers, 7(12):2650-2669 (2015).

Bell et al. "Characterization of primary human hepatocyte spheroids as a model system for drug-induced liver injury, liver function and disease" Scientific Reports, 6(25187):1-13 (2016).

Ben-Shachar et al. "The biochemistry of acetaminophen hepatotoxicity and rescue: a mathematical model" Theoretical Biology and Medical Modelling, 9(55):1-22 (2012).

Bhise et al. "A liver-on-a-chip platform with bioprinted hepatic spheroids" Biofabrication, 8(1):014101 (2016).

Brigham et al. "Mechanically Robust and Bioadhesive Collagen and Photocrosslinkable Hyaluronic Acid Semi-Interpenetrating Networks" Tissue Engineering: Part A, 15(7):1645-1653 (2009).

Briquez et al. "Extracellular Matrix-Inspired Growth Factor Delivery Systems for Skin Wound Healing" Advances in Wound Care (New Rochelle), 4(8):479-489 (2015).

Camci-Unal et al. "Synthesis and Characterization of Hybrid Hyaluronic Acid-Gelatin Hydrogels" Biomacromolecules, 14(4):1085-1092 (2013).

Castell et al. "Hepatocyte cell lines: their use, scope and limitations in drug metabolism studies" Expert Opinion on Drug Metabolism & Toxicology, 2(2):183-212 (2006).

Chia et al. "Recent advances in 3D printing of biomaterials" Journal of Biological Engineering, 9(4):1-14 (2015).

Coulouarn et al. "Hepatocyte—Stellate Cell Crosstalk in the Liver Engenders a Permissive Inflammatory Microenvironment that Drives Progression in Hepatocellular Carcinoma" Cancer Research, 72(10):2533-2542 (2012).

Delgado et al. "To Cross-Link or Not to Cross-Link? Cross-Linking Associated Foreign Body Response of Collagen-Based Devices" Tissue Engineering Part B, Reviews, 21(3):298-313 (2015).

Devarasetty et al. "Mesenchymal stem cells support growth and organization of host-liver colorectal-tumor organoids and possibly resistance to chemotherapy" Biofabrication, 9(021002):1-9 (2017).

Edmondson et al. "Three-Dimensional Cell Culture Systems and Their Applications in Drug Discovery and Cell-Based Biosensors" Assay and Drug Development Technologies, 12(4):207-218 (2014).

Ehrbar et al. "Elucidating the Role of Matrix Stiffness in 3D Cell Migration and Remodeling" Biophysical Journal, 100(2):284-293 (2011).

Esch et al. "Multi-Cellular 3D Human Primary Liver Cell Cultures Elevate Metabolic Activity Under Fluidic Flow" Lab on a Chip, 15(10):2269-2277 (2015).

Forsythe et al. "Environmental Toxin Screening Using Human-Derived 3D Bioengineered Liver and Cardiac Organoids" Frontiers in Public Health, 6(103):1-10 (2018).

Frantz et al. "The extracellular matrix at a glance" Journal of Cell Science, 123(24):4195-4200 (2010).

Gerets et al. "Characterization of primary human hepatocytes, HepG2 cells, and HepaRG cells at the mRNA level and CYP activity in response to inducers and their predictivity for the detection of human hepatotoxins" Cell Biology and Toxicology, 28(2):69-87 (2012).

Godoy et al. "Recent advances in 2D and 3D in vitro systems using primary hepatocytes, alternative hepatocyte sources and non-parenchymal liver cells and their use in investigating mechanisms of hepatotoxicity, cell signaling and ADME" Archives of Toxicology, 87(8):1315-1530 (2013).

Goldkind et al. "A systematic review of NSAIDs withdrawn from the market due to hepatotoxicity: lessons learned from the bromfenac experience" Pharmacoepidemiology & Drug Safety, 15(4):213-220 (2006).

Highley et al. "Recent advances in hyaluronic acid hydrogels for biomedical applications" Current Opinion in Biotechnology, 40:35-40 (2016).

Hospodiuk et al. "The bioink: A comprehensive review on bioprintable materials" Biotechnology Advances, 35(2):217-239 (2017).

Hughes et al. "Principles of early drug discovery" British Journal of Pharmacology, 162(6):1239-1249 (2011).

Hung et al. "Water-based polyurethane 3D printed scaffolds with controlled release function for customized cartilage tissue engineering" Biomaterials, 83:156-168 (2016).

Hynds et al. "The relevance of human stem cell-derived organoid models for epithelial translational medicine" Stem Cells, 31(3):417-422 (2013).

Jasper et al. "Evaluation of biochemical, hematological and oxidative parameters in mice exposed to the herbicide glyphosate-Roundup®" Interdisciplinary Toxicology, 5(3):133-140 (2012).

Kawelke et al. "Fibronectin Protects from Excessive Liver Fibrosis by Modulating the Availability of and Responsiveness of Stellate Cells to Active TGF-beta" PLoS One, 6(11):e28181 (2011).

Khunmanee et al. "Crosslinking method of hyaluronic-based hydrogel for biomedical applications" Journal of Tissue Engineering, 8:1-16 (2017).

Kim et al. "Prediction of drug-induced immune-mediated hepatotoxicity using hepatocyte-like cells derived from human embryonic stem cells" Toxicology, 387:1-9 (2017).

Kirk et al. "Mechanical and biocompatible characterization of a cross-linked collagen-hyaluronic acid wound dressing" Biomatter, 3(4):e25633-1-e25633-14 (2013).

Kullak-Ublick et al. "Drug-induced liver injury: recent advances in diagnosis and risk assessment" Gut, 66(6):1154-1164 (2017).

Kunz-Schughart et al. "The Use of 3-D Cultures for High-Throughput Screening: The Multicellular Spheroid Model" Journal of Biomolecular Screening, 9(4):273-285 (2004).

Lancaster et al. "Organogenesis in a dish: modeling development and disease using organoid technologies" Science, 345(6194):1247125 (2014).

Langer et al. "Tissue Engineering" Science, 260(5110):920-926 (1993).

(56) References Cited

OTHER PUBLICATIONS

Lee et al. "Engineering liver tissue spheroids with inverted colloidal crystal scaffolds" Biomaterials, 30(27):4687-4694 (2009).
Lee, William M. "Drug-induced Acute Liver Failure" Clinical Liver Disease, 17(4):1-15 (2013).
Leite et al. "Novel human hepatic organoid model enables testing of drug-induced liver fibrosis in vitro" Biomaterials, 78:1-10 (2016).
Lin et al. "Role of activated hepatic stellate cells in proliferation and metastasis of hepatocellular carcinoma" Hepatology Research, 45(3):326-336 (2015).
Liu et al. "Rapid Continuous Multi-Material Extrusion Bioprinting" Advanced Materials, 29(3):1-18 (2017).
Martinez-Hernandez et al. "The hepatic extracellular matrix. II. Ontogenesis, regeneration and cirrhosis" Virchows Archiv. A, Pathological Anatomy and Histopathology, 423(2):77-84 (1993).
Mattei et al. "On the adhesion-cohesion balance and oxygen consumption characteristics of liver organoids" PLoS One, 12(3):e0173206 (2017).
Mayoral et al. "Drug induced liver disease" Current Opinion in Gastroenterology, 15(3):208-216 (1999).
Mederacke et al. "Fate-tracing reveals hepatic stellate cells as dominant contributors to liver fibrosis independent of its etiology" Nature Communications, 4(2823):1-21 (2013).
Mederacke et al. "High-yield and high-purity isolation of hepatic stellate cells from normal and fibrotic mouse livers" Nature Protocols, 10:305-315 (2015).
Meng, Qin "Three-dimensional culture of hepatocytes for prediction of drug-induced hepatotoxicity" Expert Opinion on Drug Metabolism & Toxicology, 6(6):733-746 (2010).
Mills et al. "Physiologically Relevant Human Tissue Models for Infectious Diseases" Drug Discovery Today, 21(9):1540-1552 (2016).
Mudipalli, Anuradha "Lead hepatotoxicity & potential health effects" The Indian Journal of Medical Research, 126(6):518-527 (2007).
Munoz-Pinto et al. "Characterization of Sequential Collagen-Poly(ethylene glycol) Diacrylat Interpenetrating Networks and Initial Assessment of their Potential for Vascular Tissue Engineering" Biomaterials, 40:32-42 (2015).
Ravichandran et al. "Functionalised type-I collagen as a hydrogel building block for bio-orthogonal tissue engineering applications" Journal of Materials Chemistry B, 4:318-326 (2016).
Ruddell et al. "A Role for Serotonin (5-HT) in Hepatic Stellate Cell Function and Liver Fibrosis" The American Journal of Pathology, 169(3):861-876 (2006).
Scannell et al. "Diagnosing the decline in pharmaceutical R&D efficiency" Nature Reviews Drug Discovery, 11:191-200 (2012).
Schindelin et al. "Fiji—an Open Source platform for biological image analysis" Nature Methods, 9(7):1-15 (2012).
Sgodda et al. "A Scalable Approach for the Generation of Human Pluripotent Stem Cell-Derived Hepatic Organoids with Sensitive Hepatotoxicity Features" Stem Cells and Development, 26(20):1490-1504 (2017).
Shaw et al. "Idiosyncratic Drug-Induced Liver Injury and the Role of Inflammatory Stress with an Emphasis on an Animal Model of Trovafloxacin Hepatotoxicity" Toxicological Sciences, 118(1):7-18 (2010).
Simian et al. "Organoids: a historical perspective of thinking in three dimensions" The Journal of Cell Biology, 216(1):31-40 (2016).
Simon, Jerome B. "Acetaminophen Liver Injury" Canadian Family Physician, 31:2155-2156 (1985).
Sivakumar et al. "Exploration of Dynamic Elastic Modulus Changes on Glioblastoma Cell Populations with Aberrant EGFR Expression as a Potential Therapeutic Intervention Using a Tunable Hyaluronic Acid Hydrogel Platform" Gels, 3(3):28 (2017).
Skardal et al. "Photocrosslinkable Hyaluronan-Gelatin Hydrogels for Two-Step Bioprinting" Tissue Engineering: Part A, 16(8):2675-2685 (2010).
Skardal et al. "Tissue specific synthetic ECM hydrogels for 3-D in vitro maintenance of hepatocyte function" Biomaterials, 33(18):4565-4575 (2012).
Skardal et al. "Biomaterials for Integration with 3-D Bioprinting" Annals of Biomedical Engineering, 43(3):730-746 (2015).
Skardal et al. "A hydrogel bioink toolkit for mimicking native tissue biochemical and mechanical properties in bioprinted tissue constructs" Acta Biomaterialia, 25:24-34 (2015).
Skardal et al. "In situ patterned micro 3D liver constructs for parallel toxicology testing in a fluidic device" Biofabrication, 7(3):031001 (2015).
Skardal et al. "Liver-Tumor Hybrid Organoids for Modeling Tumor Growth and Drug Response in Vitro" 43(10):2361-2373 (2015).
Skardal et al. "A Reductionist Metastasis-on-a-Chip Platform for in Vitro Tumor Progression Modeling and Drug Screening" Biotechnology and Bioengineering, 113(9):2020-2032 (2016).
Skardal et al. "Bioprinting Cellularized Constructs Using a Tissue-specific Hydrogel Bioink" Journal of Visualized Experiments, 110:e53606 (2016).
Skardal et al. "Organoid-on-a-chip and body-on-a-chip systems for drug screening and disease modeling" Drug Discovery Today, 21(9):1399-1411 (2016).
Skardal et al. "A tunable hydrogel system for long-term release of cell-secreted cytokines and bioprinted in situ wound cell delivery" Journal of Biomedical Materials Research, 105(7):1986-2000 (2017).
Skardal et al. "Multi-tissue interactions in an integrated three-tissue organ-on-a-chip platform" Scientific Reports, 7(8837):1-16 (2017).
Soldatow et al. "In vitro models for liver toxicity testing" Toxicology Research, 2(1):23-39 (2013).
Tan et al. "Injectable, Biodegradable Hydrogels for Tissue Engineering Applications" Materials, 3:1746-1767 (2010).
Vanderburgh et al. "3D Printing of Tissue Engineered Constructs for in vitro Modeling of Disease Progression and Drug Screening" Annals of Biomedical Engineering, 45(1):164-179 (2017).
Vyas et al. "Self-Assembled Liver Organoids Recapitulate Hepatobiliary Organogenesis in Vitro" Hepatology, 67(2):750-761 (2018).
Wrzesinski et al. "The Cultural Divide: Exponential Growth in Classical 2D and Metabolic Equilibrium in 3D Environments" PLoS One, 9(9):e106973 (2014).
Xu et al. "Human hepatic stellate cell lines, LX-1 and LX-2: new tools for analysis of hepatic fibrosis" Gut, 54(1):142-151 (2005).
Yip et al. "A multicellular 3D heterospheroid model of liver tumor and stromal cells in collagen gel for anti-cancer drug testing" Biochemical and Biophysical Research Communication, 433:327-332 (2013).
Zhang et al. "Dietary luteolin attenuates chronic liver injury induced by mercuric chloride via the Nrf2/NF-kappaB/P53 signaling pathway in rats" Oncotarget, 8(25):40982-40993 (2017).
Zhang et al. "A decade of progress in liver regenerative medicine" Biomaterials, 157:161-176 (2018).
Abdel-Aziz et al. "Inhibitory activities against topoisomerase I & II by polyhydroxybenzoyl amide derivatives and their structure-activity relationship" Bioorganic & Medicinal Chemistry Letters, 14:1669-1672 (2004).
Amsden et al. "Diffusion characteristics of calcium alginate gels" Biotechnology and Bioengineering, 65(5):605-610 (1999).
Amsden, Brian "Solute Diffusion within Hydrogels. Mechanisms and Models" Macromolecules, 31:8382-8395 (1998).
Annabi et al. "Elastic sealants for surgical applications" European Journal of Pharmaceutics and Biopharmaceutics, 95(Pt. A):27-39 (2015).
Annabi et al. "Surgical Materials: Current Challenges and Nano-enabled Solutions" Nano Today, 9(5):574-589 (2014).
Augst et al. "Alginate hydrogels as biomaterials" Macromolecular Bioscience, 6(8):623-633 (2006).
Augustin et al. "Effects of microencapsulation on the gastrointestinal transit and tissue distribution of a bioactive mixture of fish oil, tributyrin and resveratrol" Journal of Functional Foods, 3(1):25-37 (2011).
Banks et al. "Synthesis of Polar Aromatic Substituted Terminal Alkynes from Propargyl Amine" Molbank, 2021:M1206 (pp. 1-6) (2021).
Barrett et al. "Mechanically Robust, Negative-Swelling, Mussel-Inspired Tissue Adhesives" Advanced Healthcare Materials, 2(5):745-755 (2013).

(56) References Cited

OTHER PUBLICATIONS

Batchelor et al. "Reduced plasma half-life of radio-labelled 25-hydroxyvitamin D3 in subjects receiving a high-fibre diet" British Journal of Nutrition, 49:213-216 (1983).
Borke et al. "Optimized triazine-mediated amidation for efficient and controlled functionalization of hyaluronic acid" Carbohydrate Polymers, 116:42-50 (2015).
Bowersock et al. "Oral vaccination of animals with antigens encapsulated in alginate microspheres" Vaccine, 17:1804-1811 (1999).
Brevitt et al. "Synthesis and in Vitro Evaluation of Two Progressive Series of Bifunctional Polyhydroxybenzamide Catechol-O-methyltransferase Inhibitors" Journal of Medicinal Chemistry, 40(13):2035-2039 (1997).
Brubaker et al. "Enzymatically Degradable Mussel-Inspired Adhesive Hydrogel" Biomacromolecules, 12:4326-4334 (2011).
Burdick et al. "Hyaluronic Acid Hydrogels for Biomedical Applications" Advanced Materials, 23(12):H41-H56 (2011).
Chen et al. "Synthesis and biological evaluation of hydroxyl-substituted Schiff-bases containing ferrocenyl moieties" Dalton Transactions, 42:15678-15686 (2013).
Cheng et al. "Antioxidant and antiproliferative activities of hydroxyl-substituted Schiff bases" Bioorganic & Medicinal Chemistry Letters, 20(8):2417-2420 (2010).
Darrabie et al. "Characteristics of Poly-L-Ornithine-coated alginate microcapsules" Biomaterials, 26(34):6846-6852 (2005).
Deidda et al. "Self-Assembled Amyloid Peptides with Arg-Gly-Asp (RGD) Motifs as Scaffolds for Tissue Engineering" ACS Biomaterials Science & Engineering, 3(7):1404-1416 (2017).
Doraiswamy et al. "Inkjet Printing of Bioadhesives" Journal of Biomedical Materials Research Part B, 89B:28-35 (2009).
Duraine et al. "Biomechanical evaluation of suture holding properties of native and tissue engineered articular cartilage" Biomechanics and Modeling in Mechanobiology, 14(1):73-81 (2015).
Elia et al. "Stimulation of In Vivo Angiogenesis by In Situ Cross-linked, Dual Growth Factor-loaded, Glycosaminoglycan Hydrogels" Biomaterials, 31(17):4630-4638 (2010).
Faion et al. "Ethyl-2-cyanoacrylate as a sealant after partial cecum resection in rattus norvegicus albinus" Journal of Brazilian College of Surgeons, 38(1):045-053 (2011).
Fairbanks et al. "Thiol-Yne Photopolymerizations: Novel Mechanism, Kinetics, and Step-Growth Formation of Highly Cross-Linked Networks" Macromolecules, 42(1):211-217 (2009).
Ferreira et al. "Development of a new photocrosslinkable biodegradable bioadhesive" International Journal of Pharmaceutics, 352(1-2):172-181 (2008).
Finbloom et al. "Cucurbit[6]uril-Promoted Click Chemistry for Protein Modification" Journal of the American Chemical Society, 139:9691-9697 (2017).
Follain et al. "Coupling of amines with polyglucuronic acid: Evidence for amide bond formation" Carbohydrate Polymers, 74:333-343 (2008).
Fu et al. "Improvement of endothelial progenitor outgrowth cell (EPOC)-mediated vascularization in gelatin-based hydrogels through pore size manipulation" Acta Biomaterialia, 58:225-237 (2017).
Galliani et al. "Aromatic Hydroxylation of Benzylamides by Potassium Superoxide" Tetrahedron, 37:2313-2317 (1981).
Sandhi et al. "Alginate-based strategies for therapeutic vascularization" Therapeutic Delivery, 4(3):327-341 (2013).
Gao et al. "FeBr3-Catalyzed Tandem Reaction of N-Propargylamides with Disulfides or Diselenides for the Synthesis of Oxazole Derivatives" Synlett, 27(7):1110-1115 (2016).
Glickman et al. "A polymeric sealant inhibits anastomotic suture hole bleeding more rapidly than gelfoam/thrombin: results of a randomized controlled trial" Archives of Surgery, 137(3):326-331 (2002).
Grinstaff, Mark W. "Designing Hydrogel Adhesives for Corneal Wound Repair" Biomaterials, 28(35):1-18 (2007).
Guo et al. "Facile Access to Multisensitive and Self-Healing Hydrogels with Reversible and Dynamic Boronic Ester and Disulfide Linkages" Biomacromolecules, 18:1356-1364 (2017).
Heida et al. "Microfluidic Fabrication of Click Chemistry-Mediated Hyaluronic Acid Microgels: A Bottom-Up Material Guide to Tailor a Microgel's Physicochemical and Mechanical Properties" Polymers, 12(1760):1-23 (2020).
Hino et al. "Transmission of symptomatic parvovirus B19 infection by fibrin sealant used during surgery" British Journal of Haematology, 108:194-195 (2000).
Jackson et al. "Fibrin sealants in surgical practice: An overview" The American Journal of Surgery, 182(2):S1-S7 (2001).
Jenkins et al. "Molecular Weight Effects upon the Adhesive Bonding of a Mussel Mimetic Polymer" ACS Applied Materials & Interfaces, 5(11):5091-5096 (2013).
Kanellos et al. "Sutureless colonic anastomosis in the rat: a randomized controlled study" Techniques in Coloproctology, 6(3):143-146 (2002).
Kawamura et al. "Frequency of Transmission of Human Parvovirus B19 Infection by Fibrin Sealant Used During Thoracic Surgery" The Annals of Thoracic Surgery, 73:1098-1100 (2002).
Kendall et al. "Immunoisolation techniques for islet cell transplantation" Expert Opinion in Biological Therapy, 2(5):503-511 (2002).
Kiviranta et al. "N,N'-Bisbenzylidenebenzene-1,4-diamines and N,N'-Bisbenzylidenenaphthalene-1,4-diamines as Sirtuin Type 2 (SIRT2) Inhibitors" Journal of Medicinal Chemistry, 49:7907-7911 (2006).
Lau, Hung "Fibrin Sealant Versus Mechanical Stapling for Mesh Fixation During Endoscopic Extraperitoneal Inguinal Hernioplasty: a Randomized Prospective Trial" Annals of Surgery, 242(5):670-675 (2005).
Lee et al. "Bio-inspired Nanoparticulate Medical Glues for Minimally Invasive Tissue Repair" Advanced Healthcare Materials, 4(16):2587-2596 (2015).
Lee et al. "Bioinspired, Calcium-Free Alginate Hydrogels with Tunable Physical and Mechanical Properties and Improved Biocompatibility" Biomacromolecules, 14(6):2004-2013 (2013).
Leggat et al. "Surgical Applications of Cyanoacrylate Adhesives: A Review of Toxicity" ANZ Journal of Surgery, 77(4):209-213 (2007).
Li et al. "Synthesis of [2]Catenanes by Template-Directed Clipping Approach" The Journal of Organic Chemistry, 77:7129-7135 (2012).
Lin et al. "Adhesion mechanisms of the mussel foot proteins mfp-1 and mfp-3" Proceedings of the National Academy of Sciences, 104(10):3782-3786 (2007).
Lin et al. "Monitoring the Long-Term Degradation Behavior of Biomimetic Bioadhesive using Wireless Magnetoelastic Senso" IEEE Transactions on Biomedical Engineering, 62(7):1838-1842 (2015).
Mandal et al. "Microencapsulation of Bacterial Cells by Emulsion Technique for Probiotic Application" Cell Microencapsulation, Chapter 22, pp. 273-279 (2016).
Mehdizadeh et al. "Injectable Citrate-Based Mussel-Inspired Tissue Bioadhesives With High Wet Strength for Sutureless Wound Closure" Biomaterials, 33(32):7972-7983 (2012).
Meng et al. "'Click' reactions in polysaccharide modification" Progress in Polymer Science, 53:52-85 (2016).
Mizrahi et al. "Elasticity and safety of alkoxyethyl cyanoacrylate tissue adhesives" Acta Biomaterialia, 7(8):3150-3157 (2011).
Montanaro et al. "Cytotoxicity, blood compatibility and antimicrobial activity of two cyanoacrylate glues for surgical use" Biomaterials, 22:59-66 (2001).
Nador et al. "Coordination polymer particles with ligand-centred pH-responses and spin transition" Chemical Communications, 50:14570-14572 (2014).
Nose et al. "A sutureless technique using cyanoacrylate adhesives when creating a stoma for extremely low birth weight infants" SpringerPlus, 5(198):1-5 (2016).
Oliva et al. "Natural Tissue Microenvironmental Conditions Modulate Adhesive Material Performance" Langmuir, 28(43):15402-15409 (2012).
Olivi et al. "Tandem amine propargylation-Sonogashira reactions: new three-component coupling leading to functionalized substituted propargylic amines" Tetrahedron Letters, 45(12):2607-2610 (2004).
Opara, Emmanuel C. "Applications of Cell Microencapsulation" Methods in Molecular Biology, 1479:23-39 (2017).
Oudshoorn et al. "Synthesis and characterization of hyperbranched polyglycerol hydrogels" Biomaterials, 27(32):5471-5479 (2006).

(56) References Cited

OTHER PUBLICATIONS

Parris et al. "N-Alkylation of Nitriles with Benzyl Alcohol, Related Alcohols, and Glycols" Journal of Organic Chemistry, 25:331-334 (1960).
Pascual et al. "Cytotoxicity of Cyanoacrylate-Based Tissue Adhesives and Short-Term Preclinical In Vivo Biocompatibility in Abdominal Hernia Repair" PLoS One, 11(6):e0157920 (2016).
Peattie et al. "Effect of Gelatin on Heparin Regulation of Cytokine Release from Hyaluronan-Based Hydrogels" Drug Delivery, 15:389-397 (2008).
Peng et al. "Novel wound sealants: biomaterials and applications" Expert Review of Medical Devices, 7(5):639-659 (2010).
Prestwich et al. "Chemically-Modified HA for Therapy and Regenerative Medicine" Current Pharmaceutical Biotechnology, 9:242-245 (2008).
Prestwich et al. "Injectable Synthetic Extracellular Matrices for Tissue Engineering and Repair" Advances in Experimental Medicine and Biology, vol. 585, Chapter 9, pp. 125-133 (2006).
Ranger et al. "Pneumostasis of experimental air leaks with a new photopolymerized synthetic tissue sealant" The American Surgeon, 63(9):788-795 (1997).
Reis et al. "Alginate Microparticles as Novel Carrier for Oral Insulin Delivery" Biotechnology and Bioengineering, 96(5):977-989 (2007).
Sanders et al. "Mechanical Characterization of a Bi-functional Tetronic Hydrogel Adhesive for Soft Tissues" Journal of Biomedical Materials Research Part A, 103(3):861-868 (2015).
Shin et al. "Tissue Adhesive Catechol-Modified Hyaluronic Acid Hydrogel for Effective, Minimally Invasive Cell Therapy" Advanced Functional Materials, 25(25):3814-3824 (2015).
Skardal et al. "Bioprinted Amniotic Fluid-Derived Stem Cells Accelerate Healing of Large Skin Wounds" Stem Cells Translational Medicine, 1(11):792-802 (2012).
Skardal et al. "Bioprinting vessel-like constructs using hyaluronan hydrogels crosslinked with tetrahedral polyethylene glycol tetraacrylates" Biomaterials, 31:6173-6181 (2010).
Skardal et al. "Dynamically Crosslinked Gold Nanoparticle—Hyaluronan Hydrogels" Advanced Materials, 22:4736-4740 (2010).
Skardal et al. "The generation of 3-D tissue models based on hyaluronan hydrogel-coated microcarriers within a rotating wall vessel bioreactor" Biomaterials, 31:8426-8435 (2010).
Smejkalova et al. "Structural Characterization of Isomeric Dimers from the Oxidative Oligomerization of Catechol with a Biomimetic Catalyst" Biomacromolecules, 8:737-743 (2007).
Spotnitz, William D. "Fibrin Sealant: The Only Approved Hemostat, Sealant, and Adhesive—a Laboratory and Clinical Perspective" ISRN Surgery, 2014(203943):1-28 (2014).
Stodola, Frank H. "A New Type of Basic Amide Hydrolysis, Characterized by Alkyl-Nitrogen Fission" The Journal of Organic Chemistry, 37(2):178-186 (1972).
Vanderhooft et al. "Rheological Properties of Cross-Linked Hyaluronan-Gelatin Hydrogels for Tissue Engineering" Macromolecular Bioscience, 9(1):20-28 (2009).
Veira et al. "Photocrosslinkable starch-based polymers for ophthalmologic drug delivery" International Journal of Biological Macromolecules, 43:325-332 (2008).
Wagner et al. "The Bioavailability of Vitamin D from Fortified Cheeses and Supplements Is Equivalent in Adults" The Journal of Nutrition, 138:1365-1371 (2008).
Wang et al. "A Temperature-Sensitive, Self-Adhesive Hydrogel to Deliver iPSC-Derived Cardiomyocytes for Heart Repair" International Journal of Cardiology, 190:177-180 (2015).
Weiss et al. "Gastrointestinal Anastomosis With Histoacryl Glue in Rats" Journal of Investigative Surgery, 14:13-19 (2001).
Wirostko et al. "Ophthalmic Uses of a Thiol-Modified Hyaluronan-Based Hydrogel" Advances in Wound Care, 3(11):708-716 (2014).
Xu et al. "Click Chemistry and Material Selection for in Situ Fabrication of Hydrogels in Tissue Engineering Applications" ACS Biomaterials Science & Engineering, 4:2276-2291 (2018).
Yang et al. "A Bio-Inspired Swellable Microneedle Adhesive for Mechanical Interlocking with Tissue" Nature Communications, 4(1702):1-23 (2013).
Zhang et al. "Engineered Extracellular Matrices with Cleavable Crosslinkers for Cell Expansion and Easy Cell Recovery" Biomaterials, 29:4521-4531 (2008).
Murphy, et al., "3D bioprinting of tissues and organs" Nature Biotechnology, 32(8):773-785 (2014).
Murphy, et al., "Evaluation of hydrogels for bio-printing applications" Journal of Biomedical Materials Research A, 101A(1):272-284 (2013).
Murphy, et al., "Solubilized Amnion Membrane Hyaluronic Acid Hydrogel Accelerates Full-Thickness Wound Healing" Stem Cells Translational Medicine, 6(11):2020-2032 (2017).
Nantasanti, et al., "Concise Review: Organoids Are a Powerful Tool for the Study of Liver Disease and Personalized Treatment Design in Humans and Animals" Stem Cells Translational Medicine, 5(3):325-330 (2016).
No, et al., "3D liver models on a microplatform: well-defined culture, engineering of liver tissue and liver-on-a-chip" Lab on a Chip, 15(19):3822-3837 (2015).
Ouyang, et al., "A Generalizable Strategy for the 3D Bioprinting of Hydrogels from Nonviscous Photo-crosslinkable Inks" Advanced Materials, 29(8):1604983 (2017).
Pampaloni, et al., "The third dimension bridges the gap between cell culture and live tissue" Nature Reviews Molecular Cell Biology, 8(10):839-845 (2007).
Poupon, et al., "[Tienilic acid-induced hepatitis associated with liver/kidney microsomal antibody (author's transl)]" La Nouvelle Presse Medicale, 9(27):1881-1884 (1980) (English translation of abstract only).
Powers, et al., "A Microfabricated Array Bioreactor for Perfused 3D Liver Culture" Biotechnology and Bioengineering, 78:257-269 (2002).
Ananthanarayanan et al. "Elucidating the mechanobiology of malignant brain tumors using a brain matrix-mimetic hyaluronic acid hydrogel platform" Biomaterials, 32(31):7913-7923 (2011).
Gill et al. "MRI-localized biopsies reveal subtype-specific differences in molecular and cellular composition at the margins of glioblastoma" Proceedings of the National Academy of Sciences USA, 111(34):12550-12555 (2014).
Lin et al. "Astrocytes protect glioma cells from chemotherapy and upregulate survival genes via gap junctional communication" Molecular Medicine Reports, 13:1329-1335 (2016).
Liu et al. "Disulfide-crosslinked hyaluronan-gelatin sponge: growth of fibrous tissue in vivo" Journal of Biomedical Materials Research Part A, 68:142-149 (2004).
Motain et al. "Heterogeneous glioblastoma cell cross-talk promotes phenotype alterations and enhanced drug resistance" Oncotarget, 6(38):40998-41017 (2015).
Patil et al. "Elucidating the cancer-specific genetic alteration spectrum of glioblastoma derived cell lines from whole exome and RNA sequencing" Oncotarget, 6(41):43452-43471 (2015).
Xu et al. "Hyaluronidase-incorporated hyaluronic acid-tyramine hydrogels for the sustained release of trastuzumab" Journal of Controlled Release, 216:47-55 (2015).

\* cited by examiner

HA-gelatin nanogels

BIOINK COMPOSITIONS AND METHODS OF PREPARING AND USING THE SAME

RELATED APPLICATION INFORMATION

This application claims the benefit of and priority to U.S. Provisional Application No. 62/570,825 filed Oct. 11, 2017, which is incorporated herein by reference in its entirety.

GOVERNMENT SUPPORT

This invention was made with government support under U.S. Army Medical Research and Materiel Command (USAMRMC) prototype Other Transaction Agreement W81XWH-15-9-0001, awarded to Advanced Technology International (ATI) as the Consortium Manager of the Medical Technology Enterprise Consortium (MTEC). The U.S. Government has certain rights in the invention.

FIELD

The present invention generally relates to bioink compositions, which may have an elastic modulus similar to a natural tissue and/or tunable mechanical properties, along with methods of preparing and using the same. The compositions described herein may be useful as a medium for cell and/or tissue culture and/or for bioprinting, but are not limited thereto.

BACKGROUND

Bioprinting has emerged as a flexible tool in regenerative medicine with potential in a variety of applications. Bioprinting is a field within biotechnology that can be described as robotic additive biofabrication that has the potential to build or pattern viable organ-like or tissue structures in three dimensions (3D). To date, a complete fully functional human-sized organ has not been printed, but this remains a goal of bioprinting research and development. However, bioprinted constructs have been implanted in animals, and small-scale bioprinted tissue constructs, or "organoids", are currently being implemented in a number of applications, including pathology modeling, drug development, toxicology screening, and personalized medicine in cancer.

One of the major problems that the field of bioprinting, and more broadly biomanufacturing, currently faces is the lack of materials that are designed specifically for use in bioprinting. Much work has focused on adapting more traditional materials to bioprinting processes and hardware. As a result, there is a need for bioprintable biomaterials that are simple to implement in a wide variety of bioprinter hardware platforms.

SUMMARY

A first aspect of the present invention is directed to a composition including thiolated hyaluronic acid, methacrylated collagen (e.g., methacrylated Type 1 collagen), and water.

Another aspect of the present invention is directed to a method of making a hydrogel and/or an organoid, the method including providing a composition comprising thiolated hyaluronic acid and methacrylated collagen (e.g., methacrylated Type 1 collagen) at a pH of about 6.5 or 7 to about 7.5 or 8, optionally wherein the composition comprises one or more live cell(s), to provide a hyaluronic acid-collagen hydrogel.

Also described herein is the use of a composition and/or method of the present invention for bioprinting (e.g., bioprinting a cellular construct) and/or preparing an organoid.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EXAMPLE EMBODIMENTS

Figure 1:
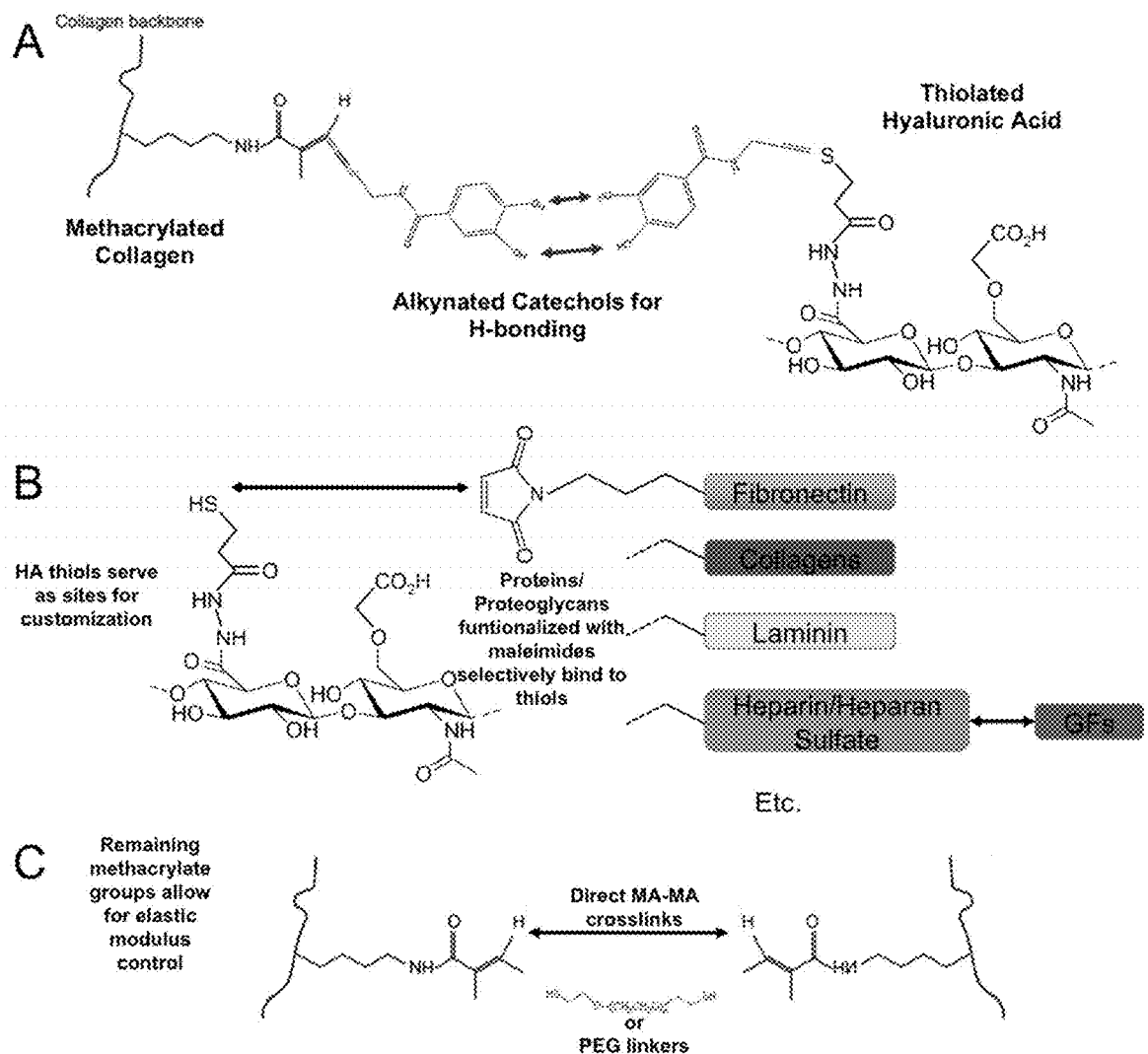
FIG. 1 shows an example strategy for incorporating in a composition of the present invention A) thixotropy via non-permanent bonds such as hydrogen bonds or electrostatic interactions, B) customization of adhesion proteins and growth factors, and/or C) final elastic modulus control by crosslinking remaining methacrylate groups.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

As used herein, the terms "increase," "increases," "increased," "increasing," and similar terms indicate an elevation in the specified parameter of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

"Cells" and "cell" as used in the present invention are, in general, animal cells, particularly mammalian and primate cells, examples of which include but are not limited to human, dog, cat, rabbit, monkey, chimpanzee, cow, pig, goat. The cells may be differentiated at least in part to a particular cell or tissue type, such as liver, intestine, pancreas, lymph node, smooth muscle, skeletal muscle, central nerve, peripheral nerve, skin, immune system, etc. Some cells may be cancer cells, as discussed further below, in which case they optionally may express (naturally, or by recombinant techniques) a detectable compound, as also discussed further below.

"Three dimensional tissue construct" and "organoid" are used interchangeably herein and, as used herein, refer to a composition of live cells, typically in a carrier media, arranged in a three-dimensional or multi-layered configuration (as opposed to a monolayer). Suitable carrier media include compositions of the present invention (e.g., hydrogels, such as cross-linked hydrogels, of the present invention). An organoid may comprise one or more (e.g., 1, 2, 3, 4, or more) differentiated cell type(s) depending upon the particular tissue and/or organ being modeled or emulated. Some organoids may comprise cancer cells, as discussed further below. When the organoid comprises cancer cells, they may include tissue cells, and/or may include a tissue mimic without cells, such as an extracellular matrix (or proteins and/or polymers derived therefrom), hyaluronic acid, gelatin, collagen, alginate, etc., including combinations thereof Thus, in some embodiments, cells are mixed together with an extracellular matrix, or cross-linked matrix, to form the organoid, while in other embodiments cell aggregates such as, e.g., spheroids and/or organoids may be pre-formed and then combined with the extracellular matrix and/or a composition of the present invention. In some embodiments, the organoid comprises cells that are human-derived cells, and, in some embodiments, the organoid comprises cells that consist of human-derived cells. An organoid of the present invention may express and/or produce one or more biomarkers (e.g., 1, 2, 3, 4, or more) that are the same as a biomarker produced by the cells in vivo. For example, liver cells in vivo produce albumin and an organoid of the present invention comprising liver cells may express albumin In some embodiments, an organoid may express a biomarker in the same amount or in an amount that is ±20%, ±10%, or ±5% of the average amount produced and/or expressed by corresponding cells in vivo. Example biomarkers include, but are not limited to, albumin, urea, glutathione S-transferase (GST) (e.g., α-GST), chemokines (e.g., IL-8, IL-1β, etc.), prostacyclin, SB100B, neuron-specific enolase (NSE), myelin basic protein (MBP), hormones (e.g., testosterone, estradiol, progesterone, etc.), inhibin A/B, lactate dehydrogenase (LDH), and/or tumor necrosis factor (TNF).

In some embodiments, an organoid is about 100 μm or 200 μm to about 350 or 500 μm in diameter, such as, for example, about 100, 150, 200, 250, 300, 350, 400, 450, or 500 μm. The organoid may comprise about 1,500, 2,000, 5,000 to about 10,000, 25,000, or 50,000 cells in total or about 1,000, 5,000, 10,000, or 50,000 to about 75,000, 100,000, or 150,000 cells in total.

"Growth media" as used herein may be any natural or artificial growth media (typically an aqueous liquid) that sustains the cells used in carrying out the present invention. Examples include, but are not limited to, an essential media or minimal essential media (MEM), or variations thereof such as Eagle's minimal essential medium (EMEM) and Dulbecco's modified Eagle medium (DMEM), as well as blood, blood serum, blood plasma, lymph fluid, etc., including synthetic mimics thereof In some embodiments, the growth media includes a pH color indicator (e.g., phenol red).

"Test compound" or "candidate compound" as used herein may be any compound for which a pharmacological or physiological activity, on a tissue (e.g., a cardiac tissue), or an interaction between two test compounds, is to be determined. For demonstrative purposes, isoproterenol, quinidine, propranolol, and epinephrine are example test compounds. However, any compound may be used, typically organic compounds such as proteins, peptides, nucleic acids, and small organic compounds (aliphatic, aromatic, and mixed aliphatic/aromatic compounds) may be used. Candidate compounds may be generated by any suitable techniques, including randomly generated by combinatorial techniques, and/or rationally designed based on particular targets. Where a drug interaction is to be studied, two (or more) test compounds may be administered concurrently, and one (or both) may be known compounds, for which the possible combined effect is to be determined. In some embodiments, the test compound is a metal, such as, but not limited to, aluminum, lead, etc. In some embodiments, the test compound is a heavy metal, such as, but not limited to, arsenic, cadmium, chromium, lead, and/or mercury. In some embodiments, the test compound is a pesticide.

A composition of the present invention may be used to prepare an organoid. In some embodiments, a composition of the present invention may be referred to as a "bioink" or a "bioink composition" (both of which are used interchangeably herein), and may comprise one or more live cell(s). As noted above, the cells may be animal cells (e.g., bird, reptile, amphibian, etc.) and in some embodiments are mammalian cells (e.g., dog, cat, mouse, rat, monkey, ape, human). The cells may be differentiated or undifferentiated cells, but are in some embodiments tissue cells (e.g., liver cells such as hepatocytes, pancreatic cells, cardiac muscle cells, skeletal muscle cells, etc.). However, the compositions of the present invention are not limited to use as a bioink and/or in bioprinting and may be useful in other areas, such as, for example, for encapsulation and/or delivery of an agent.

Choice of cells will depend upon the particular organoid being created. For example, for a liver organoid, liver hepatocyte cells may be used. For a peripheral or central nerve organoid, peripheral nerve cells, central nerve cells, glia cells, or combinations thereof may be used. For a bone organoid, bone osteoblast cells, bone osteoclast cells, or combinations thereof may be used. For a lung organoid, lung airway epithelial cells may be used. For a lymph node organoid, follicular dendritic lymph cells, fibroblastic reticular lymph cells, leukocytes, B cells, T cells, or combinations thereof may be used. For a smooth and/or skeletal muscle organoid, smooth muscle cells, skeletal muscle cells, or combinations thereof may be used. For a skin organoid, skin keratinocytes, skin melanocytes, or combinations thereof may be used. The cells may be differentiated upon initial incorporation into the composition, or undifferentiated cells that are subsequently differentiated may be used. Additional cells may be added to any of the compositions and/or hydrogels.

Cancer cells optionally used in the present invention may be any type of cancer cell, including but not limited to melanoma, carcinoma, sarcoma, blastoma, glioma, and astrocytoma cells, etc.

In some embodiments, cells may be obtained from a subject, such as, for example, a subject or patient undergoing treatment for cancer and/or that has cancer and/or a subject that has a compromised immune system. In some embodiments, cells are tumor cells, such as, e.g., patient biopsy-derived tumor cells, and organoids prepared from such cells may be used to screen potentially effective drugs and/or treatments. In some embodiments, cells may be obtained from a subject, such as, for example, a subject or patient undergoing treatment for cancer. In some embodiments, a tissue biopsied from a subject may be used to prepare one or more organoids of the present invention, optionally with cells obtained from a 2 mm×2 mm minced tissue. The cells may be differentiated at least in part to a particular cell or tissue type, such as brain, liver, intestine, pancreas, lymph node, smooth muscle, skeletal muscle, central nerve, peripheral nerve, skin, immune system, etc.

In some embodiments, an organoid of the present invention is not prepared from and/or does not comprise cells from an immortalized cell line. Organoids of the present invention may comprise and/or be prepared using high functioning cells, such as, but not limited to, primary cells and/or stem cells, e.g., induced pluripotent stems and/or differentiated iPS-derived cells.

The cells may be incorporated into the composition in any suitable form, including as unencapsulated cells, or as cells previously encapsulated in spheroids, or pre-formed organoids (as noted above). Animal tissue cells encapsulated or contained in polymer spheroids can be produced in accordance with known techniques, or in some cases are commercially available (see, e.g., Insphero AG, 3D *Hepg2 Liver Microtissue Spheroids* (2012); Insperio AG, 3D *InSight™ Human Liver Microtissues*, (2012)).

A composition of the present invention comprises thiolated hyaluronic acid (also referred to interchangeably herein as thiol-modified hyaluronic acid), methacrylated collagen (also referred to interchangeably herein as methacrylate-modified collagen) and/or methacrylated gelatin, and water. Any suitable thiolated hyaluronic acid, methacrylated collagen, and/or methacrylated gelatin may be used in the compositions of the present invention. In some embodiments, the composition comprises methacrylated collagen and the methacrylated collagen is methacrylated Type I, II, III, and/or IV collagen (optionally mammalian collagen). In some embodiments, the methacrylated collagen is methacrylated Type I collagen, optionally mammalian Type I collagen (e.g., from bovine). In some embodiments, the composition comprises methacrylated gelatin. In some embodiments, the thiolated hyaluronic acid may be heparinized, which may aid in and/or provide for growth factor sequestration and/or presentation. "Heparinized" as used herein refers to a compound that includes heparin chains that are covalently conjugated to the compound (e.g., hyaluronic acid).

In some embodiments, a composition of the present invention comprises a plurality of collagen fibers, optionally in a 3D construct, and/or is suitable for the formation of collagen fibers, optionally in a 3D construct. A composition of the present invention (e.g., a hydrogel of the present invention) may comprise a collagen fiber architecture (e.g., a micro-architecture) that may be organized (e.g., into bundles that may be aligned) by cells in the composition. In some embodiments, a composition of the present invention comprises collagen that one or more cells present in the composition can remodel to generate a collagen micro-architecture, which may be similar to a healthy and/or diseased tissue.

Methacrylated collagen or methacrylated gelatin may have about 1% to about 100% of the free amine groups (e.g., —NH$_2$ groups) on the collagen/gelatin modified with a methacrylate group (e.g., —C(O)C(CH$_2$)CH$_3$) to provide one or more methacrylate groups on the collagen/gelatin. In some embodiments, as is understood in the art, methacrylate may also refer to an acrylate group (e.g., —C(O)CHCH$_2$). Thus, is some embodiments, methacrylated collagen refers to collagen modified with an acrylate group, and methacrylated gelatin refers to gelatin modified with an acrylate group. In some embodiments, the secondary amine groups of the lysine residues present in the collagen or gelatin and/or the secondary amine groups on the N-termini of collagen or gelatin may be modified. In some embodiments, methacrylated collagen or gelatin may comprise a —NHC(O)C(CH$_2$)CH$_3$ group. In some embodiments, the methacrylated collagen or methacrylated gelatin may have about 1%, 5%, 10%, 15%, 20%, 25%, 30%, 35%, 40%, 45%, 50%, 55%, 60%, 65%, 70%, 75%, 80%, 85%, 90%, 95% or 100% of the free amine groups on the collagen/gelatin modified with a methacrylate group. In some embodiments, methacrylated collagen or gelatin may be as described and/or prepared in U.S. Pat. No. 8,658,711. In some embodiments, methacrylated collagen may be commercially available from Advanced BioMatrix (San Diego, Calif.), such as, e.g., from a kit under the tradename Lifeink®, such as, e.g., Lifeink® 100 or PhotoCol®, such as, e.g., PhotoCol®-UV.

A composition of the present invention may comprise methacrylated collagen or methacrylated gelatin in an amount from about 0.5 mg/mL of the composition to about 10 mg/mL of the composition. In some embodiments, methacrylated collagen or methacrylated gelatin may be present in the composition in an amount of about 0.5, 1, 1.5, 2, 2.5, 3, 3.5, 4, 4.5, 5, 5.5, 6, 6.5, 7, 7.5, 8, 8.5, 9, 9.5, or 10 mg/mL of the composition. In some embodiments, the amount of methacrylated collagen or methacrylated gelatin in the composition and/or the number of methacrylate groups present in the composition may be selected to obtain a desired stiffness of the composition (e.g., stiffness of the crosslinked hydrogel). In some embodiments, methacrylated collagen or methacrylated gelatin may be present in the composition in an amount from about 0.1, 0.5, 1, 2, 3, or 4 mg/mL of the composition to about 5, 6, 7, 8, 9, or 10 mg/mL of the composition.

Thiolated hyaluronic acid has at least one pendant thiol group (i.e., —SH group) off of the hyaluronic acid. In some embodiments, thiolated hyaluronic acid may comprise two or more (e.g., 2, 4, 6, 8, 10, 14, 20, 40, or more) pendant thiol groups. In some embodiments, thiolated hyaluronic acid may be commercially available from ESI BIO (Alameda, Calif.) under the tradename Heprasil® and/or may be obtained from a kit under the tradename HyStem®. The hyaluronic acid used to prepare the thiolated hyaluronic acid may be produced by bacteria and/or obtained by a fermentation process (e.g., a bacterial fermentation process), such as, e.g., using *Bacillus subtilis* as the host in an ISO 9001:2000 process. In some embodiments, the hyaluronic acid used to prepare the thiolated hyaluronic acid may derived from an animal (e.g., an avian and/or mammal) and/or fermentation source. The thiolated hyaluronic acid may have any suitable molecular weight, such as, e.g., a molecular weight from about 80, 100, or 500 kDa to about 1,000, 1,500, or 2,000 kDa. In some embodiments, the thiolated hyaluronic acid may have a molecular weight in a range from about 50 kDa to about 200 kDa and/or may have a molecular weight of about 50, 100, 150, or 200 kDa.

A composition of the present invention may comprise thiolated hyaluronic acid in an amount from about 0.1% to about 2% w/v of the composition. In some embodiments, thiolated hyaluronic acid may be present in the composition in an amount of about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% w/v of the composition.

Water may be present in a composition of the present invention in any suitable amount. In some embodiments, water may be present in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% by weight of the composition. In some embodiments, the composition is in the form of a hydrogel, optionally an extrudable hydrogel.

In some embodiments, a composition of the present invention has a ratio by volume of the thiolated hyaluronic acid to the methacrylated collagen and/or methacrylated gelatin in a range from 1:0.5 to 1:10 (thiolated hyaluronic acid:methacrylated collagen and/or methacrylated gelatin). In some embodiments, the ratio by volume of the thiolated hyaluronic acid to the methacrylated collagen and/or methacrylated gelatin is about 1:0.5, 1:1, 1:2, 1:3, 1:4, 1:5, 1:6, 1:7, 1:8, 1:9, or 1:10. In some embodiments, a composition of the present invention comprises a greater number of methacrylate groups (e.g., from the methacrylated collagen) than the number of thiols (e.g., from the thiolated hyaluronic acid). The number of methacrylate group may be about 2, 3, 4, 5, 6, 7, 8, 9, or more times greater than the number of thiols.

One or more (e.g., 1, 2, 3, 4, 5, 6, 7, or more) additional components may be present in a composition of the present invention. For example, in some embodiments, a composition of the present invention may comprise methacrylated gelatin (GelMa), heparin sulfate, chondroitin sulfate, alginate sodium salt, unmodified gelatin, elastin, non-thiolated hyaluronic acid, non-methacrylated collagen (e.g., Type I, II, III, and/or IV collagen), one or more components for modifying elastic modulus of the composition, one or more components for cell adhesion profile modification, one or more components for tissue-specific biochemical modification, and/or one or more small molecules (e.g., a small molecule that can has additional cross-linking capability and/or can provide hydrogen bonding and/or non-covalent complexing).

Example components for elastic modulus modification include, but are not limited to, poly(ethylene glycol) (PEG) diacrylate (DA) (PEGDA) at various molecular weights such as, e.g., from 500 Da to 20 kDa (e.g., 600 Da, 1 kDa, 2 kDa, 3.4 kDa, 5 kDA, and/or 10 kDA), PEG-di-acrylamide (PEGDAA) at various molecular weights such as, e.g., from 500 Da to 20 kDa (e.g., 600 Da, 1 kDa, 2 kDA, 3.4 kDa, 5 kDA, and/or 10 kDA), PEG-di-maleimide (PEGD-Mal) at various molecular weights such as, e.g., from 500 Da to 20 kDa (e.g., 600 Da, 1 kDa, 2 kDA, 3.4 kDa, 5 kDA, and/or 10 kDA), PEG-di-alkyne (PEGDMal) at various molecular weights such as, e.g., from 500 Da to 20 kDa (e.g., 600 Da, 1 kDa, 2 kDA, 3.4 kDa, 5 kDA, and/or 10 kDA), 4-Arm PEG acrylate at various molecular weights such as, e.g., from 1 kDa to 30 kDa (e.g., 2 kDA, 5 kDa, 10 kDA, and/or 20 kDA), 4-Arm PEG acrylamide at various molecular weights such as, e.g., from 1 kDa to 30 kDa (e.g., 2 kDA, 5 kDa, 10 kDA, and/or 20 kDA), 4-Arm PEG maleimide at various molecular weights such as, e.g., from 1 kDa to 30 kDa (e.g., 2 kDA, 5 kDa, 10 kDA, and/or 20 kDA), 4-Arm PEG alkyne at various molecular weights such as, e.g., from 1 kDa to 30 kDa (e.g., 2 kDA, 5 kDa, 10 kDA, and/or 20 kDA), 8-Arm PEG acrylate at various molecular weights such as, e.g., from 7 kDa to 50 kDa (e.g., 10 kDA, 20 kDa, and/or 40 kDA), 8-Arm PEG acrylamide at various molecular weights such as, e.g., from 7 kDa to 50 kDa (e.g., 10 kDA, 20 kDa, and/or 40 kDA), 8-Arm PEG maleimide at various molecular weights such as, e.g., from 7 kDa to 50 kDa (e.g., 10 kDA, 20 kDa, and/or 40 kDA), and/or 8-Arm PEG alkyne at various molecular weights such as, e.g., from 7 kDa to 50 kDa (e.g., 10 kDA, 20 kDa, and/or 40 kDA).

Example components for cell adhesion profile modification include, but are not limited to, fibronectin, laminin, RGD peptides, Type IV collagen, and/or Type III collagen. Example components for tissue-specific biochemical modification include, but are not limited to, extra cellular matrix (ECM) growth factor cocktails from primary tissue (e.g., from liver, pancreas, heart, brain, etc.), and individual growth factors. Example small molecules include, but are not limited to, catechol amines, a catechol containing an alkynyl imine, a catechol containing an alkynyl amine, a catechol containing an alkenyl imine, a catechol containing an alkenyl amine, a catechol containing an acrylate imine, a catechol containing an acrylate amine, a catechol containing a methacrylate imine, a catechol containing a methacrylate amine, and/or electrostatic linkers with acrylate, methacrylate, alkyne, and/or alkyne functional groups. In some embodiments, a small molecule present in a composition of the present invention is a compound described in International Publication No. WO 2018/081425, the contents of which are incorporated herein by reference. In some embodiments, a small molecule present in the composition may have a structure represented by Formula I or Formula II:

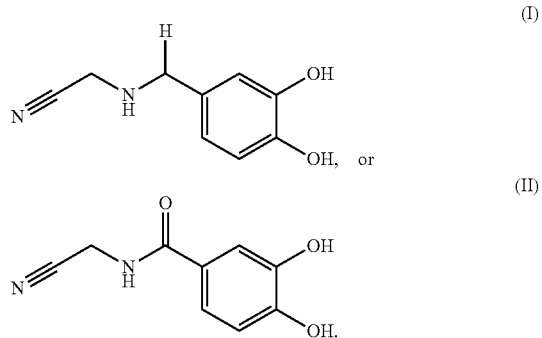

For example, catechol amines may be added in a modular fashion by employing alkyne (e.g., as shown in Scheme 1), acrylate, and/or methacrylate functionalization to bind to thiols in a composition of the present invention (e.g., hydrogel). Within a composition of the present invention, the catechol groups may be able to form hydrogen bonds (arrows), improving the mechanical properties of the composition (e.g., hydrogel).

Scheme 1: Example Use and/or Reaction of an Alkyne in a Composition Comprising HA and/or Gelatin.

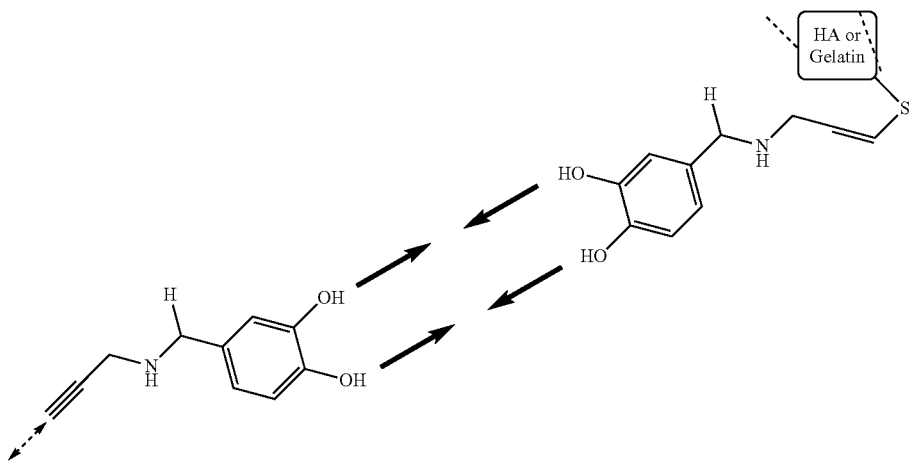

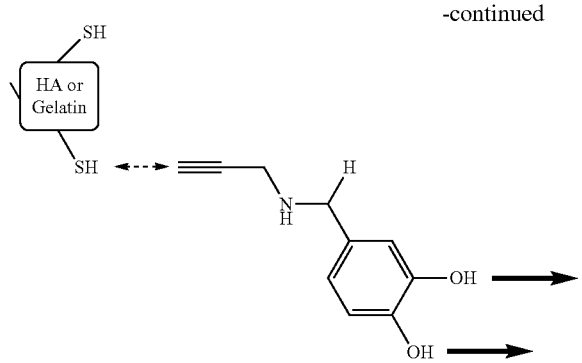

In some embodiments, a composition of the present invention comprises heparin, optionally thiol-modified heparin. The composition may comprise both non-thiol-modified heparin (i.e., heparin that is not modified to comprise a thiol group) and thiol-modified heparin. In some embodiments, the heparin (e.g., thiol-modified heparin) is heparin A and/or a sodium salt of heparin. Heparin may be obtained and/or derived from any suitable source, such as, e.g., a mammal (e.g., derived from porcine intestinal mucosa). In some embodiments, heparin may comprise a mixture of polyanion chains having a molecular weight in a range of about 5,000, 10,000, 15,000, or 17,000 Da to about 19,000, 20,000, or 25,000 Da. In some embodiments, heparin (e.g., thiol-modified heparin) may be commercially available from ESI BIO (Alameda, Calif.) under the tradename Heprasil® and/or may be obtained from a kit under the tradename HyStem®.

In some embodiments, a composition of the present invention may comprise one or more (e.g., 1, 2, 3, 4, 5, or more) small molecule(s). A small molecule may be covalently bound to gelatin, thiolated hyaluronic acid, non-thiolated hyaluronic acid, methacrylated collagen, methacrylated gelatin, and/or non-methacrylated collagen present in the composition, optionally prior to, during, and/or after a cross-linking reaction in the composition. A small molecule may comprise a functional group that provides hydrogen bonding (e.g., reversible hydrogen bonding). In some embodiments, a small molecule may comprise and/or be a catechol amine, a catechol containing an alkynyl imine, a catechol containing an alkynyl amine, a catechol containing an alkenyl imine, a catechol containing an alkenyl amine, a catechol containing an acrylate imine, a catechol containing an acrylate amine, a catechol containing a methacrylate imine, benzylamine, and/or a catechol containing a methacrylate amine.

In some embodiments, a composition of the present invention comprises a protein (e.g., an adhesion protein) and/or proteoglycan, optionally a modified protein and/or modified proteoglycan. In some embodiments, the protein and/or proteoglycan may be modified with one or more functional group(s), such as, e.g., modified with a maleimide or modified with a thiol, that can bind and/or crosslink to thiolated hyaluronic acid, non-thiolated hyaluronic acid, methacrylated collagen, methacrylated gelatin, and/or non-methacrylated collagen. In some embodiments, the composition comprises fibronectin, heparin, collagen (e.g., collagen III and/or collagen IV) and/or laminin, optionally a modified fibronectin, heparin, collagen and/or laminin (e.g., modified with a maleimide). In some embodiments, the composition comprises thiolated fibronectin, thiolated heparin, thiolated collagen (e.g., thiolated collagen III and/or thiolated collagen IV) and/or thiolated laminin. In some embodiments, an adhesion protein may be modified using a maleimide group functionalized with an amine group and/or carboxylic acid group. The maleimide group may be covalently bound to the adhesion protein by targeting N- and/or C-termini through simple EDCI-NHS chemistry, such as, e.g., shown in Scheme 2, and/or to an amino acid in the peptide sequence of the protein, such as, e.g., cysteine and/or proline.

Scheme 2: Example EDCI-NHS Chemistry to Covalently Link a Maleimide Functional Group to a Cell Adhesion Protein (e.g., Fibronectin, Laminin, and/or Collagen IV).

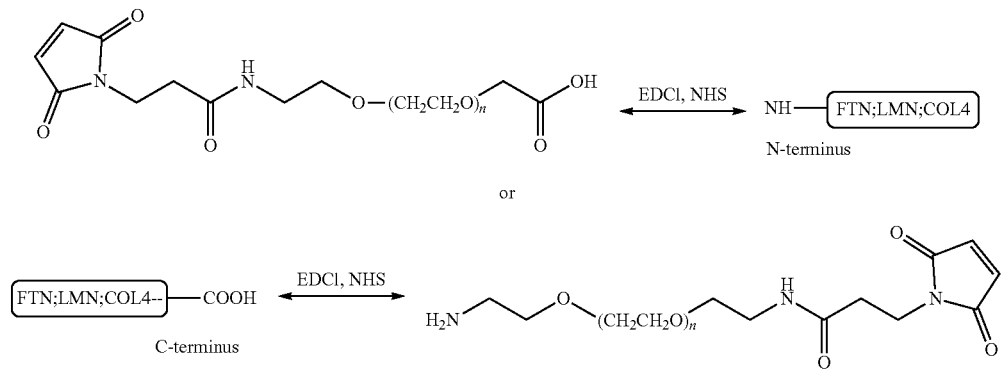

In some embodiments, a thiol-PEGlyated adhesion protein may be present in a composition of the present invention, such as, e.g., a thiol-PEGlyated fibronectin in which a new peptide bond may be formed at a lysine residue and/or at the N-terminus of the protein, such as, e.g., a compound having a structure represented by Formula III:

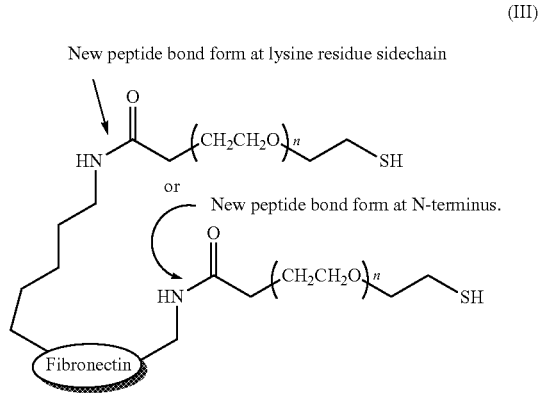

(III)

A modified protein (e.g., an adhesion protein) and/or proteoglycan may be present in a composition of the present invention in an amount of about 0.1, 0.2, 0.3, 0.4, 0.5, 0.6, 0.7, 0.8, 0.9, 1, 2, 3, 4, or 5 µg/mL of the composition to about 6, 7, 8, 9, or 10 µg/mL of the composition. In some embodiments, a modified protein (e.g., an adhesion protein) and/or proteoglycan may be present in a composition of the present invention in an amount of about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 µg/mL of the composition. In some embodiments, a modified fibronectin, heparin, collagen and/or laminin (e.g., modified with a maleimide or a thiol) may be present in a composition of the present invention in an amount of about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 µg/mL of the composition.

One or more growth factor(s) may be present in a composition of the present invention. In some embodiments, the composition comprises one or more growth factor(s) that are linked and/or bound by a heparin pendant chain. The one or more growth factor(s) may be appropriate for the particular cells that may be present in and/or added to a composition of the present invention and/or for the particular tissue substitute and/or organoid being produced. In some embodiments, growth factors and/or other growth promoting proteins may be provided in a decellularized extracellular matrix composition (ECM) from a tissue corresponding to the tissue cells (e.g., decellularized extracellular liver matrix when the live animal cells are liver cells; decellularized extracellular cardiac muscle matrix when the live animal cells are cardiac muscle cells; decellularized skeletal muscle matrix when the live animal cells are skeletal muscle cells; etc.). Additional collagens, glycosaminoglycans, and/or elastin (e.g., which may be added to supplement the extracellular matrix composition), etc., may also be included.

In some embodiments, a composition of the present invention comprises at least one polymer and/or thickening agent. Exemplary polymers and/or thickening agents include, but are not limited to proteins (e.g., collagen, gelatin, etc.), peptides, saccharides (e.g., sucrose), polysaccharides (e.g., celluloses, chitosan, alginates, etc.), polymers that can be crosslinked with itself, polymers that can be crosslinked with another component (e.g., in the presence of a crosslinking agent), thermo-responsive polymers, hyaluronates (e.g., hyaluronic acid), biocompatible polymers, natural polymers (e.g., silk), synthetic polymers (e.g., poly (acrylic acid) and derivatives thereof, poly(ethylene oxide) (PEG) and copolymers and/or derivatives thereof (e.g., PEG derivatives include, but are not limited to, poly(ethylene glycol) diacrylate (PEGDA) and PEG-di-maleimide), poly (vinyl alcohol), polyphosphazene, poloxamer, hydroxyethyl methacrylate, polydimethylsiloxane, polyacrylamide, poly (lactic acid), etc.), glycerin, and/or biodegradable polymers. In some embodiments, a composition of the present invention comprises at least one thickening agent, optionally wherein the thickening agent is unmodified hyaluronic acid, gelatin, glycerin, and/or sucrose.

In some embodiments, a composition of the present invention may be customized to match the biochemical profile of one or more (e.g., 1, 2, 3, 4, 5, or more) tissue(s) (e.g., a tissue found in a mammalian body). In some embodiments, an adhesion protein such as, e.g., one found in a particular tissue, may be synthetically modified to allow for direct coupling to a component in the composition (e.g., the thiolated hyaluronic acid and/or methacrylated collagen). Growth factors may be linked through heparin pendant chains. Fibronectin, laminin, and/or other adhesion proteins may be synthetically modified to have one or more chemical group(s) that crosslink directly into a component in the composition (e.g., the thiolated hyaluronic acid and/or methacrylated collagen), which may allow for tissue-specific customization. In some embodiments, inclusion of covalently linked fibronectin in the composition may have a significant influence in maintaining function of an organoid formed and/or provided in the composition (e.g., a liver organoid).

A composition of the present invention may include an initiator (e.g., a thermal or photoinitiator). Any suitable initiator that catalyzes the reaction involving unreacted methacrylate groups (e.g., unreacted methacrylate groups on the methacrylated collagen) may be employed. An example photoinitiator is 4-(2-hydroxyethoxy)phenyl-(2-hydroxy-2-propyl)ketone. In some embodiments, an initiator (e.g., a photoinitiator) may be present in a composition of the present invention in an amount from about 0.01% to about 0.1% or 1% w/v of the composition. In some embodiments, the initiator is present in the composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% w/v of the composition.

In some embodiments, a composition of the present invention includes a crosslinking group. Any suitable crosslinking groups can be used, including but not limited to multi-arm thiol-reactive crosslinking agent, such as polyethylene glycol dialkyne, other alkyne-functionalized groups, acrylate or methacrylate groups, and/or other components for elastic modulus modification.

A composition of the present invention may have a pH of about 6, 6.5, or 7 to about 7.5 or 8. In some embodiments, the composition has a pH of about 6, 6.5, 7, 7.5, or 8. In some embodiments, the composition has a pH of about 7. In some embodiments, when the composition has a pH below 7, the composition is in liquid form. In some embodiments, when the composition has a pH at or above 7, the composition is in the form of a gel, optionally an extrudable gel.

A composition of the present invention may have an elastic modulus (i.e., stiffness), at room temperature and atmospheric pressure, that is sufficiently low such that the composition can be manipulated and/or deposited onto a substrate by whatever deposition method is employed (e.g., extrusion deposition, bioprinting, etc.). The elastic modulus, again at room temperature and atmospheric pressure, of the composition may be sufficiently high so that the composition will substantially retain the shape and/or configuration in which it is deposited, optionally until subsequent cross-linking (whether that cross-linking be spontaneous, thermal or photo-initiated, etc.).

In some embodiments, a composition of the present invention may have an elastic modulus (E') from about 0.01, 0.025, 0.05, 0.1, 1, or 5 kiloPascals to about 10, 15, 20, 25, 50, or 100 kiloPascals (kPa). In some embodiments, a composition of the present invention may have an elastic modulus (i.e., stiffness) from about 0.01, 0.025, 0.05, or 0.1 kiloPascals to about 0.5, 1, 5, 10, 15, 20, or 25 kiloPascals, or more, at room temperature and atmospheric pressure. In some embodiments, the composition, prior to deposition and/or prior to initiator-driven cross-linking, has a stiffness of from about 10 or 25 Pascals (Pa) to about 500 Pa at room temperature and atmospheric pressure. In some embodiments, the composition, prior to deposition and/or prior to initiator-driven cross-linking, has a stiffness of about 10, 25, 50, 75, 100, 150, 200, 250, 300, 350, 400, 450, or 500 Pascals at room temperature and atmospheric pressure. In some embodiments, the composition, after deposition and/or after initiator-driven cross-linking, has a stiffness from about 0.1 kPa to about 25 kPa at room temperature and atmospheric pressure. In some embodiments, the composition, after deposition and/or after initiator-driven cross-linking, has a stiffness of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, or 25 kPa at room temperature and atmospheric pressure. A composition of the present invention may mimic the elastic modulus of a tissue in vivo. In some embodiments, a composition of the present invention has an elastic modulus value that is substantially the same as (i.e., within ±20% of) the elastic modulus value of a tissue in vivo.

A composition of the present invention may have an elastic modulus after extrusion and/or bioprinting that varies by less than about ±20% compared to an elastic modulus of the composition prior to extrusion and/or bioprinting. In some embodiments, the composition may have an elastic modulus (G') and a loss modulus (G") that are within about ±20%, 15%, 10%, or 5% of each other or less. In some embodiments, a composition of the present invention is thixotropic. In some embodiments, during the application of a stress, a composition of the present invention has an elastic modulus that decreases and then, after removal of the stress, the composition returns to an elastic modulus that is similar to the elastic modulus prior to the stress (e.g., within about ±20%).

In some embodiments, a composition of the present invention has one or more properties and/or features (e.g., reversible and/or transient bonds within the composition) that allow for and/or provide shifts in elastic moduli in response to a physical stress. For example, the shear stress levels encountered for a composition when driven through a printhead, upon reaching some stress threshold, the transient bonds may break and the shear elastic modulus (G') may be reduced to a level below the shear loss modulus (G"), at which point the composition is effectively a fluid and is easily extruded. Immediately following deposition, the stress from the printing is no longer present and the internal bonds reform, returning the composition to a gel state that holds its 3D shape. In some embodiments, a composition of the present invention, upon application of a stress, has an elastic modulus (G') that is below the loss modulus (G"), but, upon removal of the stress, the elastic modulus (G') is above the loss modulus (G").

A composition of the present invention may be extrudable. For example, in some embodiments, the composition may be extrudable from a syringe and/or bioprinter. In some embodiments, the composition may be extruded with an applied mechanical stress in a range from about 5 kPa to about 80 kPa. In some embodiments, the composition may be extruded with an applied mechanical stress of about 5, 10, 15, 20, 25, 30, 35, 40, 45, 50, 55, 60, 65, 70, 75, or 80 kPa. In some embodiments, the composition is extrudable through a 19.5, 20, 22, 23.5, or 30.5 Gauge needle, optionally at room temperature and/or pressure. The composition may be liquid upon extrusion and after extrusion may be solid. A composition of the present invention may be stable and solid under normal conditions, but is printable and can transition between a solid-like behavior at rest, and a liquid-like behavior during printing. In some embodiments, a composition of the present invention is thixotropic. Thixotropism is a material characteristic that is a special case of shear thinning, and refers to the material's ability to behave like a solid under low shear conditions and behave like a liquid under high shear conditions. In some embodiments, a composition of the present invention remains a solid while in a syringe, behaves like a liquid when subjected to the high shear environment of extrusion through the nozzle and/or needle of the syringe, and then regains its solid like characteristics upon deposition (e.g., onto a surface of a substrate and/or into a composition). In some embodiments, a composition of the present invention is thixotropic, can retain its shape following deposition (e.g., extrusion from a syringe and/or printer), and can support two or more layers of the composition.

Example compositions of the present invention include, but are not limited to, the following compositions:

Example Composition 1

25% Heprasil® solution including Heprasil® (i.e., thiolated hyaluronic acid) at 10 mg/mL (1% w/v) and photoinitiator (PI) at 0.05% w/v
75% Methacrylated collagen solution, wherein the methacrylated collagen solution comprises 6.75% mL Neutralization solution, 45.5% mL Methacrylated collagen I (6 mg/mL), and 22.75% mL acetic acid Example Composition 2 (Optionally Used to Prepare Liver Organoids)

25% Heprasil® solution including Heprasil® at 10 mg/mL (1% w/v) and PI at 0.05% w/v
75% Methacrylated collagen solution, wherein the methacrylated collagen solution comprises 6.75% mL Neutralization solution, 45.5% mL Methacrylated collagen I (6 mg/mL), and 22.75% mL acetic acid
Thiolated fibronectin mixed in to the composition at 0.25 µg/mL Example Composition 3 (Optionally Used to Prepare Adipose Organoids)

25% Heprasil® solution including Heprasil® at 10 mg/mL (1% w/v) and PI at 0.05% w/v
75% Methacrylated collagen solution, wherein the methacrylated collagen solution comprises 6.75% mL Neutralization solution, 45.5% mL Methacrylated collagen I (6 mg/mL), and 22.75% mL acetic acid Thiolated laminin mixed in to the composition at about 0.25 µg/mL to about 0.5 µg/mL (e.g., 0.25 µg/mL or 0.5 µg/mL)

Optionally thiolated fibronectin mixed in to the composition at about 0.25 µg/mL to about 0.5 µg/mL (e.g., 0.25 µg/mL or 0.5 µg/mL)

Example Composition 4 (Optionally Used to Prepare Pancreas Organoids)

25% Heprasil® solution including Heprasil® at 10 mg/mL (1% w/v) and PI at 0.05% w/v 75% Methacrylated collagen solution, wherein the methacrylated collagen solution comprises 6.75% mL Neutralization solution, 45.5% mL Methacrylated collagen I (6 mg/mL), and 22.75% mL acetic acid Thiolated laminin mixed in to the composition at about 0.25 µg/mL to about 10 µg/mL (e.g., 0.25 µg/mL, 0.5 µg/mL, 1 µg/mL, 5 µg/mL, or 10 µg/mL)

Example Composition 5 (Optionally Used to Minimize Collagen-Collagen Crosslinking Prior to Bioprinting)

25% Heprasil® solution including Heprasil® at 10 mg/mL and PI at less than 2% w/v (e.g., at about 0.05%-1% w/v)

75% Methacrylated collagen solution, wherein the methacrylated collagen solution comprises 6.75% mL Neutralization solution, 45.5% mL Methacrylated collagen I (6 mg/mL), and 22.75% mL acetic acid, and the methacrylated collagen solution is diluted in DMEM cell culture media prior to combining with Heprasil® so that the final concentration of methacrylated collagen is between 0.5 mg/mL and 2 mg/mL Example Composition 6 (Optionally Used to Prepare Neural Organoids)

50% Heprasil® solution including Heprasil® at 10 mg/mL and PI at 0.05% w/v

50% Methacrylated gelatin solution, wherein the methacrylated gelatin solution comprises Methacrylated or thiolated gelatin I (10 mg/mL).

Example Composition 7 (Optionally Used to Prepare Cardiac Organoids)

25% Heprasil® solution including Heprasil® at 10 mg/mL and PI at 0.05% w/v

75% Methacrylated collagen solution, wherein the methacrylated collagen solution comprises 6.75% mL Neutralization solution, 45.5% mL Methacrylated collagen I (6 mg/mL), and 22.75% mL acetic acid Thiolated fibronectin mixed in to the composition at 10 µg/mL Provided according to some embodiments of the present invention are methods of preparing and/or using a composition of the present invention. Some embodiments include a method of making a hydrogel and/or an organoid. The method may comprise providing a composition of the present invention comprising thiolated hyaluronic acid and methacrylated collagen (e.g., methacrylated Type 1 collagen) at a pH of about 6.5 or 7 to about 7.5 or 8 to provide a hyaluronic acid-collagen hydrogel. In some embodiments, the method may comprise providing a composition of the present invention comprising thiolated hyaluronic acid and methacrylated gelatin at a pH of about 6.5 or 7 to about 7.5 or 8 to provide a hyaluronic acid-gelatin hydrogel. In some embodiments, the composition and/or hydrogel comprises one or more cell(s), optionally one or more live cell(s) obtained and/or derived from a subject.

The method may comprise cross-linking (e.g., spontaneously cross-linking) thiols from the thiolated hyaluronic acid (HA) and methacrylate groups from the methacrylated collagen or methacrylated gelatin. The thiol groups on the thiolated hyaluronic acid and the methacrylate groups on the collagen fibers may spontaneously react and/or form cross-links at a pH of about 6.5 or 7 to about 7.5 or 8, optionally at physiological pH and/or a pH from about 7 to about 7.4 (i.e., pH-driven cross-linking).

In some embodiments, the hyaluronic acid-collagen hydrogel or hyaluronic acid-gelatin hydrogel may be used to provide, contain, encapsulate, suspend, and/or form a 3D cell culture and/or organoid. In some embodiments, the hyaluronic acid-collagen hydrogel or hyaluronic acid-gelatin hydrogel may be manipulated and/or further cross-linked, optionally for use in bioprinting.

A method of the present invention may comprise adding, combining, mixing, and/or the like thiolated hyaluronic acid and methacrylated collagen and/or methacrylated gelatin at pH in a range from about 6.5 or 7 to about 7.5 or 8. A soft and/or pliable hydrogel may be provided after the adding, combining, mixing, and/or the like. In some embodiments, cells (e.g., live cells) may be added to the composition (e.g., hydrogel) after and/or while the thiolated hyaluronic acid and methacrylated collagen and/or methacrylated gelatin are combined, mixed, and/or the like. In some embodiments, cells may be added to the hyaluronic acid-collagen hydrogel or hyaluronic acid-gelatin hydrogel at, e.g., about 1, 5, 10, 15 minutes to about 20, 25, 30, 35, 40 minutes or more after the adding, combining, mixing, and/or the like of the thiolated hyaluronic acid and methacrylated collagen and/or methacrylated gelatin.

A method of the present invention may comprise modulating the ratio of HA thiols and collagen and/or gelatin methacrylate groups. In some embodiments, the composition and/or hydrogel comprises methacrylate groups that were not crosslinked during the pH-driven crosslinking step, and a portion (e.g., 5%, 10%, 25%, 50%, 75%, 90%, etc.) and/or all of these methacrylate group may be cross-linked in the presence of an initiator (e.g., a thermal initiator and/or photoinitiator) to provide an initiator-driven cross-linking, which may facilitate additional customization of the mechanical properties of the resulting 3D structure. In some embodiments, methacrylate groups that were not crosslinked during the pH-driven crosslinking step may be cross-linked by UV and/or visible light in the presence of a photoinitiator. In some embodiments, the initiator-driven cross-linking may stabilize the 3D structure of the hydrogel and/or bond individual filaments and/or components in the hydrogel together.

Additionally or alternatively, using available thiol and/or methacrylate groups prior to a crosslinking step (e.g., prior to the pH-driven cross-linking step and/or prior to the initiator-driven cross-linking step), additional components that are functionalized with compatible chemical groups may be added for further customization. For example, a method of the present invention may comprise bonding one or more small molecule(s), protein(s), and/or proteoglycan(s) to a portion of the hyaluronic acid-collagen hydrogel (e.g., to a portion of the hydrogel polymer backbone, thiolated hyaluronic acid, and/or methacrylated collagen) or hyaluronic acid-gelatin hydrogel. In some embodiments, the hyaluronic acid-collagen hydrogel or hyaluronic acid-gelatin hydrogel comprises one or more functional groups that provide hydrogen bonding (e.g., reversible hydrogen bonding). In some embodiments, after the pH-driven cross-linking step and prior to the initiator-driven cross-linking step, the elastic modulus of the hyaluronic acid-collagen hydrogel or hyaluronic acid-gelatin hydrogel may be tuned and/or modulated, such as, e.g., to support extrusion and/or deposition (e.g., in a bioprinting device). For example, a hydrogel of the present invention may have one or more component(s) and/or interaction(s) as shown in FIG. 1.

A hyaluronic acid-collagen hydrogel or hyaluronic acid-gelatin hydrogel of the present invention may mimic the elastic modulus of a tissue in vivo. A method of the present invention may comprise increasing the elastic modulus (e.g., stiffening) of the hyaluronic acid-collagen hydrogel or hyaluronic acid-gelatin hydrogel. In some embodiments, increasing the elastic modulus of a hydrogel of the present invention is performed prior to, during, and/or after the initiator-driven crosslinking of the hydrogel (e.g., using a thermal initiator and/or photoinitiator). For example, increasing the elastic modulus of the hyaluronic acid-collagen hydrogel may comprise adding a functionalized polyethylene glycol (PEG) compound (e.g., an acrylate functionalized polyethylene glycol) to the hyaluronic acid-collagen hydrogel and optionally then performing a cross-linking step in the presence of an initiator (e.g., a photoinitiator).

In some embodiments, a small molecule and/or peptide comprises a first end and/or moiety that can be tethered and/or bound covalently to a polymer backbone in the composition (e.g., to the thiolated HA backbone) and a second end and/or moiety that is functionalized with one or more (e.g., 1, 2, 3, 4, or more) group(s) that may create hydrogen bonding (e.g., reversible hydrogen bonding), electrostatic, and/or non-covalent interactions (e.g., peptide-peptide non-covalent interactions). Providing one or more hydrogen bonding (e.g., reversible hydrogen bonding), electrostatic, and/or non-covalent interactions may provide the composition and/or hydrogel with one or more mechanical properties and/or a thixotropic property. Thixotropy is a unique mechanical property that allows a material to dynamically change its stiffness in response to external forces, such as, e.g., those encountered while a composition (e.g., a bioink) is forced through a syringe and/or print-head. A composition and/or hydrogel of the present invention may balance reversible hydrogen bonds with covalent bonds to provide a dynamic stimuli-sensitive composition. In some embodiments, a composition of the present invention may exist as a gel containing cells, but upon application of one or more stress(es) such as, e.g., a stress experienced during extrusion through a syringe and/or a bioprinting protocol, will mechanically "fail" and dynamically decrease in stiffness, which may allow for extrusion printing to easily be performed. After the composition is extruded (e.g., after it passes through needle and/or the print-head of the device) and/or the one or more stresses are removed or decreased (e.g., decreased to less than 50% of the prior stress), the composition may regain its stiffness and ability to hold a 3D form.

Figure 2:
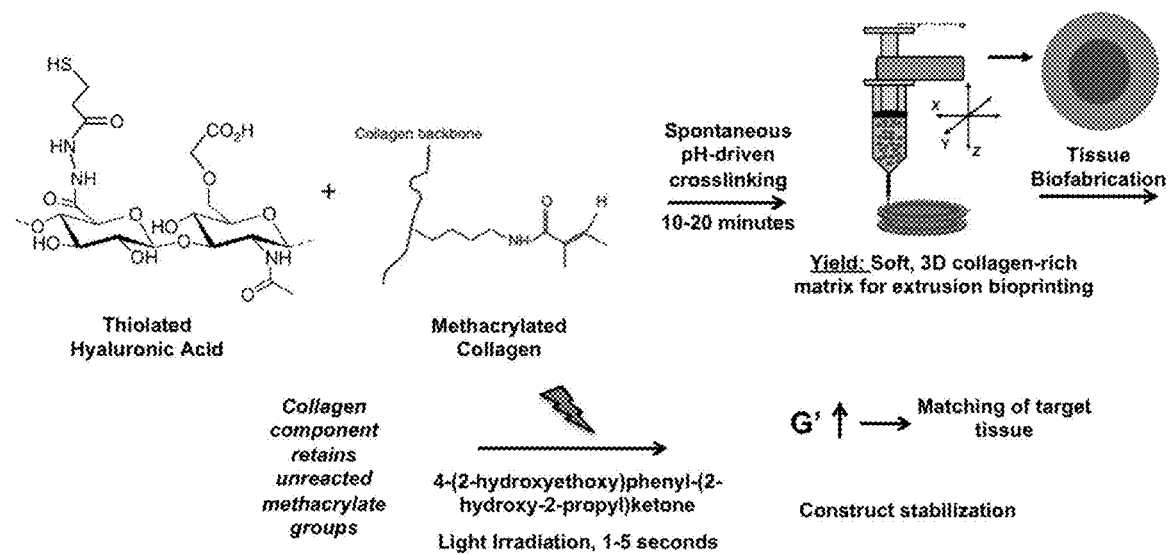
FIG. 2 is a schematic of example base components in a composition of the present invention and an example method for bioprinting the composition.

In some embodiments, a method of the present invention comprises extruding and/or depositing (e.g., bioprinting) the hyaluronic acid-collagen hydrogel or hyaluronic acid-gelatin hydrogel onto a substrate. In some embodiments, a method of the present invention may comprise one or more step as shown in FIG. 2.

In some embodiments, a method of the present invention comprises increasing the viability and/or functional activity of an organoid, optionally compared to the viability and/or functional activity of an organoid not in accordance with a method and/or composition of the present invention. The method may comprise providing a composition of the present invention comprising live cells and/or preparing an organoid prepared according to a method of the present invention, the method comprising providing a composition of the present invention, and optionally culturing the organoid in the composition.

A composition and/or method of the present invention may comprise and/or provide one or more (e.g., 1, 2, 3, 4, 5, 6, 7, 8, or more) different tissue(s) and/or organoid(s) that each are viable for at least 1, 2, 3, 4, or more weeks. In some embodiments, a composition and/or method of the present invention may comprise and/or provide one or more of tissue(s) and/or organoid(s) that are viable and may comprise at least about 75% or more (e.g., about 80%, 85%, 90%, 95% or more) living cells based on the average number of cells present in the tissue and/or organoid at 1, 2, 3, 4, or more weeks (e.g., in culture in the composition). The tissue and/or organoid may be generated by differentiation from a common cell sample (e.g., a sample such as a skin or tumor biopsy sample collected from a subject). The tissue and/or organoid may comprise cells in proportions similar to the proportions of cells present in the corresponding native (e.g., human) tissue. In some embodiments, the tissue and/or organoid comprises metastatic and/or malignant cells. In some embodiments, a function and/or property of the tissue and/or organoid may be determined and/or measured and compared to the function and/or property of a corresponding native tissue (e.g., a property of a liver organoid may be measured and compared to the same property of a liver tissue in a subject). In some embodiments, a function and/or property of the tissue and/or organoid may be similar to the function and/or property of a corresponding native tissue.

In some embodiments, a composition and/or method of the present invention can achieve a take rate of at least 50% or more such as, e.g., about 50%, 55%, 60%, 65%, 70%, 75%, 80%, 85%, 90%, 95%, 98%, or more. For example, a 90% take rate means that 90% of the time a viable organoid or plurality of organoids (e.g., an organoid set) is achieved and/or provided by a method of the present invention. That is, for a 90% take rate, 9 out of 10 cell samples (e.g., tumor cell samples) yield a viable organoid or plurality of organoids when prepared according to a method of the present invention.

In some embodiments, a composition and/or method of the present invention may be used to provide a multi-layered hydrogel construct, optionally wherein one or more layers of the hydrogel construct have a different composition than one or more different layers of the hydrogel construct. For example, a first layer of a hydrogel construct may comprise methacrylated collagen, thiolated hyaluronic acid, and elastin and a second layer of the hydrogel construct may comprise methacrylated collagen, thiolated hyaluronic acid, and laminin. In some embodiments, the one or more layers of a hydrogel construct may comprise different cells. The one or more layers may or may not be visually distinguishable.

The foregoing and other aspects of the invention are explained further in the following examples.

EXAMPLES

Example 1

Three bioink formulations ("HA-collagen bioink") were prepared and the viscoelastic behavior as well as cellular behavior within the material was quantified. The HA-collagen bioinks were formulated in three concentrations: 1:2, 1:3, and 1:4 (Heprasil® from Hystem-HP kit: methacrylated collagen type-1 from Advanced Biomatrix). Collagen was prepared as instructed by Advanced Biomatrix at 6 mg/mL and Heprasil® was prepared to 1% w/v with 0.1% photointiator in $DiH_2O$ and warmed to 37° C. Bioink formulations underwent rheological, cell viability, and 3D bioprinting testing conducted on the BioBots 1 device. As a comparison, tests were performed using the a Hystem-HP kit (thiolated hyaluronic acid and gelatin) made with 0.1% photointiator in $DiH_2O$. Rheology was performed to determine shear elastic moduli G' and 3D bioprinting was utilized to test printability of each material. Organoids were formed in 10 μL drops of bioink with 100.00 cells per organoid, containing BXP3C, HCT116, Lx2, or pfHSC cell lines. Live/dead staining and picrosirus red collagen bundling analysis was performed on Lx2 and pfHSC organoids to assess viability and micro-architecture formation. A short term 5-Fluorouracil (5-FU) drug study was also conducted on HCT116 to show drug efficacy invariance between the Hystem-HP kit and 1:3 formulated bioink. Lastly, HCT116, Lx2, and HepRGs were bioprinted together in the 1:3 bioink formulation to produce a 3D bioprinted liver microenvironment.

For initial tests, BXP3C or LX2 pancreatic cells were used to create 3D tissue constructs in HyStem-HP, a HA and gelatin-based hydrogel system, as a control condition. In comparison, the HA-collagen bioink was combined in the three different formulations, varying the ratios of base components. On days 1 and 7 of culture, cell viability was assessed using LIVE/DEAD staining. Viability at both time points in all formulations was very high—typically above 90% in most cases—demonstrating that the new bioink formulations are as effective as the well-established and commercially available Hystem-HP hydrogel.

For further validation of the bioink's capabilities to support cell cultures, difficult to maintain primary tumor cells isolated from actual patients were employed. As these primary cells rarely take well in traditional 2D cell cultures, they serve as an additional validation step for the bioink. Two biospecimens were received: 1) a high grade appendiceal tumor, and 2) a low grade appendiceal tumor. These biospecimens were rinsed, minced, and dissociated using collagenase/hyaluronidase overnight before being encapsulated in the 1:3 HA-Collagen bioink formulation. The HyStem-HP hydrogel was used as a control. In high grade appendiceal tumor constructs and low grade appendiceal constructs, we see denser tissue, improved tumor biomarker expression, collagen rearrangement, and collagen presence. While not wishing to be bound to any particular theory, this may suggest that the inclusion of the CollMA component of the bioink may be important for preserving phenotypic (and perhaps genotypic) integrity in culture.

Using the cell types described in the viability and histology panels above, picrosirius red staining was performed to highlight well-defined, cell-remodeled collagen fibers versus unbundled, immature collagen. Hepatic stellate cells and LX2 pancreatic cells were both capable of reorganizing the CollMA component of the bioink. Additionally, the primary low grade and high grade appendiceal tumor cells were also able to modulate the collagen microarchitecture, albeit to a lesser degree. In comparison, HA-Collagen bioinks without any cells were assessed by picrosirius red staining. In these no-cell controls, regions of no collagen reorganization are present. Additionally, the only significant red-yellow regions are likely due to edge effects. This collection of data demonstrates the important compatibility between the bioink and the cells within, resulting in cell-driven microarchitecture within 3D tissue constructs.

Figure 3:
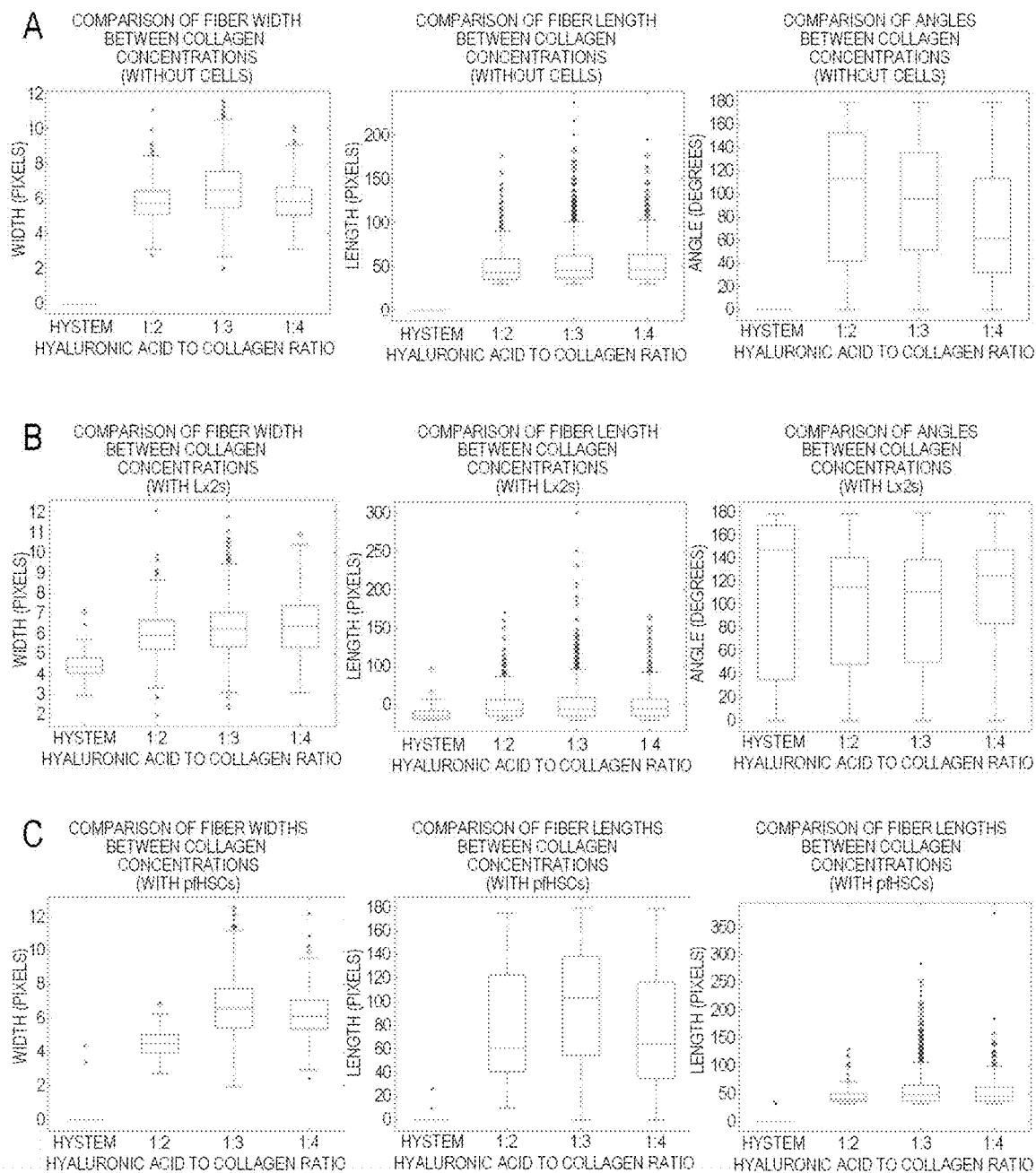
FIG. 3 shows graphs from CTFire analysis of extracellular matrix microarchitecture in bioink-based tissue constructs. Constructs were formed with A) no cells, B) LX2 cells, or C) pfHSCs.

These picrosirius red staining images were used to quantify collagen micro architecture (FIG. 3). To produce these data sets, 3 representative images were taken from each organoid of each type and data was yielded using CT-FIRE, the data for each of the representative images was then combined and shown in the plots. Notably, the collagen-containing bioinks allow for collagen reorganization, which results in different levels of collagen fiber width, length, and angles.

Figure 4:
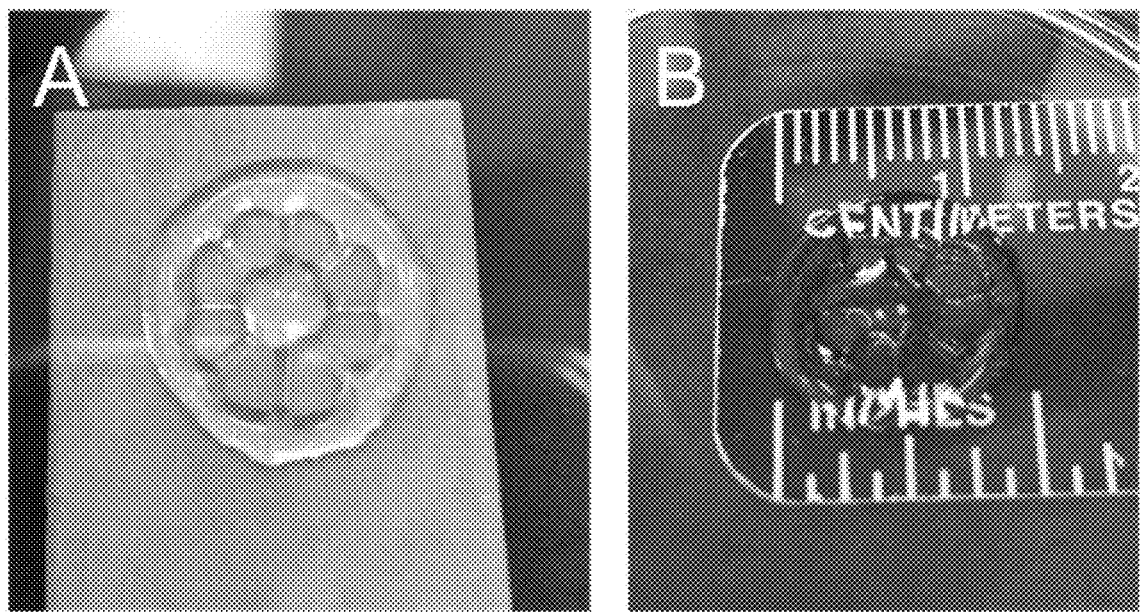
FIG. 4 shows an image of an example construct design to test bioink extrusion ease, resolution, and fidelity.

Bioink formulations have been tested in several extrusion bioprinters, including the Cellink Inkredible bioprinter and the BioBots BioBot 2 bioprinter. FIG. 4 shows a simple ring and spoke construct that we are exploring for future liver constructs (liver parenchyma and sinusoids). This structure showcases the range in print filament widths, with thick and thinner zones.

Figure 5:
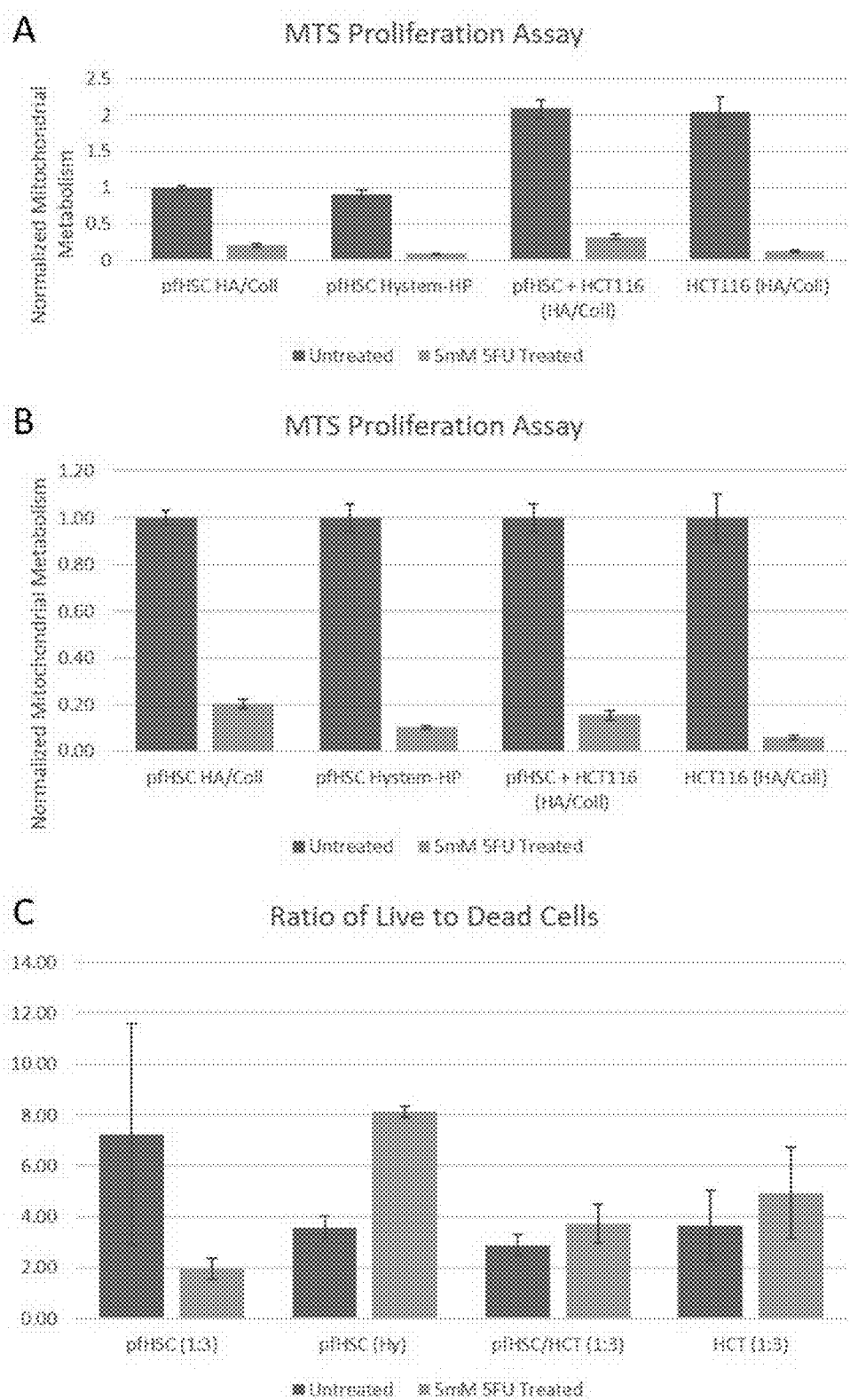
FIG. 5 shows graphs, which demonstrate that 5-Fluorouracil drug effects vary based on both cell and bioink hydrogel environment. A and B) MTS proliferation assay showing mitochondrial metabolism under no treatment and the drug. C) Ratio of live to dead cells.

Using the methods described, we were able to obtain data showing the printability of each to the formulated bioinks based on their viscoelastic properties. Each of the concentrations was capable of extrusion printing and showed differences in properties based on collagen content. Organoids showed strong viability within the collagen based bioinks, with little difference compared to the Hystem-HP hydrogel. This data demonstrates that the bioink is able to maintain viability of cells which can be a common problem with extrusion bioprinting. The organoid studies also allowed for assessment of micro-architecture. Using picrosirus red staining, we could delineate between bundled and unbundled collagen which varies between each of the formulations. The 5-FU drug treatment, MTS assay data (FIG. 5) showed lower metabolism within the drug treated organoids and a larger ratio of dead cells in comparison to the control. This additionally confirms invariance between the the Hystem-HP and bioink systems with regard to diffusion of drug, nutrients, and reagents. To specifically further the development of liver organoid structure, we 3D bioprinted HCT116, Lx2, and HepRG cells in a physiologically relevant design to show viability of multiple cell lines within a single printed culture.

These results show that we have been able to create a collagen type-1 based bioink for 3D printing applications. Using this material, we demonstrated high viability for multiple cell types, positive presence of cell-organized micro-architecture, successful use in drug screening tests, and bioprinting of a 3D liver construct.

Example 2

Figure 6:
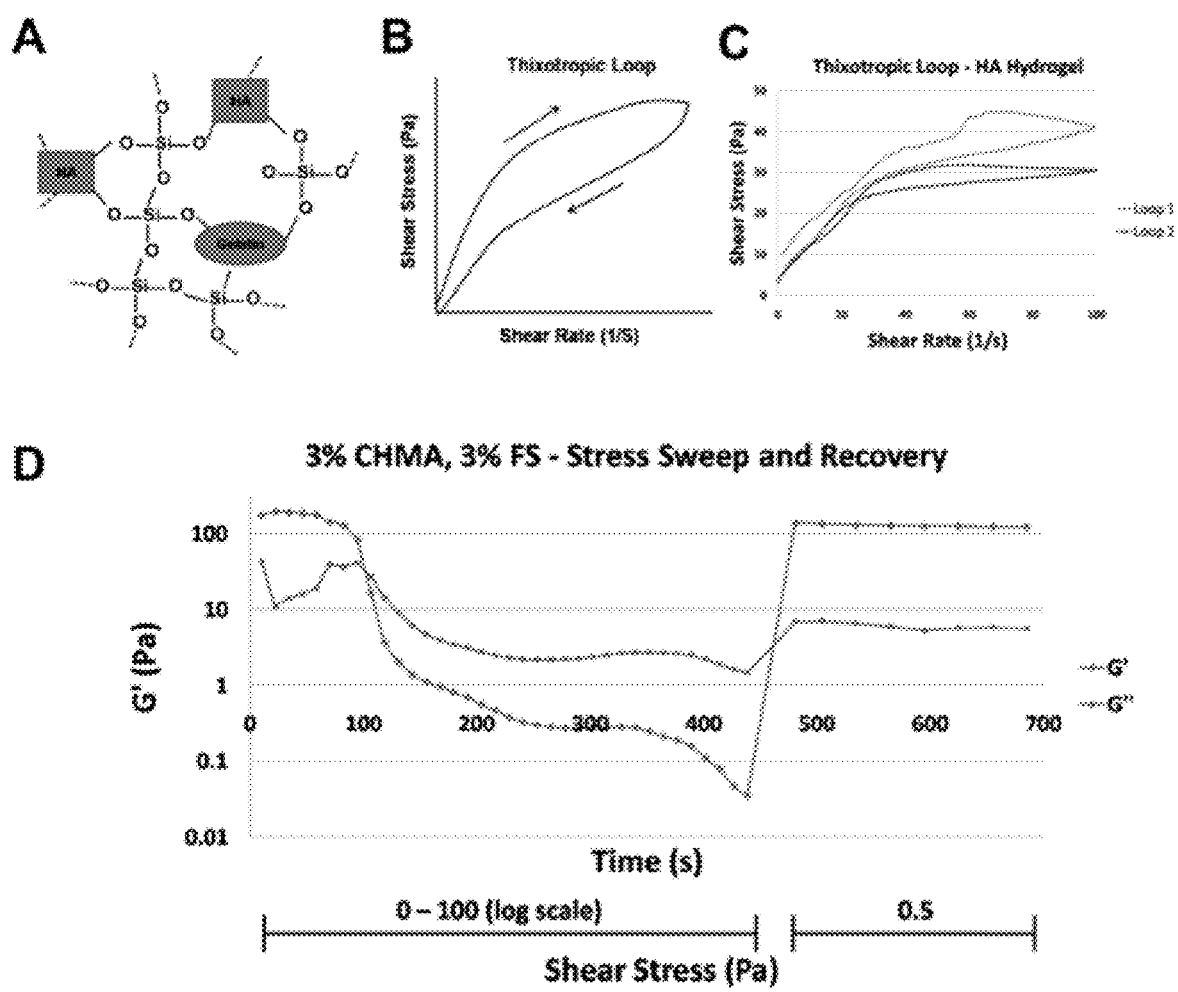
FIG. 6, panel A shows a Hyaluronic acid and gelatin thixotropic hydrogel, formed using complexing with tetraorthosilicate (TEOS). Panel B shows A depiction of a thixotropic loop mechanical test and panel C shows the HA-gelatin thixotropic hydrogel under such a test, indicating thixotropic characteristics. Panel D shows a stress sweep and recovery.

A composition having thixotropic characteristics was developed. Tetraorthosilicate (TEOS) was used to form nanocomplexes within HA and collagen/gelatin system (FIG. 6, panel A).

The following different compositions were prepared as described further below:
HA-methacrylate+TEOS,
HA-methacrylate+gelatin-methacrylate+TEOS,
HA-methacrylate+collagen-methacrylate+TEOS,
HA-S+gelatin-methacrylate+TEOS, and
HA-S+collagen-methacrylate+TEOS.

For each of these different compositions, the synthesis was started by mixing TEOS and 0.1 M acetic acid in a 1:9 volume ratio and stirring it for 1 to 2 hours before use. This hydralizes the TEOS, allowing it to form small nanoparticles with free carboxyl groups, with alcohol as a byproduct. The HA and gelatin components are dissolved in water in 1 to 3% w/v solutions. If fumed silica is desired as a thickening agent, it is added to the HA/gelatin solution and allowed to dissolve. An HA/gelatin solution is then added to a TEOS solution in a 5:3 volume ratio, vortexed, and the pH is adjusted to between 7 and 8 with NaOH. The mixture is allowed to sit overnight to allow hydrogen bond formation between the carboxyl groups of the TEOS nanoparticles and the hydroxide groups of the HA and gelatin components, resulting in HA and gelatin containing TEOS nanoparticles. The resulting material is then washed with water, centrifuged, and the water is removed by aspiration. This is repeated a number of times to remove any traces of alcohol, which can disrupt the bonds necessary for hydrogel formation. The resulting material can then be characterized and tested to verify thixotropy and biocompatibility.

In the preliminary work developing these kinds of hydrogels, two rheological testing protocols were established—the thixotropic loop and the stress sweep and—using a TA Instruments rheometer and software.

Before beginning either of the tests, the rheometer is first calibrated and a sample is loaded. Because of the thixotropic nature of these materials, loading the sample is simple. The gels are drawn into a syringe to measure out the correct volume and deposited on the center of the rheometer plate. The geometry, or 40 mm steel plate is lowered spreading out the sample uniformly and the testing protocols can be initiated.

In the thixotropic loop test, the continuous shear rate applied is increased from 0 (1/s) to some maximum, which is dependent on the material, and decreased back to 0. The resulting shear stress measured by the rheometer increases until it usually plateaus, and then decreases back to the starting point, forming a loop (FIG. 6, panel B). Notably, our HA material was able to generate a thixotropic loop (FIG. 6, panel C). The second common rheological test for thixotropy is a stress sweep followed by a recovery period. Over time, shear stress is applied to the material, increasing logarithmically until a maximum, and then removed and replaced with a low stress used to simply to retrieve data while the material is recovering. As the stress increases, G' gradually decreases before it plummets below G", and begins behaving as a liquid since G" is dominant When the high stress is removed, G' recovers, and the material recovers to its elastic state. When applied to our material, the stress sweep and recovery test appears to mimic the behavior of a thixotropic material (FIG. 6, panel D).

Next we performed a bench top simulation of extrusion bioprinting. The material was vortexed and flowed, but exists in a gel state when no stress is applied. Suction caused stress high enough to reduce. G', allowing the gel to be drawn into a syringe, after which it can be smoothly extruded like during a bioprinting procedure.

Example 3

Bioinks were customized to match the biochemical profiles of different tissues in the body. Specifically, adhesion proteins were synthetically modified to allow for direct coupling to the bioink. Growth factors can also be linked through heparin pendant chains.

Figure 7:
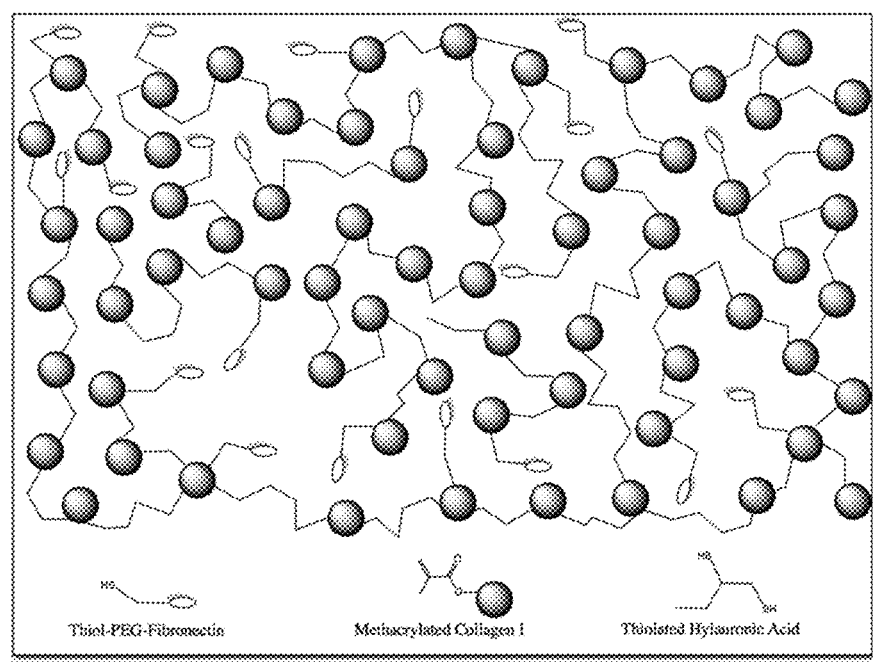
FIG. 7 is a representation of the hydrogel bioink network containing covalently linkable fibronectin proteins.

As a first step in creating adhesion proteins that can be covalently bound to the bioink network, fibronectin was modified with functional groups. In a 50 mL reaction flask, dissolve 5 mg of SH-PEG-COOH (MW=10 kDa) with 5 mL of 0.05-M MES, 0.5-M NaCl, pH 6.0 reaction buffer. Prepare stock solutions of 0.2-M EDC and 0.5-M sulfo-NHS in reaction buffer and quickly aliquot the volumes necessary to achieve a final concentration 2-mM EDC and 5-mM sulfo-NHS in reaction mixture containing the SH-PEG-COOH. Allow to mix and react for 15 minutes at room temperature. Quench the reaction and isolate the activated SH-PEG-Sulfo-NHS ester through a desalting resin column. Dissolve 5 mg of Fibronectin (isolated from human plasma) in 5 mL of 1X DPBS, pH 7.4 and add directly to the isolated activated SH-PEG-Sulfo-NHS ester solution. Allow to react for 4 hours at room temperature. Purify SH-PEG-Fibronectin species from small molecule byproducts through an overnight dialysis against 1X DPBS, pH 7.4. Freeze the dialyzed protein solution overnight at −80° C. and lyophilize for 24-48 Hrs. The thiol-PEGlyated fibronectin is then ready for integration into the methacrylated collagen/thiolated HA-composed bioink, and was mixed into the collagen and HA solution prior to crosslinking or bioprinting. This thiolated fibronectin protein can now be covalently linked into any methacrylate, acrylate, or alkyne-containing matrix, ensuring immobilization of the protein and cell adhesion peptide sequence (FIG. 7).

Immobilization of fibronectin in the bioink was then verified by assessing cell adhesion and spreading behavior with pfHSCs. Fibronectin (16 μg per 10 μL construct) was added to collagen which was used to make organoids using the bioink with pfHSCs (3 million cells/mL). On days 1, 4, 7, and 10, organoids were removed from culture, fixed, and stained with phalloidin and DAPI. Macro-confocal microscopy was used to visualize cells within the organoid, and revealed that the addition of fibronectin resulted in cell elongation behavior 3 days earlier than in conditions without fibronectin.

Figure 8:
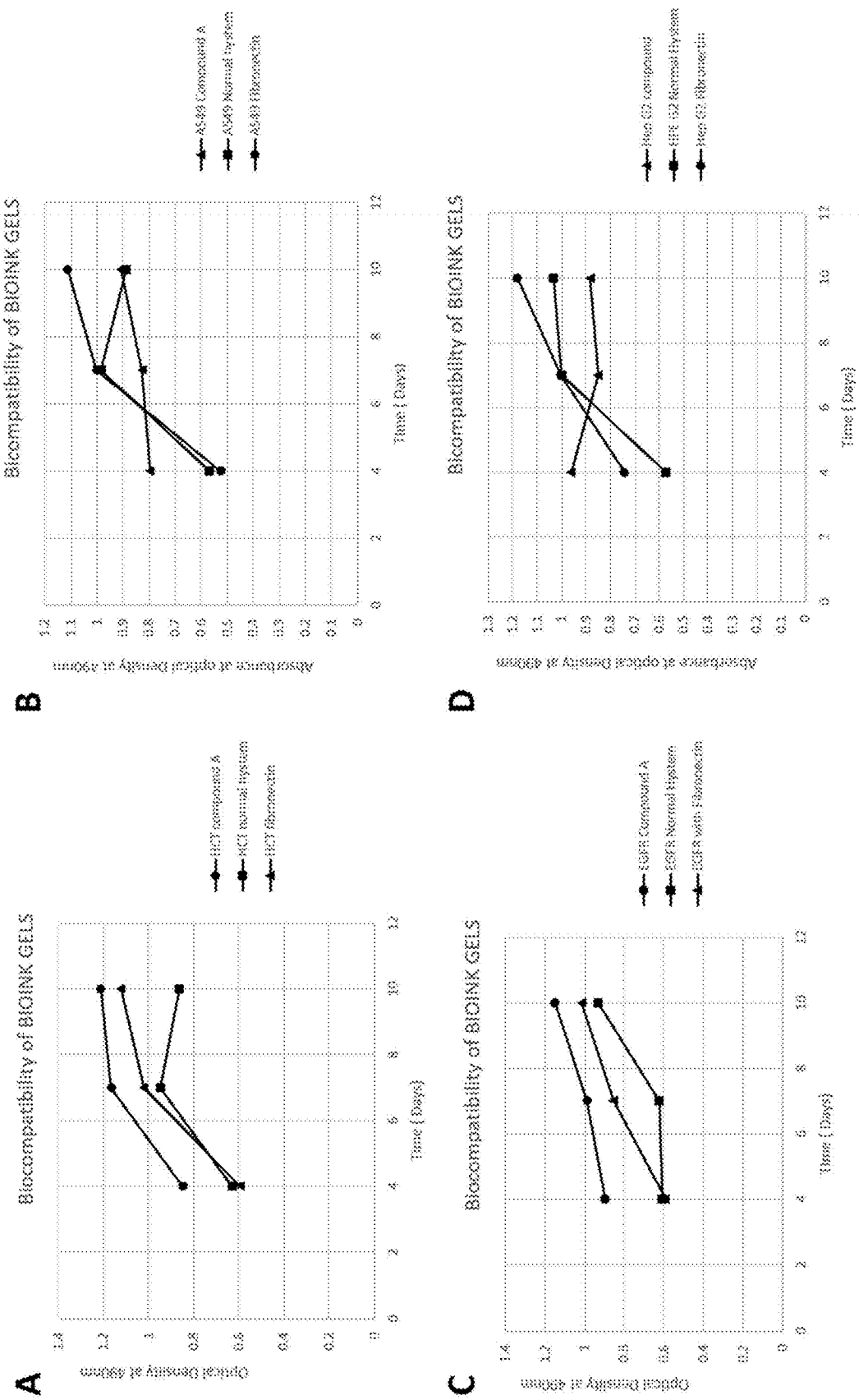
FIG. 8 shows MTS proliferation data on bioink formulations for A) HCT116 cells, B) A549 cells, C) U87 EGFRvIII cells, and D) Hep G2 cells. Compound A refers to the catecholamine-containing thixotropic bioink. Normal HyStem hydrogel (HA and gelatin commercially available hydrogel) is used as a control material. Fibronectin refers to bioinks containing fibronectin.

To verify viability, screens with a panel of cell lines was performed using MTS proliferation assays (FIG. 8) and LIVE/DEAD staining. As can be gathered from these data, viability continued to be very high—typically above 90% in most cases—demonstrating that the new bioink formulation is as effective as the well-established and commercially available Hystem-HP hydrogel.

Example 4

Figure 9:
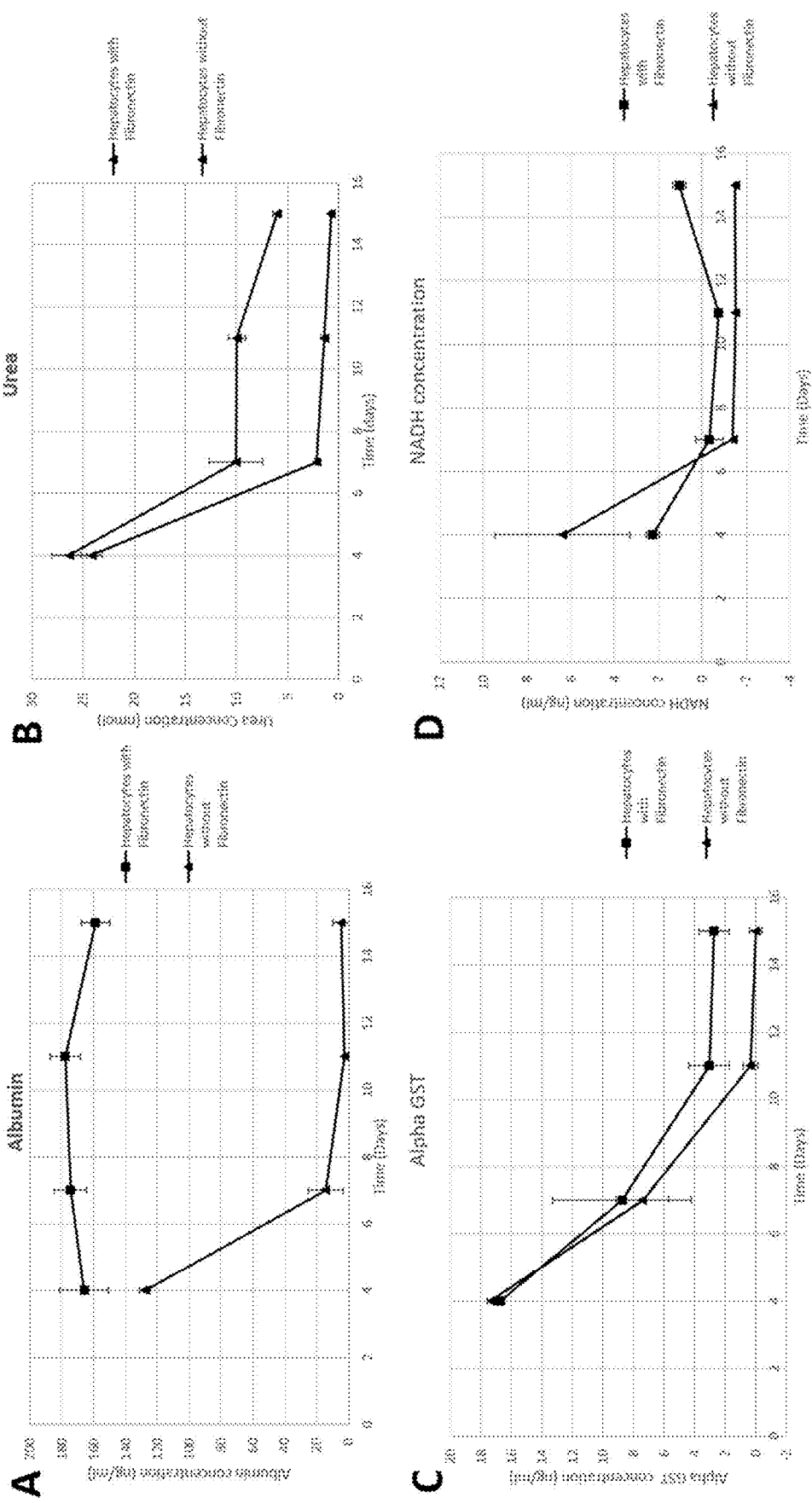
FIG. 9 shows graphs liver construct secretion of A) albumin, B) urea, C) α-GST, and D) LDH, quantified by ELISA or colorimetric assays. Bioinks with or without fibronectin were tested. In general, constructs are healthy with positive albumin and urea secretion, while α-GST and LDH should remain low, as they are released upon cell apoptosis.
Figure 10:
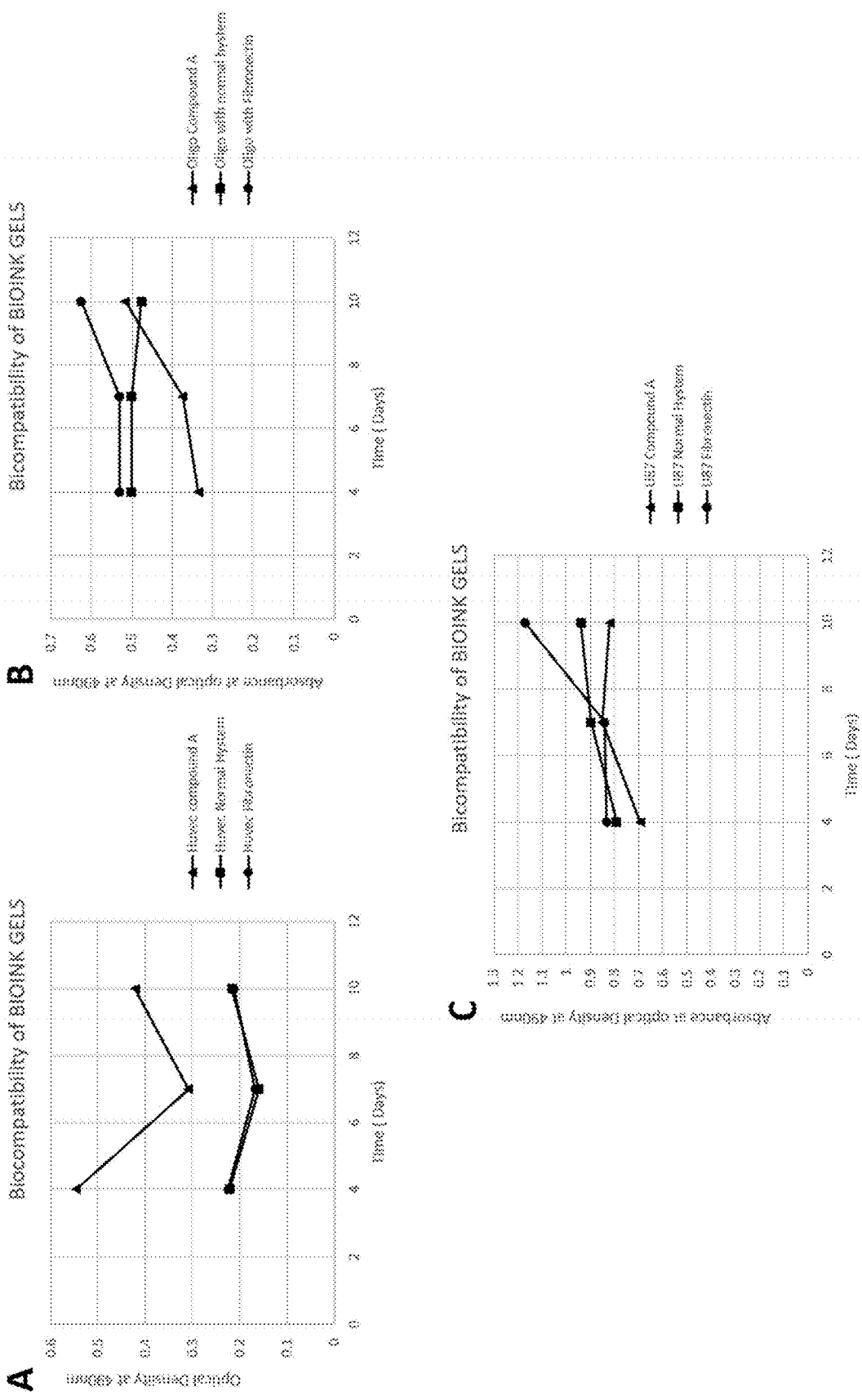
FIG. 10 shows graphs of MTS proliferation data on bioink formulations for A) HUVEC cells, B) oligodendrite cells, and C) U87 cells. Compound A refers to the catecholamine-containing bioink. Normal HyStem hydrogel (HA and gelatin commercially available hydrogel) is used as a control material. Fibronectin refers to bioinks containing fibronectin.

Prototype liver tissue constructs were printed using primary human hepatocytes and primary liver stellate cells. Constructs remained robust in culture with high cellularity, are viable in culture and produced albumin and urea, with low levels of α-glutathion-S-transferase (α-GST) and lactate dehydrogenase (LDH, both of which are secreted upon apoptosis of liver cells) (FIG. 9). MTS proliferation data on bioink formulations for A) HUVEC cells, B) oligodendrite cells, and C) U87 cells is provided in FIG. 10.

Example 5

For this study, a one-step photo-initiated, radical-mediated polymerization technique was used to create a thixotropic hydrogel matrix. A catecholamide compound was synthesized and integrated into an existing HA-based hydrogel system using thiol-yne 'click' chemistry. Printability was assessed using a Biobiots 3D bioprinter, and material characterization was performed using an oscillatory shear strain sweep test using a Discovery HR-2 rheometer Cell-viability was confirmed using Live/Dead assays.

Figure 11:
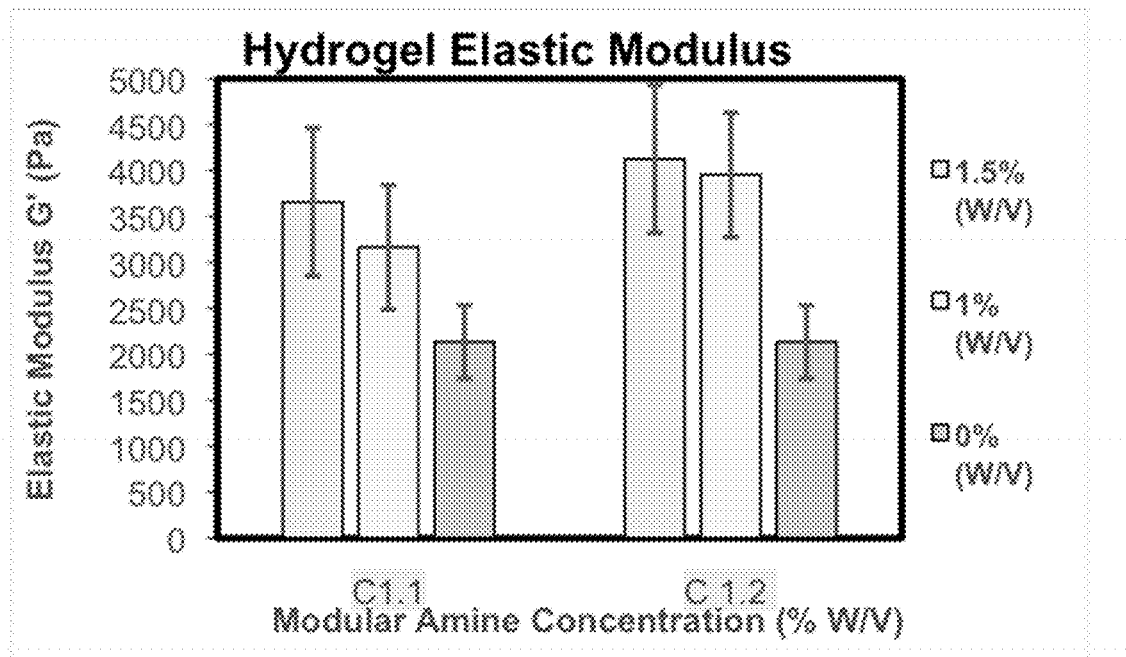
FIG. 11 shows a graph of Elastic Modulus G' (Pa) vs. Modular Amine (C1.1/C1.2) Concentration (% W/V). To ensure standard conditions across all experiments the geometry was lowered into the gels until a calibration normal force of 0.4 N was observed. Following, a shear-stress sweep test (0.6-10.0 Pa, 1.0 Hz, 25° C.) was applied to hydrogels containing varying concentrations (0%, 1.0%, and 1.5% W/V) of modular amine compounds, C1.1/C1.2. Reported here is the averaged G' value for (n=3) runs at (0%, 1.0% and 1.5% W.V) for each compound. Reported uncertainties were calculated using the standard deviations between the averaged G' values within (n=3) runs of each concentration. As the % W/V concentration of amine increased a directly proportional increase in the G' value within 1σ was observed.
Figure 12:
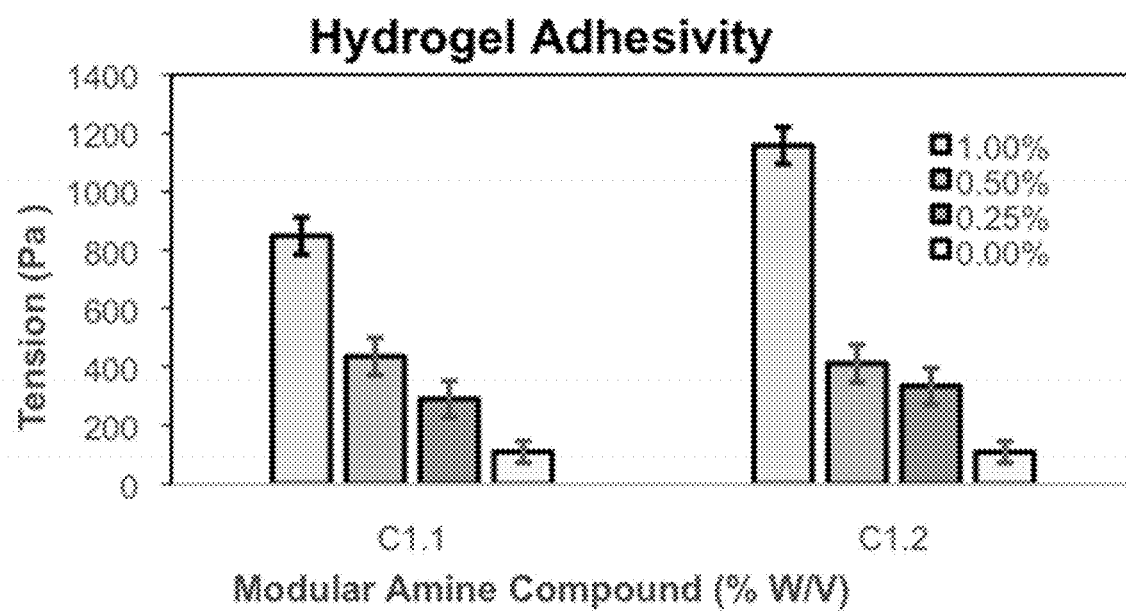
FIG. 12 shows a graph of Viscidity Tension (Pa) vs. Modular Amine (C.1/C1.2) Concentration (% W/V). To ensure standard conditions across all experiments the geometry was lowered into the gels until a calibration force of 0.4 N was observed. Following, a stickiness tension test (2000 μm, 25° C.) was applied to hydrogels containing varying concentrations (0%, 1.0%, and 1.5% W/V) of modular amine compounds, C1.1/C1.2. As the concentration of the amine (C1.1/C1.2) was increased from 0% to 0.25% W/V to 0.50% W/V we observed a directly proportional increase in the tensile force (1.00×10^2+/−61.6) Pa. Increasing the concentration from 0.50% W/V to 1.0% W/V for C1.1 we observed a (4.00×10^2=/−61.6) Pa increase. And in a similar manner, increasing the concentration from 0.50% to 1.0% W/V for C1.2 we observed a (6.00×10^2+/−61.6) Pa increase.
Figure 13:
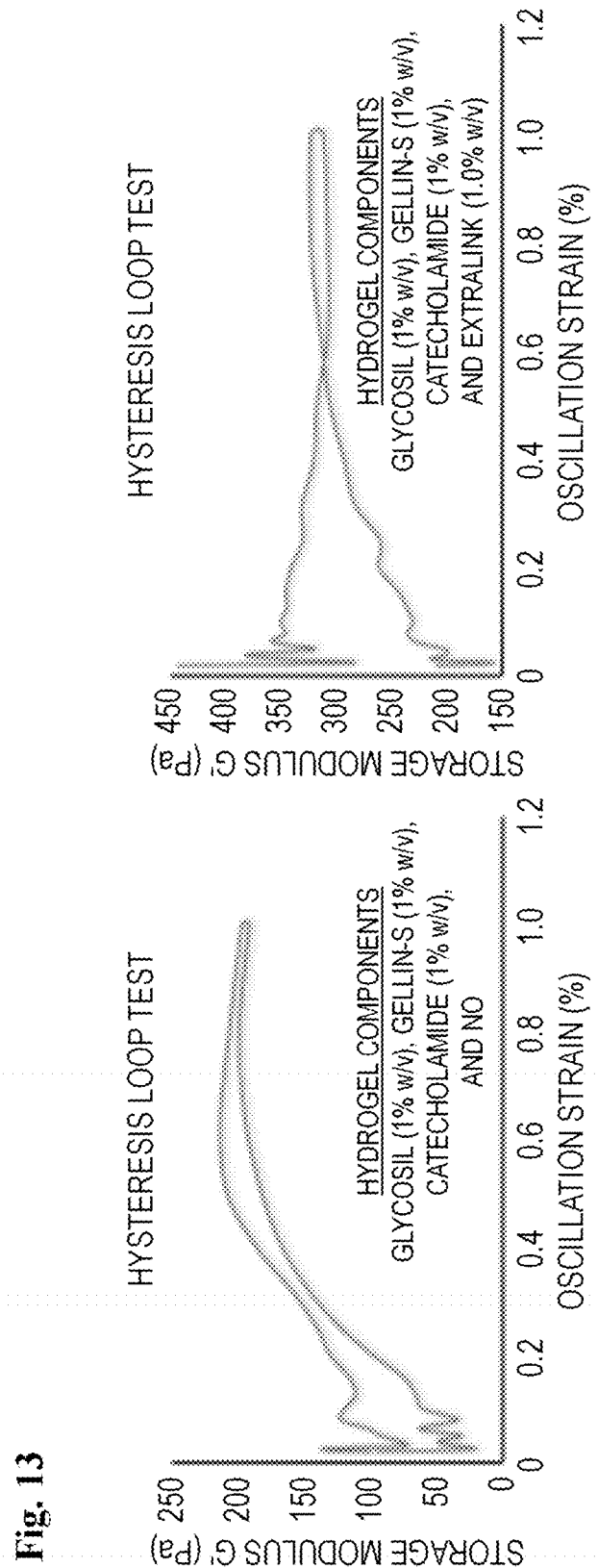
FIG. 13 shows graphs with the results from an oscillation Amplitude Shear Strain Test w/catecholamide and no PEGDA and from an oscillation Amplitude Shear Strain Test w/catecholamide and PEGDA. C1.2"=condition containing modular catecholamide compound.

Testing of preliminary molecules showed that addition of catechol amine compounds with linkable alkyne groups could be incorporated into a modular HA hydrogel system described above via photopolymerizable coupling to thiol groups along the HA backbones and gelatin molecules. Importantly, hydrogen bonding between the catechol groups now covalently bound to the hydrogel network (via thiol-alkyne bonds) further increased the shear elastic modulus G' values of the hydrogel constructs (FIG. 11). These increases were not observed in control groups. This gives validation to the activity of the newly added catechol components of the system. In further testing we observed significantly more "stickiness" in the hydrogel constructs during mechanical shear testing runs. Following this observation, we employed the rheometer using a customized protocol to apply a tensile stretch to hydrogels that had been immobilized between the base and testing geometry of the rheometer. The geometry was brought into contact with the sample and lowered until 0.4 N normal force was reached by the load cell. At this point, the sample was allowed to equilibrate for 30 seconds, after which the rheometer applied constant displacement vertically at 5 µm/s, raising the geometry 1000 µm, during which time resistive force ("stickiness") was measured by the load cell every second. Preliminary test results showed a 5-fold increase in tensile resistance due to the increased adhesive nature of the catechol amine containing hydrogel (FIG. 12). The results demonstrate that through lowering the concentration of PEG crosslinkers to zero (FIG. 13) we can transform the hydrogel's reliance on covalent bonds to hydrogen bonding interactions.

Example 6

LX2 hepatic stellate cells were cultured within collagen or a HA-Collagen bioink with covalently bound laminin, fibronectin, or both. After 7 days, the constructs were fixed and stained with phalloidin to highlight the actin cytoskeleton of the cells and DAPI for nuclei. What is evident is that modulating laminin versus fibronectin changes the morphology and phenotype of the cells within the constructs. While not wishing to be bound to any particular theory, these changes are likely due to activation of different integrin receptors responsible for binding to collagen, laminin, and fibronectin cell adhesion motifs. Notably, laminin appears to drive phenotype towards one of epithelial nature while fibronectin appears to drive phenotype (round/cuboidal, spread out, cobblestone-like morphology) towards one of mesenchymal (elongated, spindle-shaped morphology).

Example 7

Thiolated HA (Heprasil®, ESI-BIO) is dissolved to form a 1% w/v solution with 0.05% w/v w/v 2-hydroxy-4'-(2-hydroxyethoxy)-2-methylpropiophenone photoinitiator (Irgacure 2959, Sigma), while methacrylated collagen (Photocol, Advanced Biomatrix) is dissolved to form a 6 mg/mL solution. HA and collagen are mixed in a 1:3 ratio by volume and the resulting solution is mixed in a 12:1 ratio by volume with a catecholamidoalkyne solution, which may include a compound of Formula I or II. The concentration of the catecholamidoalkyne in the catecholamidoalkyne solution can be manipulated to modulate the overall effect of H-bonding. Cells can then be added and the material can be deployed for bioprinting or other studies. Irradiation with UV or blue light is then used to initiate the sol-gel transition.

Example 8

Methacrylated collagen type I ("COL I") was combined with thiolated hyaluronic acid (HA) to produce a bioink that is printable with physiologically relevant native ECM-derived components. While not wishing to be bound to any particular theory, it was hypothesized that an intermediate ratio of COL I to HA is both best for printing and tissue organization in comparison to an industry standard HA/gelatin hydrogel. To test this hypothesis, matrix organization, printing properties, and cell biocompatibility of the bioinks were analyzed and compared. Two hepatic stellate cell types were used within three bioink formulation made of COL I and HA for cell viability and functional testing. Further, a heterocellular liver model was bioprinted to assess whether the bioink could support liver function and drug response. To the best of our knowledge, this is the first COL I/HA hybrid bioink for 3D bioprinting. Through utilization of a functioning liver model, we have been able to show strong support for the use of COL I/HA hybrid bioinks in bioprinting applications.

MATERIALS AND METHODS

Bioink Formulation

Bioink formulations were prepared by combining methacrylated COL I and thiolated HA in three ratios for initial testing and characterization. Methacrylated COL I (collagen) was prepared at 6 mg/mL per manufacturer's instructions excluding the provided photoinitiator (Advanced Biomatrix, San Diego, Calif.). Prior to use with HA, the collagen was neutralized using manufacturer provided neutralization solution at 85 µL of solution per milliliter of collagen. HA was prepared at 2 mg/mL by re-suspending Heprasil® (heparinized and thiolated HA, ESI BIO, Alameda, Calif.) in 1 mL deionized water with 0.1% w/v photoinitiator (Sigma Aldrich, 410896, St. Louis, Mo.). Three ratios of collagen to HA were used for the studies (2:1, 3:1, and 4:1; COL I:HA).

Rheology Characterization

A Discovery HR-2 Rheometer (TA Instruments, New Castle, Del.) with an 8 mm parallel plate geometry was used to collect the rheological data. After hydrogel precursor preparation, 200 µL of the reaction mixture was transferred into a 12 mm diameter×5 mm depth PDMS well. The PDMS well containing the reaction mixture was then either measured as is or exposed to ultraviolet (UV) radiation of 1.9 W/cm$^2$ for 2 seconds at a distance of 1 cm, resulting in instantaneous photo-initiated polymerization and hydrogel formation. To ensure standard conditions across all experiments the geometry was lowered into the gels until a calibration normal force of 0.04 N was achieved. Following, an oscillatory shear-stress sweep test (0.6-10.0 Pa, 1.0 Hz, 25° C.) was applied to hydrogels of each collagen to HA ratio (2:1, 3:1, 4:1). This experiment was repeated in triplicate for each condition. Average values for storage and shear loss moduli, G' and G" respectively, were determined for each condition.

Bioprinting

An Allevi 2 bioprinter (Allevi, Philadelphia, Pa.) with 28G blunt end needle was used for printability testing and liver model printing. Previous to any printing, bioink solutions were combined and allowed to rest on ice for 45 minutes. A single bioink layer was extruded at 4 kPa pressure with a speed of 50 mm/s in a four spoke shape created via 3D software. Printability testing was performed using bioinks without cells and printed onto 5 cm tissue culture plastic dishes and then imaged, after which measurements for quantification were taken using ImageJ software. Liver model printing was performed in 6-well tissue culture plastic plates with a thin polydimethylsiloxane (PDMS) coating to prevent cell outgrowth onto plastic substrates. All printed structures were crosslinked using UV irradiation immediately after printing for 10 seconds with UV light being passed over the entire structure during that time.

Lx2 and aHSC Stellate Cell Culture

A human hepatic stellate cell line (Lx2) and primary fetal activated hepatic stellate cells (aHSC) were independently cultured on tissue culture plastic plates and used between passages 7 and 10 for experimentation[25-27]. Both cell types were expanded until reaching 70-80% confluency in Dulbecco's Modified Eagle Medium with 10% fetal bovine serum and 200 u/mL penicillin and streptomycin (DMEM-10) (Gibco, Gaithersburg, Md.). Cells were then retrieved from culture for bioink experiments using 0.05% Trypsin-EDTA (ThermoFisher Scientic, Waltham, Mass.) [27]. For bioink cultures, constructs were made using Lx2 or aHSCs at 5 million cells/mL. Cells were combined with bioink and 10 μL droplets of cell-gel solution were individually deposited into 48-well plastic plates that had been previously coated in a thin layer of PDMS. Constructs were sustained for 7 days with media changes on days 3 and 6 with DMEM-10. On day 7 experimentation was concluded and constructs were sacrificed for LIVE/DEAD cell viability assay (ThermoFisher Scientic, Waltham, Mass.) and fixation for histological processing. In addition to collagen/HA bioink formulations, an HA/gelatin hydrogel (Hystem-HP, ESI BIO) was also used for cell culture as a baseline for viability comparisons, and was prepared according to the manufacturer's instructions.

Hepatocyte Cell Culture and Liver Model

Primary human hepatocytes (Triangle Research Labs, Morrisville, N.C.) were bioprinted for the study of functionality within the bioink. Hepatocytes were thawed from a frozen cryovial and re-suspended in 10 mL hepatocyte complete media (HCM) (Lonza, Walkersville, Md.). Hepatocytes were counted, centrifuged, and re-suspended in 3:1 (collagen:HA) bioink at 5 million cells/mL. Four-spoke structures were printed using the same design as that of the printability testing and contained hepatocytes that were grown for 15 days. Printing was done at 4 kPa pressure with a speed of 50 mm/s in a single layer. On day 6, 100 mM acetaminophen (APAP) was added to two printed liver structures. Triplicate controls were maintained in parallel, and fresh media with or without APAP based on experimental group was refreshed every three days throughout the remainder of the experiment.

Viability Assays

LIVE/DEAD cell viability assays were performed using calcein AM and ethidium homodimer-1 reagents (1:500 each) in DPBS (ThermoFisher Scientific). Samples were incubated with the staining solution at 37° C. for 30 minutes after which they were washed and stored in DPBS before imaging on a Leica TCS LSI macro-confocal microscope (Leica, Wetzlar, Germany). Live and dead stained cells were counted manually and a ratio of live to dead cells was calculated for each cell condition. Cellular aspect ratios were calculated from thresholded LIVE/DEAD images using the Analyze Particles measurement in Fiji [28].

Histological Processing

Stellate cell tissue constructs and bioprinted liver structures were washed twice with DPBS and fixed with 4% paraformaldehyde for 1 hour then additionally washed twice with DPBS. Cultures were histologically processed, paraffin embedded, and sectioned at 5 μm thickness. Hemotoxylin and eosin (H&E) and picrosirus red staining was conducted on each of the stellate cell constructs conditions (ab150681, Abcam, San Francisco, Calif.), while H&E was conducted on bioprinted liver models. Images were captured on an Olympus BX63 brightfield microscope with picrosirus red images captured using polarized light.

Functionality Assays

Media aliquots were collected from liver models of n=2 or greater every 3 days for a total of 15 days in culture. Collected aliquots were stored at −80° C. until assays were performed. Human albumin (Abcam) and glutathione s-transferase alpha (alpha-GST, Oxford Biomedical Research, Rochester Hills, Mich.) ELISAs and a human urea (Abcam) colorimetric assay were performed following the manufacturers' instructions.

Statistical Analysis

Rheology testing was done with n=6 samples per conditions. A Student's t-test was employed to compare storage modulus and loss modulus between each of the materials previous to crosslinking (extrusion moduli) and after crosslinking as well as between each other. Bioprintability studies were done using n=8 samples per material condition. ANOVA was employed, to compare between each of the formulations. LIVE/DEAD viability assay groups were compared using Student's t-test, n=9 images (n=3 constructs, 3 images per construct). Hepatocyte structures were n=3 for untreated conditions and n=2 for APAP treated conditions. Student's t-test was used for comparison of each condition at each time point.

RESULTS

Physical Characterization

Figure 14:
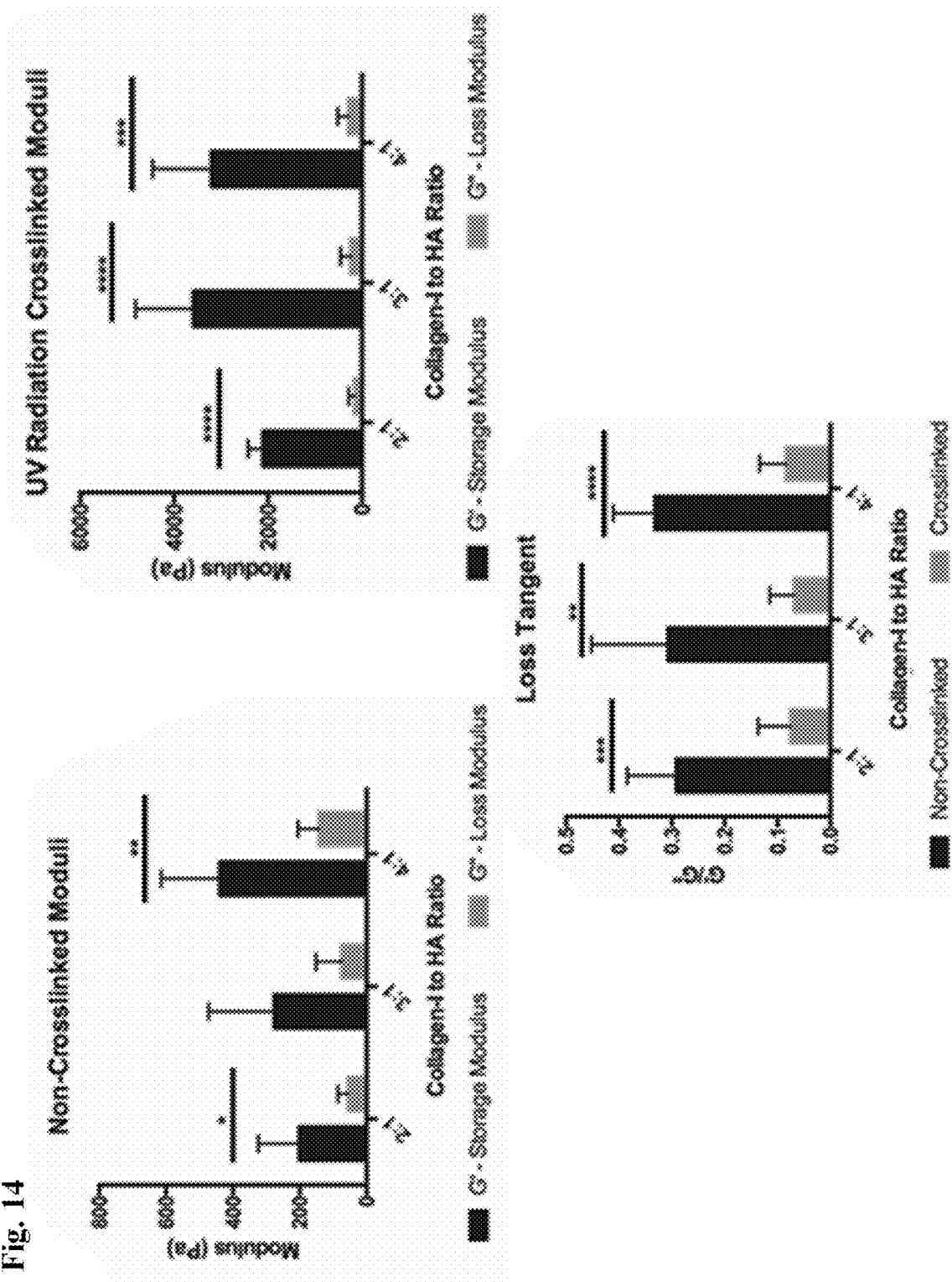
FIG. 14 shows graphs that characterize each bioink. G' and G" were measured for each formulation before crosslinking (left graph) and after printing and UV radiation crosslinking (middle graph). Loss tangents (G'/G") can be used as a measure of printability and were calculated for each formulation before and after crosslinking (right graph). Student's T-tests were performed to compare shear storage moduli between the non-crosslinked and crosslinked conditions for each biomaterial condition, non-crosslinked conditions were significantly different than the crosslinked conditions (p<0.005). *: p<0.05, : p<0.01, *: p<0.005, ****: p<0.001

Characterization of the bioink compositions; COL I:HA 2:1, 3:1, and 4:1, was performed via shear storage and loss moduli measurements before and after UV exposure to induce crosslinking (FIG. 14). The shear storage modulus (G') represents the elastic component of a material and specifically measures the stored energy of the material. The shear loss modulus (G") represents the viscous component of the material and measures the energy released from the material. These properties are important for biomaterials used for 3D printing because they determine the interplay between the ability of a material to flow versus to maintain its shape. Previously, it has been determined that materials with greater G' than G" are more printable than those with large G" components as long as the material remains able to flow. To determine if a material is applicable for bioprinting, the loss tangent is used which is calculated as G"/G'[29]. Materials are more elastic as the loss tangent decreases and more viscous as it increases[29, 30]. Previously characterized commercial bioinks have loss tangents between 0.30 and 0.45 during printing and decrease to below 0.2 when crosslinked[31]. Since the biomaterial is first extruded and then crosslinked by UV light, we performed moduli measurements on each formulation before exposure to UV, in order to determine the physical characteristics as they would be printed, and after UV crosslinking. However, it should be noted that given the nature of the thiolated HA and methacrylated collagen, some pH-driven crosslinking may occur spontaneously. Bioinks were left on ice for 45 minutes prior to testing in order to allow for any linking driven by thiol-methacrylate reactions. All three formulations show a greater storage modulus in comparison to loss modulus but appropriately balance each other by yielding loss tangents between 0.29 and 0.33 (FIG. 14). After UV mediated crosslinking of the materials, the shear storage modulus (G') is increased significantly across all conditions when compared to uncrosslinked materials (p<0.005). The shear loss modulus however does not significantly change before and after UV crosslinking, and due to these changes, all loss tangents decreased below 0.1, indicating the material has become more elastic (FIG. 14). In the crosslinked form, each of the bioinks (2:1, 3:1, 4:1 COL I:HA) maintain their shape, are able to be grasped with forceps, and maintain integrity for an observed time of greater than 60 days in DPBS.

Printability Measures

Figure 15:
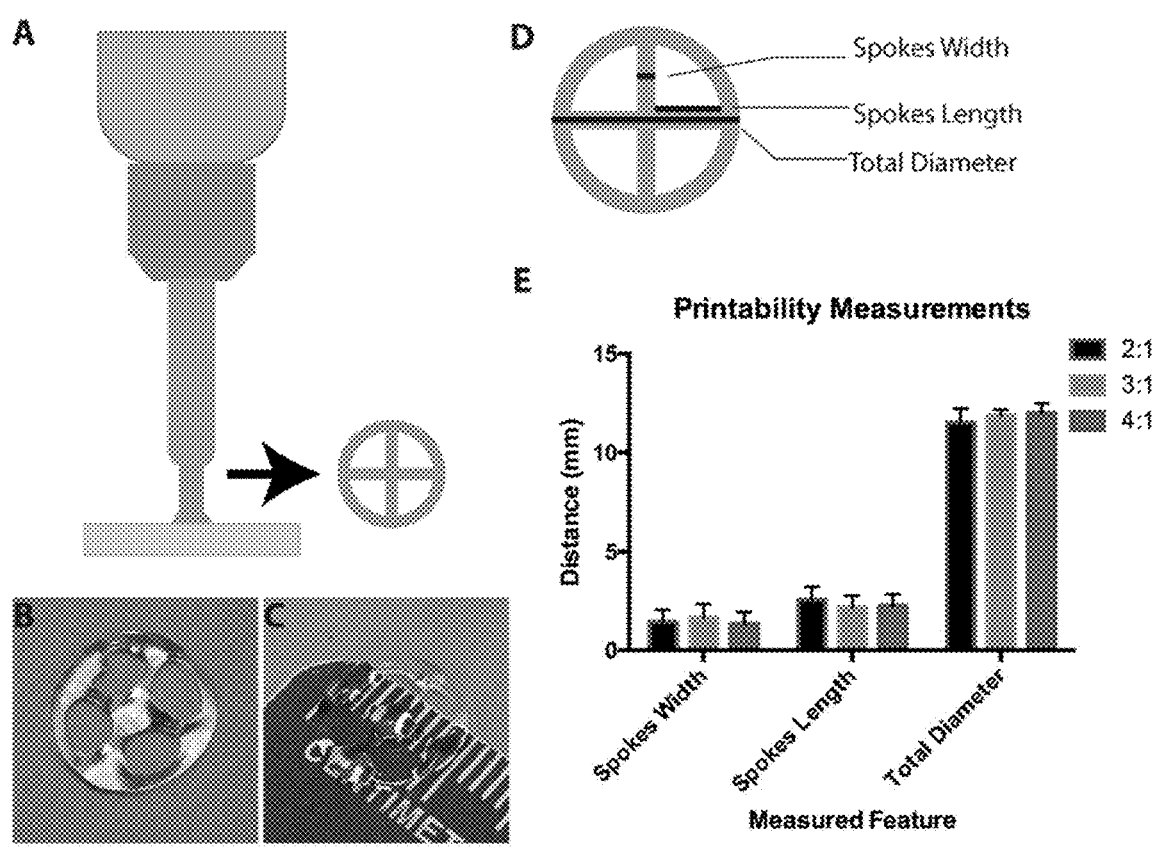
FIG. 15 shows hybrid bioink and printability characterization. A desktop extrusion bioprinter was used to print a 4-spoke wheel structure (panel A, printed structure in panels B and C). To assess the consistency of bioink printability, spoke width, spoke length, and wheel diameter (panel D) of printed structures were measured (panel E). All formulations displayed similar printability and consistency as there were no differences found in structure measurements between bioinks.

We assessed printability of each formulation by measuring stability of bioinks after mixing of COL I and HA and by printing a set structure using a benchtop extrusion bioprinter (FIG. 15, panels A-D). A 4-spoke structure was used to test the ability of the bioinks to form measurable structures in both straight and curved lines. Printing of each set of structures was conducted over a period of 45 minutes with 8 structures being produced for each bioink formulation (2:1, 3:1, 4:1 COL I:HA). Time included removal and replacement of plates. Each of the structures was immediately crosslinked after printing. For both the 2:1 and 3:1 mixtures, the printed material was visually homogenous throughout the 30-minute printing duration. Printability of bioinks extended to approximately 45 minutes within the bioprinter. The 4:1 mixture displayed visual phase separation after 30 minutes. Overall consistency of each of the printed structures following UV exposure was assessed by measuring the diameter in two locations, the arm length and width of all 4 arms (4 measurements per structure) (FIG. 15, panel E). Within the 30-minute printing period, each of the bioink mixtures appear to produce similar structures and there were no statistically significant differences found.

Cell Viability and Collagen Characterization

Figure 16:
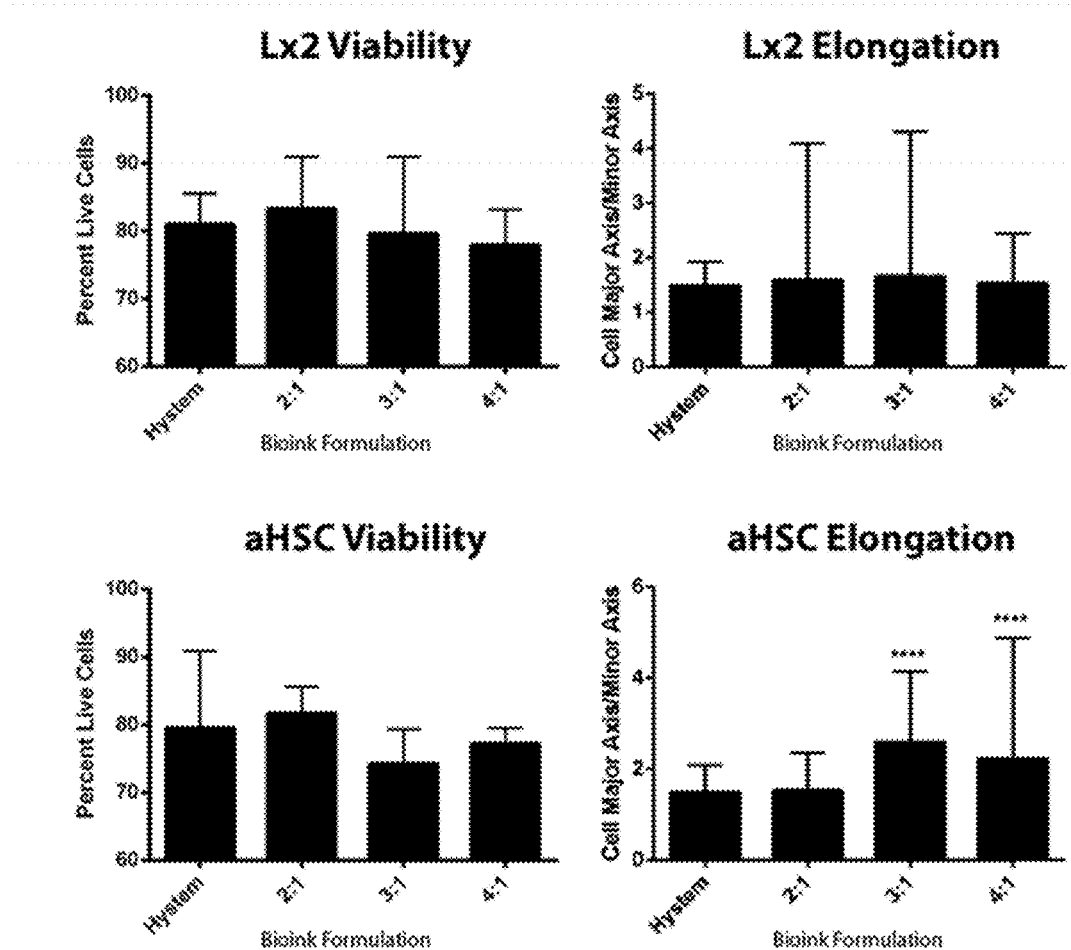
FIG. 16 shows bioink biocompatibility and viability analysis. To assess the biocompatibility of bioink formulations, a Live/Dead assay was performed using Lx2 and aHSC cells. Representative images were taken of stained Lx2 cells as well as stained aHSCs in all three bioink formulations as well as a commercially available hyaluronic acid-gelatin hydrogel. Images were then manually quantified to determine percentage of lives cells for comparison of overall viability of Lx2 cells (top left graph) and aHSCs (bottom left graph). No differences were found in cell viability between bioink formulations. Morphological differences were quantified by measuring cellular aspect ratio (major axis/minor axis) for each condition (top right graph and bottom right graph). ****: p<0.001 vs Hystem.

Bioprinting is intended for creating supportive microenvironments that should facilitate cell viability and function. LIVE/DEAD assays were conducted to determine biocompatibility of each bioink mixture, and that of a commercially available hydrogel comprised of HA and gelatin[32, 33]. Lx2 and aHSCs are hepatic stellate cells and were chosen in order to test their ability to interact with their microenvironment and the extracellular matrix [34]. Both of the cell types were grown in each of the four formulations (HA/gelatin, 2:1, 3:1, 4:1 COL I:HA) for 7 days and a LIVE/DEAD cell viability assay was performed. The stained structures were imaged using macro-confocal microscopy and the percentage of viable cells in each condition was calculated using manual cell counts from each image collected for each of the conditions. We observed >80% of viable cells for each of the formulations, indicating that all were able to support cell viability (FIG. 16). The microscope images additionally show cell/matrix interactions of the activated stellate cells vs. the more naive Lx2 cells [34, 35]. Interestingly, the 3:1 and 4:1 formulations induced more pronounced cell shape changes in aHSCs, suggesting that an increase in COL I supports better cell-matrix attachments and cell spreading. Quantification of cell aspect ratio (FIG. 16) support this observation as aHSCs in the 3:1 and 4:1 formulation display higher aspect ratios, or more elongation, when compared to HA/gelatin culture conditions. No differences in aspect ratio were measured in Lx2 cells. To further assess cell-matrix interaction we performed H&E and Picrosirus Red (PSR) staining of the printed constructs. Lx2 cells behave similarly in all bioink formulations as well as the commercial HA/gelatin hydrogel with all cells forming aggregates which do not appear to be remodeling or interacting with the surrounding collagen. Conversely, aHSCs exhibit elongation within the collagen based bioinks (3:1 and 4:1) which further indicates an increase in cell-matrix interaction with cultures including these cells. Additionally, PSR staining was used to characterize collagen remodeling (fiber bundling) in these structures. Red and orange signal denotes bundled collagen, which can be observed around cells in all bioink formulations but is absent in the HA/gelatin samples.

Liver Model

Figure 17:
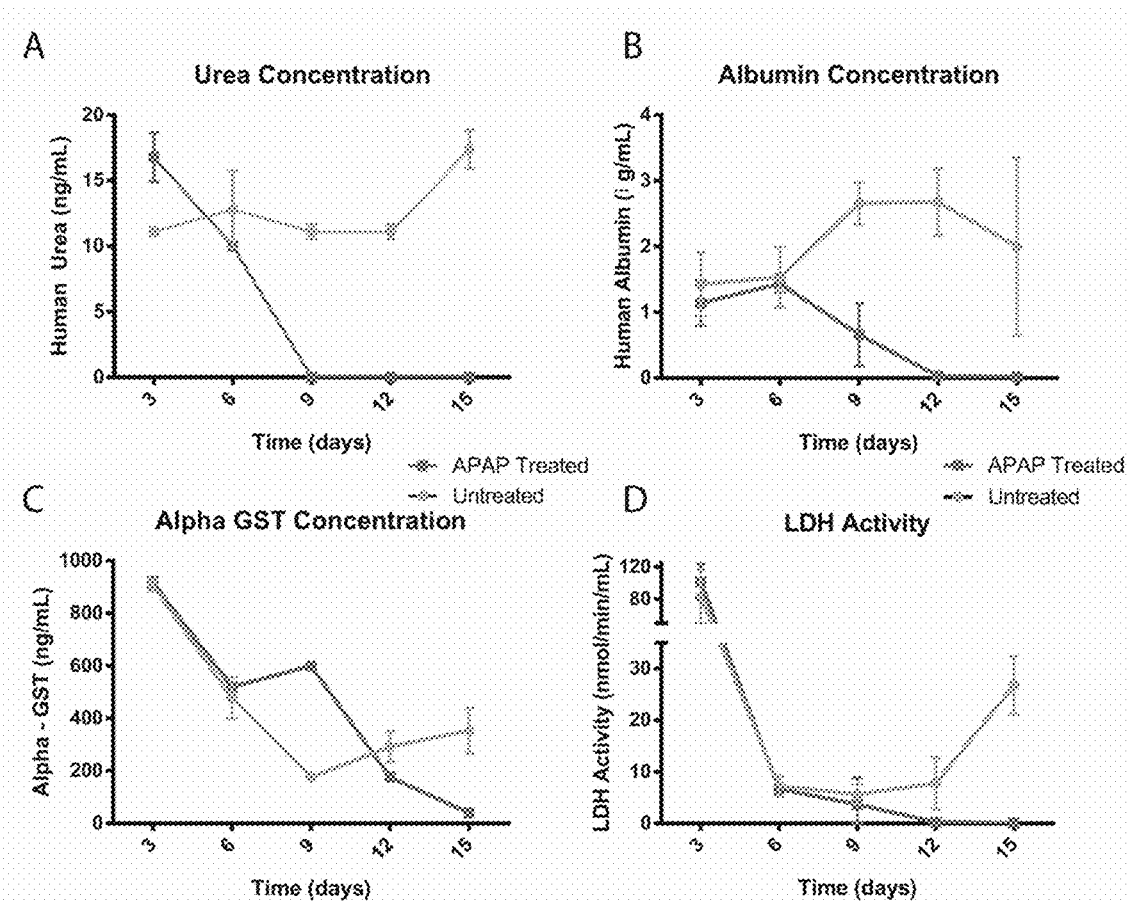
FIG. 17 shows hepatocyte functionality with and without APAP treatment. To assess the overall functionality of liver organoids, urea (panel A), albumin (panel B), α-GST (panel C), and lactic acid dehydrogenase (LDH) (panel D) were measured over time with and without APAP treatment, arrows denote time of treatment.

Hepatocytes are integral for liver function and make up approximately 80% of the entire liver to carry out metabolic and detoxifying activities. Hepatocytes, although well characterized, can be challenging to grow in vitro and have low viability and minimal function if not cultured in the correct environment. Current in vitro techniques for use of hepatocytes in drug toxicity testing and metabolomics are primarily seeding hepatocytes on COL I gels, which maintain cell viability for a limited time [22, 36-38]. Bioprinting hepatocytes in 3D structures offers a novel platform for in vitro culture and testing of hepatocyte function and response. To determine viability and functionality of hepatocytes within the bioink, they were bioprinted in the 3:1 COL I to HA formulation. The 3:1 bioink formulation was utilized as it contained a high concentration of collagen while maintaining consistent printability. Bioprinted constructs were maintained in culture for 6 days and subsequently, hepatocyte functionality was determined by exposing the constructs to an hepatic toxicant, acetaminophen (APAP, 100 µM) and measuring the levels of albumin, urea, α-GST, and lactic acid dehydrogenase (LDH) in the media over time. Significant decreases in both urea and albumin levels were observed at day 9 and continued to decrease through day 15 for the APAP treated conditions, compared with stable levels in the untreated constructs (FIG. 17, panels A-B). Interestingly, the levels of α-GST, a detoxification protein, increased at day 9, 3 days post APAP addition, but subsequently decreases by day 12, likely due to cell death (FIG. 17, panel C). The high levels of α-GST after 3 days in culture, and prior to drug addition, may be due to cell-stress experienced during the printing procedure that led to upregulation of α-GST expression. In addition, levels of LDH, a marker of liver damage, also peak due to printing-related stress, but fall to nominal levels by day 6. APAP treated constructs demonstrate decreasing LDH activity, again likely due to toxicity related cell death. Untreated conditions maintain steady LDH until day 15 when levels begin to increase. Increases in LDH and α-GST at day 15 indicates this period may be nearing the culture limit, however LIVE/DEAD assay was conducted and cultures remained viable. Taken together, these results demonstrate appropriate response to a well-known and characterized liver toxin, indicating the bioink is sufficient to both maintain hepatocyte viability and support physiologic response to drugs. Histological staining (H&E) demonstrated greater cellularity in untreated constructs, while drug-treated conditions show loss of cellularity (FIG. 17, panel D).

DISCUSSION

Bioprinting has made substantial advances in the past two decades, however biomaterials ideal for both printing and development of cellular microenvironments have been limited[8]. By preparing hybrid bioinks, printability can be improved using physiologically relevant materials that cells will recognize as actual extracellular matrix rather than inert or synthetic alternatives. A current limitation to most commercial bioinks is that they are lacking in true extracellular matrix-like components. This can prevent cells from recognizing and interacting with their microenvironment as well as restrict the development of in vivo-like tissues and morphologies. In this study, methacrylated COL I was combined with thiolated hyaluronic acid to produce a bioink that is both easy to use for bioprinting and supports cellular viability and function. These properties were then deployed to biofabricate a simple in vitro human liver model yielding satisfactory functionality.

Printability was determined through rheological and printed structure measurements. By measuring loss and storage moduli previous to and after UV radiation crosslinking and further calculating the loss tangent, it was shown that each of the materials (2:1, 3:1, 4:1 COL I:HA) exhibited the same mechanical properties. All formulations had greater fluid than elastic features previous to crosslinking. This indicates that each of the materials was able to flow in the viscous/liquid phase. Yet, because the storage modulus component was high enough, the bioink could hold its shape for a period of time following printing, prior to UV crosslinking. After crosslinking, the loss modulus was decreased for each of the materials and the storage modulus was significantly increased. This change indicates the transition from a liquid that is able to flow to a material that is able to maintain its shape permanently and was observed for each of the materials. Printability testing was additionally conducted on each of the three materials to determine which would be ideal for printing. While each of the three was able to print structures of the appropriate shape with minimal variation for 30 minutes or more, it was found that at room temperature the 4:1 bioink began phase separating and was no longer homogenous, with collagen bundles forming in solution. Separation of the bioink was a major consideration when determining the ideal bioink for liver microenvironment printing. From determining the moduli and conducting printability testing on each of the bioinks, it was determined that each of the bioinks behaved the same and no significant differences were measured. However, longevity of printing is limited with the 4:1 formulation, which reduces its utility as a bioink. While not wishing to be bound to any particular theory, due to the greater amount of COL I within the formulation, collagen is likely limited in its interaction with HA and instead primarily interacts with itself, at room temperature this quickly leads to bundling of the collagen within the bioink.

Cell viability and characterization of collagen within the bioinks was further studied to determine which would be most ideal for cells. Using LIVE/DEAD cell viability assays, it was shown that each of the bioinks was able to adequately support cells compared to other commercial, previously characterized hydrogels. It was found that each of the bioinks (2:1, 3:1, 4:1 COL I:HA) maintained high cellular viability and were comparable to other 3D biomaterials. Although no differences in viability were measured, LIVE/DEAD cell viability assay images indicated differences in cell morphology. HA/gelatin samples elicited no elongation from aHSCs or Lx2 cells—both of which are characterized by their ability to interact with their microenvironment—and cells tended to favor cell-cell interactions in this hydrogel[39]. An increase in collagen content increased elongation of aHSCs. Collagen presence and bundling was shown through utilization of picrosirus red staining and polarized light imaging. No significant differences were found between each of the bioinks. Although the 4:1 bioink was shown to be most ideal for cell elongation as demonstrated in the LIVE/DEAD, H&E, and picrosirus red staining images, it was previously shown to be problematic for printing itself Therefore, the 3:1 bioink was used for printed liver microenvironments as it provided a greater amount of collagen to create physiological relevance and remained printable for a workable period of time.

To show a potential application of this bioink system, liver constructs containing primary human hepatocytes and liver stellate cells were bioprinted and employed in a straightforward drug toxicity test. Acetaminophen (APAP) is a widely used pain reliever that is well documented to cause liver damage upon overdosing and has been used as a test compound in other tissue engineered liver organoid studies [40]. Liver constructs were bioprinted using the 3:1 COL I to HA bioink. Additional printed structures were treated with APAP to show loss of function in comparison to healthy, untreated structures. Functionality was maintained for two weeks indicating the extrusion 3D bioprinting process with the bioink did not adversely affect cells. The liver model we developed acts as a simple microenvironment to support hepatocytes allowing for functionality levels previously seen in literature, likely due to the more physiologic environment[41].

The development of a simple bioink that is printable and contains physiologic components advances the state of bioprinting in that it allows researchers to modulate 3D matrices for their desired application. For a balance in both printability and collagen content, the 3:1 COL I to HA bioink was selected. To demonstrate properties of the bioink, a liver model was used, however, other organ systems can be modeled with such a biomaterial as collagen concentration can be tuned to the tissue of interest. The use of methacrylated and thiolated base materials allows for addition of functionalized proteins or molecules to further customize the bioink for specific applications. Simple modifications such as the addition of laminin or fibronectin can jump-start cellular adhesion or drive biochemical pathway activation. Certain disease phenotypes such as cancer or fibrosis are typified by changes in elastin and fibronectin levels which can be simulated through additions to the bioink backbone [42]. Because crosslinking is controlled through UV radiation, zones of different bioink formulations can be deposited in serial layers to simulate the varied layers of a physiologic tissue. For instance, a layer of elastin-functionalized COL I and -III bioink could be deposited and crosslinked to represent a dermal layer of skin upon which a laminin-enriched layer of collagen-IV bioink could be printed as the basement membrane of the epidermis[43]. Similar layered structures could be produced to represent colonic submucosa and epithelium or the layers of blood vessels. However, the bioink is still limited by its loss of homogeneity over time and its temperature sensitivity, and thus is restricted in the complexity of geometries and structures that can be printed. In addition, the uncrosslinked bioink has a low viscosity and relies on rapid UV-driven crosslinking to hold a printed shape. Low viscosity is also limiting in which shapes and structures can be printed as multilayer structures have not yet been achieved. Given these properties, the bioink will be difficult to use for high resolution or high aspect printing. The problems associated with low viscosity can be mitigated by adding thickening agents to the formulation, but other hydrogel parameters may change as a result.

Conclusively, by combining methacrylated COL I with thiolated HA and UV crosslinker, a bioink that is both printable and physiologically relevant has been developed. The bioink is fluid enough to be printed and elastic enough to maintain its shape while also being advantageous for cell viability and interaction. Three bioink formulations were created and tested to determine ideal parameters for a 3D bioprinted liver model. Each of the formulations appeared to facilitate cell viability matching currently used biomatrices and some were shown to allow cell elongation. A 3:1 COL I to HA ratio was determined to be most ideal for printing and was utilized for the printing of the liver microenvironments. Using the bioink, structures containing primary human hepatocytes were printed and monitored over the course of 2 weeks during which time they were able to maintain urea and albumin production and responded appropriately to APAP. Such a bioink allows for modulation of collagen and hyaluronic acid as well as creating the opportunity for additional proteins and ECM components to be added. This collagen and HA hybrid bioink formulation may be used to build on additional functionality, to biofabricate a variety of tissue types for applications ranging from in vitro drug screens, disease modeling, and for biomanufacturing of tissue products for human use.

REFERENCES

[1] M. Mills, M. K. Estes, Physiologically relevant human tissue models for infectious diseases, Drug Discov Today 21(9) (2016) 1540-52.
[2] M. A. Lancaster, J. A. Knoblich, Organogenesis in a dish: modeling development and disease using organoid technologies, Science 345(6194) (2014) 1247125.
[3] A. Skardal, T. Shupe, A. Atala, Organoid-on-a-chip and body-on-a-chip systems for drug screening and disease modeling, Drug Discov Today 21(9) (2016) 1399-1411.
[4] F. Pampaloni, E. G. Reynaud, E. H. Stelzer, The third dimension bridges the gap between cell culture and live tissue, Nature reviews. Molecular cell biology 8(10) (2007) 839-45.
[5] H. N. Chia, B. M. Wu, Recent advances in 3D printing of biomaterials, J Biol Eng 9 (2015) 4.
[6] W. Liu, Y. S. Zhang, M. A. Heinrich, F. De Ferrari, H. L. Jang, S. M. Bakht, M. M. Alvarez, J. Yang, Y. C. Li, G. Trujillo-de Santiago, A. K. Miri, K. Zhu, P. Khoshakhlagh, G. Prakash, H. Cheng, X. Guan, Z. Zhong, J. Ju, G. H. Zhu, X. Jin, S. R. Shin, M. R. Dokmeci, A. Khademhosseini, Rapid Continuous Multimaterial Extrusion Bioprinting, Adv Mater 29(3) (2017).
[7] S. V. Murphy, A. Atala, 3D bioprinting of tissues and organs, Nat Biotechnol 32(8) (2014) 773-85.
[8] S. V. Murphy, A. Skardal, A. Atala, Evaluation of hydrogels for bio-printing applications, J Biomed Mater Res A 101(1) (2013) 272-84.
[9] M. Hospodiuk, M. Dey, D. Sosnoski, I. T. Ozbolat, The bioink: A comprehensive review on bioprintable materials, Biotechnol Adv 35(2) (2017) 217-239.
[10] E. M. Ahmed, Hydrogel: Preparation, characterization, and applications: A review, J Adv Res 6(2) (2015) 105-21.
[11] C. B. Highley, G. D. Prestwich, J. A. Burdick, Recent advances in hyaluronic acid hydrogels for biomedical applications, Curr Opin Biotechnol 40 (2016) 35-40.
[12] A. Skardal, A. Atala, Biomaterials for integration with 3-d bioprinting, Ann Biomed Eng 43(3) (2015) 730-46.
[13] L. M. Delgado, Y. Bayon, A. Pandit, D. I. Zeugolis, To cross-link or not to cross-link? Cross-linking associated foreign body response of collagen-based devices, Tissue Eng Part B Rev 21(3) (2015) 298-313.
[14] L. Ouyang, C. B. Highley, W. Sun, J. A. Burdick, A Generalizable Strategy for the 3D Bioprinting of Hydrogels from Nonviscous Photo-crosslinkable Inks, Adv Mater 29(8) (2017).
[15] M. Ehrbar, A. Sala, P. Lienemann, A. Ranga, K. Mosiewicz, A. Bittermann, S. C. Rizzi, F. E. Weber, M. P. Lutolf, Elucidating the role of matrix stiffness in 3D cell migration and remodeling, Biophys J 100(2) (2011) 284-93.
[16] M. Devarasetty, E. Wang, S. Soker, A. Skardal, Mesenchymal stem cells support growth and organization of host-liver colorectal-tumor organoids and possibly resistance to chemotherapy, Biofabrication 9(2) (2017) 021002.
[17] A. Skardal, M. Devarasetty, C. Rodman, A. Atala, S. Soker, Liver-Tumor Hybrid Organoids for Modeling Tumor Growth and Drug Response In Vitro, Ann Biomed Eng 43(10) (2015) 2361-73.
[18] M. B. Esch, J. M. Prot, Y. I. Wang, P. Miller, J. R. Llamas-Vidales, B. A. Naughton, D. R. Applegate, M. L. Shuler, Multi-cellular 3D human primary liver cell culture elevates metabolic activity under fluidic flow, Lab Chip 15(10) (2015) 2269-77.
[19] K. Wrzesinski, A. Rogowska-Wrzesinska, R. Kanlaya, K. Borkowski, V. Schwammle, J. Dai, K. E. Joensen, K. Wojdyla, V. B. Carvalho, S. J. Fey, The cultural divide: exponential growth in classical 2D and metabolic equilibrium in 3D environments, PloS one 9(9) (2014) e106973.
[20] J. Lee, M. J. Cuddihy, G. M. Cater, N. A. Kotov, Engineering liver tissue spheroids with inverted colloidal crystal scaffolds, Biomaterials 30(27) (2009) 4687-94.
[21] P. Godoy, N. J. Hewitt, U. Albrecht, M. E. Andersen, N. Ansari, S. Bhattacharya, J. G. Bode, J. Bolleyn, C. Borner, J. Bottger, A. Braeuning, R. A. Budinsky, B. Burkhardt, N. R. Cameron, G. Camussi, C. S. Cho, Y. J. Choi, J. Craig Rowlands, U. Dahmen, G. Damm, O. Dirsch, M. T. Donato, J. Dong, S. Dooley, D. Drasdo, R. Eakins, K. S. Ferreira, V. Fonsato, J. Fraczek, R. Gebhardt, A. Gibson, M. Glanemann, C. E. Goldring, M. J. Gomez-Lechon, G. M. Groothuis, L. Gustaysson, C. Guyot, D. Hallifax, S. Hammad, A. Hayward, D. Haussinger, C. Hellerbrand, P. Hewitt, S. Hoehme, H. G. Holzhutter, J. B. Houston, J. Hrach, K. Ito, H. Jaeschke, V. Keitel, J. M. Kelm, B. Kevin Park, C. Kordes, G. A. Kullak-Ublick, E. L. LeCluyse, P. Lu, J. Luebke-Wheeler, A. Lutz, D. J. Maltman, M. Matz-Soja, P. McMullen, I. Merfort, S. Messner, C. Meyer, J. Mwinyi, D. J. Naisbitt, A. K. Nussler, P. Olinga, F. Pampaloni, J. Pi, L. Pluta, S. A. Przyborski, A. Ramachandran, V. Rogiers, C. Rowe, C.

Schelcher, K. Schmich, M. Schwarz, B. Singh, E. H. Stelzer, B. Stieger, R. Stober, Y. Sugiyama, C. Tetta, W. E. Thasler, T. Vanhaecke, M. Vinken, T. S. Weiss, A. Widera, C. G. Woods, J. J. Xu, K. M. Yarborough, J. G. Hengstler, Recent advances in 2D and 3D in vitro systems using primary hepatocytes, alternative hepatocyte sources and non-parenchymal liver cells and their use in investigating mechanisms of hepatotoxicity, cell signaling and ADME, Arch Toxicol 87(8) (2013) 1315-530.

[22] D. Yip, C. H. Cho, A multicellular 3D heterospheroid model of liver tumor and stromal cells in collagen gel for anti-cancer drug testing, Biochem Biophys Res Commun 433(3) (2013) 327-32.

[23] M. J. Powers, K. Domansky, M. R. Kaazempur-Mofrad, A. Kalezi, A. Capitano, A. Upadhyaya, P. Kurzawski, K. E. Wack, D. B. Stolz, R. Kamm, L. G. Griffith, A microfabricated array bioreactor for perfused 3D liver culture, Biotechnol Bioeng 78(3) (2002) 257-69.

[24] D. Yoon No, K. H. Lee, J. Lee, S. H. Lee, 3D liver models on a microplatform: well-defined culture, engineering of liver tissue and liver-on-a-chip, Lab Chip 15(19) (2015) 3822-37.

[25] R. G. Ruddell, F. Oakley, Z. Hussain, I. Yeung, L. J. Bryan-Lluka, G. A. Ramm, D. A. Mann, A role for serotonin (5-HT) in hepatic stellate cell function and liver fibrosis, Am J Pathol 169(3) (2006) 861-76.

[26] C. Coulouarn, A. Corlu, D. Glaise, I. Guenon, S. S. Thorgeirsson, B. Clement, Hepatocyte-stellate cell cross-talk in the liver engenders a permissive inflammatory microenvironment that drives progression in hepatocellular carcinoma, Cancer Res 72(10) (2012) 2533-42.

[27] L. Xu, A. Y. Hui, E. Albanis, M. J. Arthur, S. M. O'Byrne, W. S. Blaner, P. Mukherjee, S. L. Friedman, F. J. Eng, Human hepatic stellate cell lines, LX-1 and LX-2: new tools for analysis of hepatic fibrosis, Gut 54(1) (2005) 142-51.

[28] J. Schindelin, I. Arganda-Carreras, E. Frise, V. Kaynig, M. Longair, T. Pietzsch, S. Preibisch, C. Rueden, S. Saalfeld, B. Schmid, J.-Y. Tinevez, D. J. White, V. Hartenstein, K. Eliceiri, P. Tomancak, A. Cardona, Fiji: an open-source platform for biological-image analysis, Nature Methods 9 (2012) 676.

[29] M. Bartnikowski, R. M. Wellard, M. Woodruff, T. Klein, Tailoring Hydrogel Viscoelasticity with Physical and Chemical Crosslinking, Polymers 7(12) (2015) 19.

[30] D. J. Munoz-Pinto, A. C. Jimenez-Vergara, T. P. Gharat, M. S. Hahn, Characterization of sequential collagen-poly (ethylene glycol) diacrylate interpenetrating networks and initial assessment of their potential for vascular tissue engineering, Biomaterials 40 (2015) 32-42.

[31] K. C. Hung, C. S. Tseng, L. G. Dai, S. H. Hsu, Water-based polyurethane 3D printed scaffolds with controlled release function for customized cartilage tissue engineering, Biomaterials 83 (2016) 156-68.

[32] A. Skardal, J. Zhang, L. McCoard, X. Xu, S. Oottamasathien, G. D. Prestwich, Photocrosslinkable hyaluronan-gelatin hydrogels for two-step bioprinting, Tissue Eng Part A 16(8) (2010) 2675-85.

[33] G. Camci-Unal, D. Cuttica, N. Annabi, D. Demarchi, A. Khademhosseini, Synthesis and characterization of hybrid hyaluronic acid-gelatin hydrogels, Biomacromolecules 14(4) (2013) 1085-92.

[34] I. Mederacke, C. C. Hsu, J. S. Troeger, P. Huebener, X. Mu, D. H. Dapito, J. P. Pradere, R. F. Schwabe, Fate tracing reveals hepatic stellate cells as dominant contributors to liver fibrosis independent of its aetiology, Nat Commun 4 (2013) 2823.

[35] I. Mederacke, D. H. Dapito, S. Affo, H. Uchinami, R. F. Schwabe, High-yield and high-purity isolation of hepatic stellate cells from normal and fibrotic mouse livers, Nat Protoc 10(2) (2015) 305-15.

[36] C. C. Bell, D. F. Hendriks, S. M. Moro, E. Ellis, J. Walsh, A. Renblom, L. Fredriksson Puigvert, A. C. Dankers, F. Jacobs, J. Snoeys, R. L. Sison-Young, R. E. Jenkins, A. Nordling, S. Mkrtchian, B. K. Park, N. R. Kitteringham, C. E. Goldring, V. M. Lauschke, M. Ingelman-Sundberg, Characterization of primary human hepatocyte spheroids as a model system for drug-induced liver injury, liver function and disease, Sci Rep 6 (2016) 25187.

[37] N. S. Bhise, V. Manoharan, S. Massa, A. Tamayol, M. Ghaderi, M. Miscuglio, Q. Lang, Y. Shrike Zhang, S. R. Shin, G. Calzone, N. Annabi, T. D. Shupe, C. E. Bishop, A. Atala, M. R. Dokmeci, A. Khademhosseini, A liver-on-a-chip platform with bioprinted hepatic spheroids, Biofabrication 8(1) (2016) 014101.

[38] A. Skardal, S. V. Murphy, M. Devarasetty, I. Mead, H.-W. Kang, Y.-J. Seol, Y. Shrike Zhang, S.-R. Shin, L. Zhao, J. Aleman, A. R. Hall, T. D. Shupe, A. Kleensang, M. R. Dokmeci, S. Jin Lee, J. D. Jackson, J. J. Yoo, T. Hartung, A. Khademhosseini, S. Soker, C. E. Bishop, A. Atala, Multi-tissue interactions in an integrated three-tissue organ-on-a-chip platform, Scientific Reports 7(1) (2017) 8837.

[39] N. Lin, Z. Chen, Y. Lu, Y. Li, K. Hu, R. Xu, Role of activated hepatic stellate cells in proliferation and metastasis of hepatocellular carcinoma, Hepatol Res 45(3) (2015) 326-36.

[40] A. Skardal, S. V. Murphy, M. Devarasetty, I. Mead, H. W. Kang, Y. J. Seol, Y. Shrike Zhang, S. R. Shin, L. Zhao, J. Aleman, A. R. Hall, T. D. Shupe, A. Kleensang, M. R. Dokmeci, S. Jin Lee, J. D. Jackson, J. J. Yoo, T. Hartung, A. Khademhosseini, S. Soker, C. E. Bishop, A. Atala, Multi-tissue interactions in an integrated three-tissue organ-on-a-chip platform, Sci Rep 7(1) (2017) 8837.

[41] A. Skardal, M. Devarasetty, S. Soker, A. R. Hall, In situ patterned micro 3D liver constructs for parallel toxicology testing in a fluidic device, Biofabrication 7(3) (2015) 031001.

[42] C. Frantz, K. M. Stewart, V. M. Weaver, The extracellular matrix at a glance, Journal of cell science 123(24) (2010) 4195-4200.

[43] P. Briquez, J. A. Hubbell, M. Martino, Extracellular Matrix-Inspired Growth Factor Delivery Systems for Skin Wound Healing, 2015.

Example 9

The purpose of the present study was to develop well-defined hydrogel biomaterials suitable for fabrication of functional hydrogel supported hepatic tissue constructs, or hepatic organoids, that can be employed in drug testing, thereby improving existing models, and that can readily be translated for clinical use (e.g., in liver failure patients). Hydrogel formulations were designed with emphasis on the critical liver ECM constituents and simple fabrication and composition, and were subsequently evaluated for biocompatibility using different cell lines. The hyaluronic acid and collagen formulation modified with fibronectin which best fulfilled the desired characteristics was then utilized to engineer functional hydrogel supported hepatic tissue constructs, composed of human hepatocytes and hepatic stellate cells, and their response to FDA-recalled drugs, approved drugs with known hepatotoxicity, and environmental toxins was assessed.

2. EXPERIMENTAL METHODS

2.1. Gel Formulations

Initially, two different gel formulations were created. One of the formulation was comprised of thiolated and heparinized hyaluronic acid (Heprasil®), thiolated gelatin (Gelin-S®), and thiol-reactive polyethylene glycol diacrylate (PEGDA) crosslinker (Extralink®, MW=3.4 kDa; all from HyStem-HP hydrogel kit; ESI-BIO, Alameda, Calif.) were dissolved in 0.5% w/v solution of photoinitiator (4-(2-hydroxyethoxy) phenyl-(2-propyl) ketone; Sigma-Aldrich, St. Louis, Mo.) to make 1% w/v solutions. This hydrogel was finally comprised of hyaluronic acid, gelatin, and PEGDA mixed at a ratio of 1:1:0.5, in which the thiol groups on the hyaluronic acid and gelatin are crosslinked using the PEGDA acrylate groups. For the second formulation—the test formulation—methacrylated collagen type I (Advanced BioMatrix, Carlsbad, Calif.) was reconstituted with 20 mM acetic acid according to the manufacturer's protocol to produce a concentration of 6 mg/mL Immediately prior to use, 1 mL collagen was neutralized with 85 µl of neutralization buffer (Advanced BioMatrix). The final collagen formulation was composed of methacrylated collagen and thiolated and heparinized hyaluronic acid (Heprasil®) at a ratio of 1:3, with thiolated fibronectin (synthetic modification described below) added for a final concentration of 0.25 µg/mL, in which the methacrylate groups on the collagen proteins covalently bond to the thiol groups of the HA and fibronectin components.

2.2. Fibronectin Thiolation

The lyophilized human fibronectin protein (ThermoFisher, Waltham, Mass.) was dissolved into 1X DPBS pH 7.4 containing 10-mM EDTA for a final 1 mg/mL fibronectin solution. To the reaction mixture containing fibronectin (1 mg/mL), 50 mL of the 65-mM SATA (Sigma) dissolved in DMSO was immediately added and the solution and was allowed to react for 30 minutes at room temperature. The reaction mixture was dialyzed against 1X DPBS pH 7.4 containing 1-mM EDTA for 4-6 hours to remove unreacted SATA. After dialysis, 500 mL of a 0.5 M hydroxylamine in 1X DPBS pH 7.4 containing 25-mM EDTA was added to the reaction mixture and left undisturbed for 2 hours at room temperature. Then the reaction mixture was dialyzed against 1X DPBS pH 7.4 containing 1-mM EDTA overnight and the dialysis buffer was changed every 6-8 hours. Lastly, a buffer exchange with deionized water was done prior to lyophilizing to remove salts. After lyophilizing it was stored at −20° C. It is reconstituted in 1X DPBS pH 7 prior to use.

2.3. Cell Culture

Human liver cancer cell line (HepG2, HB-8065™; American Type Culture Collection (ATCC), Manassas, Va.), human glioblastoma cell line (U-87 MG, HTB-14™; ATCC, obtained from Cell and Viral Vector Laboratory Shared Resource of Wake Forest Baptist Medical Center), human colorectal cancer cell line (HCT 116, CCL-247™; ATCC), and human hepatic stellate cells (LX2, Millipore Sigma) were cultured in Dulbecco's Modified Eagle Medium—high glucose (4.5 g/L) (DMEM-HG; Lonza, Benicia, Calif.) supplemented with 10% fetal bovine serum (FBS; Hyclone, Logan, Utah), 0.5% L-glutamine (Hyclone) and 0.5% penicillin/streptomycin (P/S; Hyclone) at 37° C. with 5% $CO_2$. Cells were used at 90% confluence and passage five or less. Primary human hepatocytes lot number HUM4122A (Triangle Research Labs, Morrisville, N.C.) were directly used in experiments without prior expansion according to the manufacturer's protocol.

2.4. Cancer Cell Organoid Formation

The cells were trypsinized with 0.05% of trypsin (Hyclone) and counted. Tissue constructs of each model cell line (HepG2 [human hepatoma], U-87 MG [human glioblastoma], and HCT 116 [human colorectal carcinoma]) were created using fifty thousand cells of the respective cells and suspending them in either 10 µl of hyaluronic hydrogel formulation (hyaluronic acid, gelatin, and PEGDA) or in 10 µl of formulation of collagen gel (collagen, hyaluronic acid, and fibronectin), in order to verify that the collagen and fibronectin containing hydrogel showed equally sufficient viability as the commercially available formulation. We chose this cell density for cancer organoid formation based on the results obtained from 3D organoid research performed in our lab.[31] The gel- cell mixture was pipetted in a well of a 48-well plate (Corning, N.Y.) that was pre-coated with 200 µl of polydimethylsiloxane (PDMS; Sylgard 184 elastomer kit, Dow Corning, Midland, Mich.) prepared according to manufacturer's protocol. The organoids were then crosslinked with UV light (Dymax BlueWave 75, Torrington, Conn.) on a high-intensity setting for 3 seconds. The wells were filled with 500 µL of media, which was replenished on day 4 and day 7 of the experiment. The organoids were maintained in culture for 10 days.

2.5. Cell Viability and Proliferation Assays for the Cancer Organoids

Biocompatibility of the different gel formulations was assessed in human cancer cell and liver organoids on days 4, 7, and 10 (n=3) using a standard live/dead cell viability kit (Thermo Fisher, Waltham, Mass.) according to the manufacturer's recommendation. Stained organoids were imaged using macro-confocal microscopy (Leica TCS LSI, Leica Microsystems, Buffalo Grove, Ill.). Proliferation of cells within the different organoids was evaluated on days 4, 7, and 10 (n=3) by quantification of mitochondrial metabolism with a CellTiter 96® Aqueous One Solution Cell Proliferation Assay kit (Promega, Madison, Wis.) according to the manufacturer's protocol. Absorbance was quantified on a Spectramax M5 plate reader (Molecular Devices, Sunnyvale, Calif.) at 490 nm.

2.6. Liver Construct Formation

Cryopreserved primary human hepatocytes were thawed according to manufacturer's protocol and the cells were directly used in experiments. LX2 hepatic stellate cells were trypsinized with 0.05% of trypsin (Hyclone) and counted. Forty thousand human hepatocytes and ten thousand LX2 hepatic stellate cells were suspended in 10 µl of formulation collagen gel (collagen, hyaluronic acid, and fibronectin) or without fibronectin for the formation of liver organoids. The organoids were engineered in an identical method to cell line organoid formation described above, except 24-well plates (Corning) were employed. The wells were filled with 2 mL of HCM media (Triangle Research Labs), which was replenished after collecting media aliquots for further analysis on day 4, 7 and 10 of the experiment. The organoids were cultured for 14 days.

2.7. Cell Viability and Toxicity Assays for the Liver Organoids

Cell viability was determined by live/dead assays (Thermo Fisher) on day 7 and 14 using representative images and by quantification of biomarkers from media collected on days 4, 7, 10, and 14 (n=3): Alpha-Glutathione s-transferase (alpha-GST) is secreted by liver cells upon cell death. The secreted levels of alpha-GST by the organoids are quantified using a GST alpha assay kit (GS41, Oxford Biomedical Research; Rochester Hills, Mich.). Absorbance was read on a Spectramax M5 plate reader (Molecular Devices) at 450 nm for alpha-GST.

2.8. Functional Assays for the Liver Organoids

The secreted levels of albumin and urea of the liver organoids were quantified from media collected on days 4, 7, 10, and 14 (n=3) using a Human Albumin ELISA Kit (Abeam; Boston, Mass. ab108788) and Urea Assay Kit (Abcam, ab83362), respectively. Absorbance was read on a Spectramax M5 plate reader (Molecular Devices) at 450 nm for albumin and at 430 nm for urea.

2.9. Recalled Drug Studies

The hepatoxic drugs bromfenac sodium, troglitazone and tienilic acid, recalled by the FDA, were chosen for this study.[12, 32] All the compounds were purchased from Sigma-Aldrich. Drugs were dissolved in DMSO (dimethyl sulfoxide) for stock concentrations of 100 mM. Concentrations of 1 µM, 10 µm, 100 µM, and 1000 µM were used for bromfenac sodium and tienilic acid. Concentrations of 1 µm, 10 µM, and 100 µM were used for troglitazone. The drug study was conducted for 48 hours in a 24 well plate at 37° C. with 5% $CO_2$; each well in the plate containing one liver organoid in a 2 mL of media (control) or media with drug dissolved at the concentrations mentioned above (n≥6). The response of the liver organoids was assessed using Cell-Titer Glo Luminescent Cell Viability assay (Promega) prepared according to manufacturer's protocol. The results were quantified using the Veritas Microplate Luminometer setup according to manufacturer's instructions (Turner Bio Systems, Promega). Each condition was also subjected to live/dead staining (Thermo Fisher). Stained organoids were imaged using macro-confocal microscopy (Leica TCS LSI, Leica Microsystems).

2.10. Environmental Toxin Studies

The environmental toxins glyphosate, mercury chloride, and lead chloride were purchased from Sigma-Aldrich. Drugs were dissolved in $diH_2O$ for stock concentrations of 50 mM (glyphosate), 10 mM (mercury chloride), and 20 mM (lead chloride). Concentrations of 1 mM, 5 mM, 10 mM, and 20 mM were used for glyphosate. Concentrations of 10 µM, 20 µM, 50 µM, and 100 µM were used for mercury chloride. Concentrations of 1 mM, 2 mM, 5 mM, and 10 mM were used for lead chloride. The drug study was conducted for 48 hours (n=7) and liver organoids were assessed for viability with ATP assay and live/dead assay as described above.

2.11. Acetyl-Para-Aminophenol Toxicity Study

Acetyl-para-aminophenol (APAP) and N-Acetyl-L-cysteine (NAC), used to treat APAP overdose, were purchased from Sigma-Aldrich. Drugs were dissolved in HCM media to reach the desired concentrations. On day 7 in culture, liver organoids were treated with no drug, 1 mM APAP, 10 mM APAP, and simultaneously both with 10 mM APAP and 20 mM NAC, respectively (n=4). Viability of the liver organoids was assessed using live/dead assay on day 14; albumin and alpha GST production were quantified from media collected on days 4, 7, 10, and 14, as described above.

2.12. Statistical Analysis

All experiments were performed in triplicate or greater. Quantitative results are presented as mean±standard deviation. Values were compared using two-tailed Student's t test with two sample equal variance, and $p<0.05$ or less was considered statistically significant. GraphPad Prism software v7.0 (GraphPad Software, La Jolla, Calif.) was used for all analyses.

3. RESULTS

3.1. Feasibility Study

Figure 18:
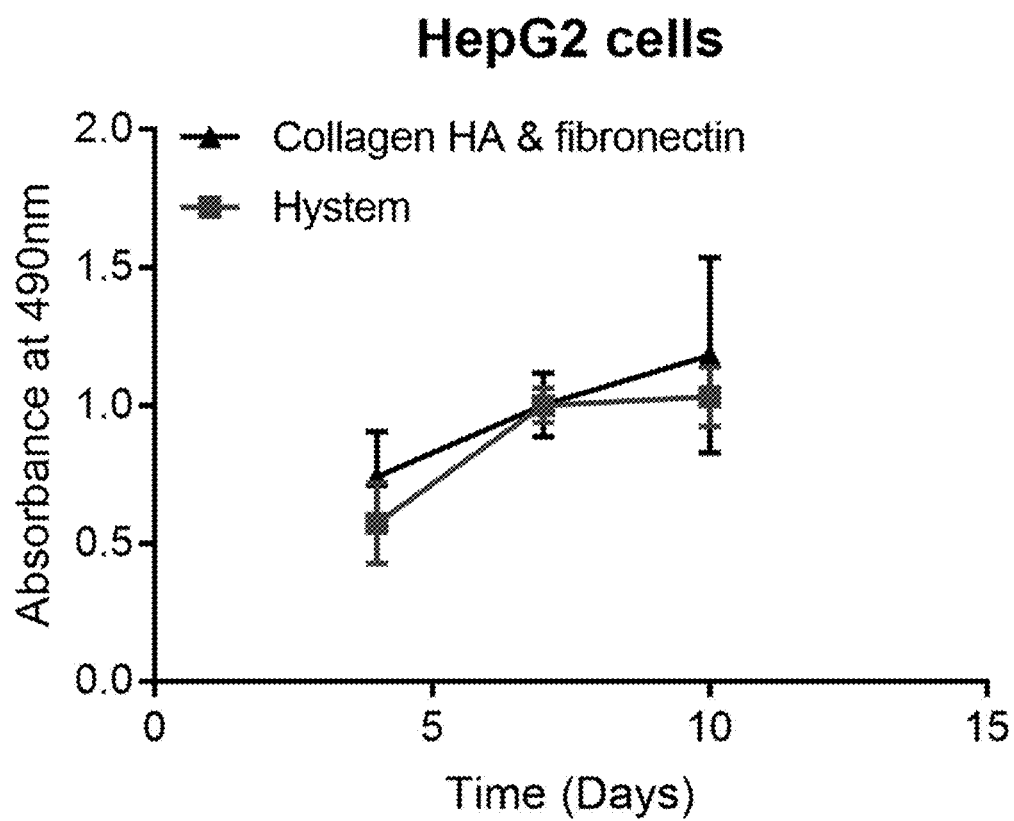
FIG. 18 shows biocompatibility of HepG2 cells in different gel formulations. Cell proliferation of HepG2 organoids in the gel formulations at days 4, 7, and 10 (n=3 per time point).

The aim of the present study was to develop a gel formulation that supports the viability and functionality of human liver organoids, and that can be employed in drug studies. We devised an initial feasibility study to screen two gel formulations with varying ECM composition for biocompatibility using different human cell lines. The hyaluronic acid based hydrogel was composed of hyaluronic acid, gelatin, and PEGDA at a ratio of 1:1:0.5. The collagen I based gel was comprised of methacrylated collagen and thiolated hyaluronic acid at a ratio of 1:3 with thiolated fibronectin incorporated as described above. Briefly, functionality of fibronectin incorporation was verified by demonstrating increased cell adhesion with incorporation of fibronectin in the hydrogel, compared to HA only hydrogels on which cells could not adhere. Live/dead analysis of U-87 MG and HCT 116 organoids over 10 days demonstrated comparable cell viability and proliferation between the two hydrogel formulations independent of the cell type used for making the organoids. The collagen and HA hydrogel with fibronectin was compared to a commercial hydrogel Hystem for demonstrating comparable viability and proliferation. We settled on collagen for the hepatic organoids because it is the most prominent component of the liver ECM—and most other tissues—in vivo. Similarly, while both gel compositions revealed excellent biocompatibility with only little cell death over time, the addition of fibronectin facilitated the proliferation of encapsulated HepG2 cells in the organoids (FIG. 18). This data suggests that the incorporation of fibronectin does not cause toxicity and the cells proliferate better. We decided to test fibronectin on hepatocytes.

3.2. Primary Liver Construct Study

Figure 19:
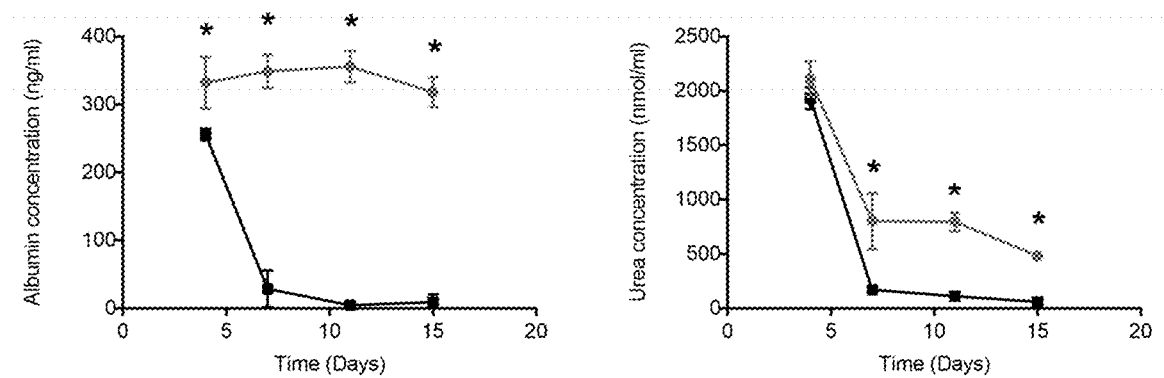
FIG. 19 illustrates liver organoids with and without fibronectin. Quantification of albumin (ng/ml) (left graph) and urea (nmol/ml) (right graph) from liver organoids in collagen gel formulation with and without fibronectin at days 4, 7, 11, and 15 (n=3 per time point). * represents statistical significance corresponding to P value less than 0.05.

Next, we engineered liver constructs, or organoids, comprised of primary human hepatocytes and stellate cells at a ratio of 4:1 using the collagen gel formulation (collagen and hyaluronic acid). To assess the contribution of fibronectin to liver organoid viability and function, the collagen gel formulations were prepared either with or without the additional ECM protein. Live/dead analysis of liver organoids demonstrated comparable cell viability yet greatly enhanced qualitative cell presence at 14 days when fibronectin was employed in the hydrogel formulation. Furthermore, as a proxy of tissue function, the production of albumin and urea in liver organoids containing fibronectin was significantly greater compared to organoids made without (FIG. 19). This data suggests that the addition of fibronectin to liver organoids improves both their viability and function. Therefore, next the response of liver organoids fabricated using the collagen, hyaluronic acid, and fibronectin formulation to various drugs and environmental toxins was investigated.

3.2.1. Drug Study

The drugs bromfenac sodium, troglitazone, and tienilic acid, recalled by the FDA for hepatotoxicity, were investigated[12, 32]. Live/dead analysis of liver organoids in presence of increasing concentrations of bromfenac sodium demonstrated increased cell death in a dose dependent manner, with near to complete cell death observed at 1000 μM. The half-maximal effective concentration ($EC_{50}$) of bromfenac sodium was 371.3 μM. Comparable live/dead staining patterns were noted with troglitazone and tienilic acid, and analysis of cell death revealed an $EC_{50}$ of 6.9 μM for troglitazone and 491.0 μM for and tienilic acid, respectively. This data suggests that bioengineered liver organoids exhibit dose-dependent sensitivity to drugs recalled by the FDA, thereby validating our model.

3.2.2. Environmental Toxin Study

Next, the response of liver organoids when exposed to various environmental toxins with known hepatotoxicity for 48 hours was investigated. Live/dead analysis of liver organoids in presence of increasing concentrations of glyphosate demonstrated increased cell death in a dose dependent manner, with near to complete cell death observed at 20 mM. The half-maximal effective concentration ($EC_{50}$) of glyphosate was 4.1 mM. Comparable live/dead staining patterns were noted with mercury chloride and lead chloride, and analysis of cell death revealed an $EC_{50}$ of 28.2 μM for mercury chloride and 0.97 mM for lead chloride, respectively. This data suggests that bioengineered liver organoids exhibit dose-dependent sensitivity to environmental toxins with known hepatotoxic effects.

3.2.3. Acetyl-Para-Aminophenol Study

Figure 20:
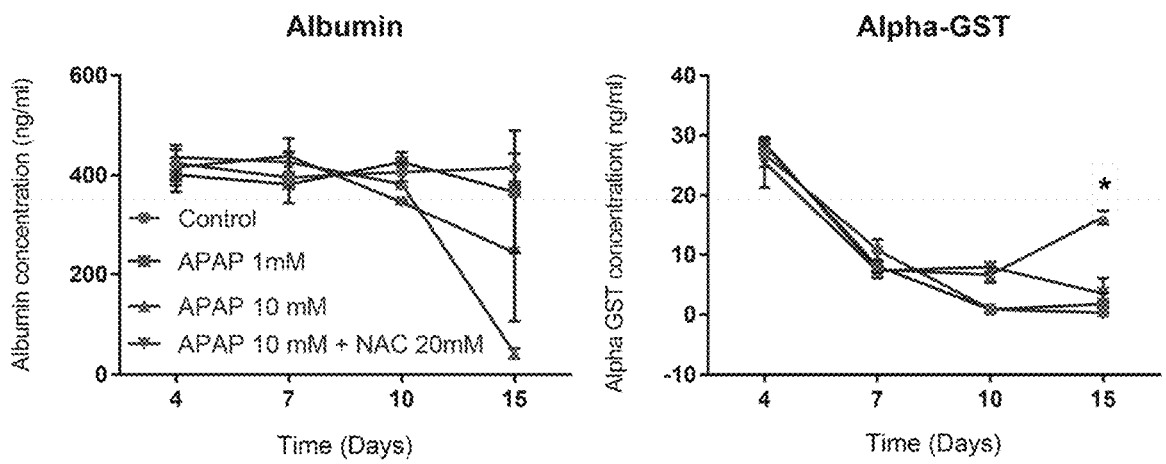
FIG. 20 illustrates APAP toxicity and NAC rescue with liver organoids. Albumin (left graph) and alpha-GST (right graph) of the liver organoids on day 4, 7, 10 and 15 is shown. Statistical significance: * p<0.05 between APAP 10 mM condition and all other conditions.

Acetyl-para-aminophenol (APAP) causes liver toxicity when taken in large doses. To treat APAP overdose, N-Acetyl-L-cysteine (NAC) is administered in the clinic. Therefore, it was investigated if liver organoids challenged with APAP could be rescued with NAC. Live/dead analysis of liver organoids in presence of increasing concentrations of APAP demonstrated increased cell death, with near to complete cell death observed at 10 mM. The addition of NAC to liver organoids exposed to high-concentration APAP markedly improved cell viability. Albumin production remained constant for the control and APAP 1 mM groups over time; a marked decrease was noted with APAP 10 mM vs. control by day 14, while co-incubation with NAC partially rescued albumin production in liver organoids at that time point (FIG. 20). Alpha-GST production exhibited an initial increase across all groups, indicating stress from organoid fabrication, but levels decreased consistently in the control and APAP 1 mM groups throughout the experimental period. At day 10, elevated alpha-GST levels were observed with APAP 10 mM and APAP 10 mM+NAC 20 mM groups vs. control. Importantly, alpha-GST production continued to increase with APAP 10 mM, whereas a noticeable decrease approaching control levels was noted with the addition of NAC by day 14 (FIG. 20), indicative of partial NAC-mediated functional rescue of liver organoids. This data suggests that bioengineered liver organoids exhibit APAP sensitivity and that organoid function can partially be rescued with NAC.

4. DISCUSSION

The aim of the present study was to develop a minimal component, defined liver tissue specific hydrogel formulation that can be used in the fabrication of liver organoids that improve upon current models in terms of functionality and tissue architecture. The two different gel formulations were tested for biocompatibility in three different common cell lines and the hydrogel formulation in which HepG2, a human liver hepatoma cell line—used widely as a hepatocyte surrogate in in vitro studies—had high biocompatibility and increased proliferation rates was chosen to be used in liver organoids. The chosen formulation was further modified with fibronectin and the liver organoids comprised of primary human hepatocytes and stellate cells were assessed for functionality and viability. It was observed that the addition of fibronectin significantly improved both viability and functionality of the hepatocytes as evidenced by live/dead staining and the secretion of albumin and urea in these liver organoids when compared to organoids without fibronectin. It was noted that the urea production had decreased in both the organoids with and without fibronectin from day 4 to day 7, but urea production was maintained at higher levels in the liver organoids with fibronectin. This formulation was chosen for the subsequent drug studies conducted with liver constructs. The liver constructs were designed to provide a reliable model that can be used in drug testing thereby reducing the need for or supplementing current animal testing and two-dimensional cell cultures; while these traditional model systems have been the workhorses of biomedical research, they both suffer from innate inadequacies. A dose dependent toxicity was observed when the liver constructs were exposed to FDA recalled hepatoxic drugs and environmental toxins with known liver toxicity[12, 33-34]. In conclusion the clinical relevance of the liver organoids was demonstrated through the APAP drug study in which the liver organoids exhibited toxicity when exposed to acetaminophen and then the liver organoids' function could be partially restored with NAC, a drug commonly used in the clinic to treat acetaminophen induced liver toxicity.[35]

Prior studies on the effect of fibronectin on hepatocytes' functionality have concluded that fibronectin is essential to albumin production and also play an important role in hepatocyte attachment to collagen.[36] The matrix was biofunctionalized with this critical protein and it has been shown that it creates a superior microenvironment for promoting hepatic organoid viability and function. Human hepatocyte cultured in vitro in 2D are known to lose their morphology and liver specific function and hence a great deal of resources have gone in to constructing viable 3D matrices for these hepatocytes so that they can maintain their function long term in vitro.[37] However, many such efforts, including previous efforts in our laboratory, have relied on inadequately defined materials such as Matrigel or tissue-derived ECM supplements,[11, 16, 19, 30] which have little chance for advancing to applications requiring strict regulatory approval. In this study, we demonstrate the use of a well-defined hydrogel system to support primary hepatocyte-based constructs. It can be clearly appreciated that the hepatocytes placed in the hydrogel formulation with fibronectin seem to retain their liver functions as evidenced by their stable albumin production and urea production for a period of 14 days.

The liver organoids fabricated in this study could be used as an efficient and inexpensive drug testing platform that can help identify compounds with hepatotoxicity in early stage toxicity and safety studies. To demonstrate such an application, liver organoids were exposed to known hepatotoxic drugs; bromfenac sodium, troglitazone, and tienilic acid and environmental toxins with established hepatotoxicity; glyphosate, lead and mercury.[12, 33, 41-42] Tienilic acid was introduced an antihypertensive which had to be pulled from the market after the patients treated with this drug developed acute or chronic hepatitis.[43] Bromfenac sodium is a non-steroidal anti-inflammatory drug which was withdrawn due to fulminant hepatic necrosis.[44] Troglitazone is a thiazolidine, an antidiabetic that had to be recalled because of idiosyncratic hepatic toxicity.[45] Dose dependent hepatotoxicity in the liver organoids was observed with results comparable to those observed clinically.

To demonstrate additional clinical relevance and translational potential, organoids were exposed to APAP or to a mixture of APAP and N-Acetyl cysteine, which is used clinically to rescue hepatocytes from APAP overdose.[35, 46] In this scenario, APAP is metabolized by liver, resulting in a toxic byproduct, which is usually removed when conjugated with glutathione. However, at high doses of APAP, large amounts of this byproduct is generated and N-acetylcysteine can stimulate production of glutathione, thus serving as an effective antidote.[35] In the organoids liver toxicity was observed when exposed to APAP. Upon addition of N-acetyl-cysteine some rescue of liver viability and function was noticeable, albeit not complete rescue. These results, together with those described above, appear to indicate that the hydrogel system employed herein can support primary liver organoids with a variety of physiologically relevant drug and toxin responses.

The studies demonstrated here show that the hydrogel system employed herein can be used successfully to support primary human hepatocyte liver constructs with measurable function. Moreover, the fabricated liver organoids could be used in drug testing and toxicology studies and may be used to supplement animal testing and 2D cell culture testing. The system is robust, keeping the hepatocytes viable and functionally intact by providing them with the 3D microenvironment cues in the form of a hyaluronic acid and collagen matrix supplemented with fibronectin. Furthermore, given the use of patient-derived hepatocytes in this system, also suggests that the organoids could be customized with patient derived cells for personalized precision medicine applications or population-based drug development.

REFERENCES

1. Scannell, J. W.; Blanckley, A.; Boldon, H.; Warrington, B., Diagnosing the decline in pharmaceutical R&D efficiency. Nature reviews. Drug discovery 2012, 11 (3), 191-200.

2. Leoni, A. K.-S.; James, P. F.; Ferdinand, H.; Reinhard, E., The Use of 3-D Cultures for High-Throughput Screening: The Multicellular Spheroid Model. Journal of Biomolecular Screening 2004, 9 (4), 273-285.

3. Soldatow, V. Y.; LeCluyse, E. L.; Griffith, L. G.; Rusyn, I., In vitro models for liver toxicity testing. Toxicology research 2013, 2 (1), 23-39.

4. Langer, R.; Vacanti, J. P., Tissue engineering. Science (New York, N.Y.) 1993, 260 (5110), 920-6.

5. Vanderburgh, J.; Sterling, J. A.; Guelcher, S. A., 3D Printing of Tissue Engineered Constructs for In Vitro Modeling of Disease Progression and Drug Screening. Annals of biomedical engineering 2017, 45 (1), 164-179.

6. Edmondson, R.; Broglie, J. J.; Adcock, A. F.; Yang, L., Three-Dimensional Cell Culture Systems and Their Applications in Drug Discovery and Cell-Based Biosensors. Assay and Drug Development Technologies 2014, 12 (4), 207-218.

7. Simian, M.; Bissell, M. J., Organoids: A historical perspective of thinking in three dimensions. The Journal of cell biology 2016.

8. Nantasanti, S.; de Bruin, A.; Rothuizen, J.; Penning, L. C.; Schotanus, B. A., Concise Review: Organoids Are a Powerful Tool for the Study of Liver Disease and Personalized Treatment Design in Humans and Animals. Stem Cells Translational Medicine 2016, 5 (3), 325-330.

9. Vyas, D.; Baptista, P. M.; Brovold, M.; Moran, E.; Gaston, B.; Booth, C.; Samuel, M.; Atala, A.; Soker, S., Self-assembled liver organoids recapitulate hepatobiliary organogenesis in vitro. Hepatology (Baltimore, Md.) 2017.

10. Devarasetty, M.; Wang, E.; Soker, S.; Skardal, A., Mesenchymal stem cells support growth and organization of host-liver colorectal-tumor organoids and possibly resistance to chemotherapy. Biofabrication 2017, 9 (2), 021002.

11. Skardal, A.; Smith, L.; Bharadwaj, S.; Atala, A.; Soker, S.; Zhang, Y., Tissue specific synthetic ECM hydrogels for 3-D in vitro maintenance of hepatocyte function. Biomaterials 2012, 33 (18), 4565-75.

12. Goldkind, L.; Laine, L., A systematic review of NSAIDs withdrawn from the market due to hepatotoxicity: lessons learned from the bromfenac experience. Pharmacoepidemiology and drug safety 2006, 15 (4), 213-20.

13. Meng, Q., Three-dimensional culture of hepatocytes for prediction of drug-induced hepatotoxicity. Expert opinion on drug metabolism & toxicology 2010, 6 (6), 733-46.

14. Hynds, R. E.; Giangreco, A., The relevance of human stem cell-derived organoid models for epithelial translational medicine. Stem cells (Dayton, Ohio) 2013, 31 (3), 417-422.

15. Sgodda, M.; Dai, Z.; Zweigerdt, R.; Sharma, A. D.; Ott, M.; Cantz, T., A Scalable Approach for the Generation of Human Pluripotent Stem Cell-Derived Hepatic Organoids with Sensitive Hepatotoxicity Features. Stem cells and development 2017, 26 (20), 1490-1504.

16. Skardal, A.; Murphy, S. V.; Devarasetty, M.; Mead, I.; Kang, H. W.; Seol, Y. J.; Shrike Zhang, Y.; Shin, S. R.; Zhao, L.; Aleman, J.; Hall, A. R.; Shupe, T. D.; Kleensang, A.; Dokmeci, M. R.; Jin Lee, S.; Jackson, J. D.; Yoo, J. J.; Hartung, T.; Khademhosseini, A.; Soker, S.; Bishop, C. E.; Atala, A., Multi-tissue interactions in an integrated three-tissue organ-on-a-chip platform. Sci Rep 2017, 7 (1), 8837.

17. Au, S. H.; Chamberlain, M. D.; Mahesh, S.; Sefton, M. V.; Wheeler, A. R., Hepatic organoids for microfluidic drug screening. Lab on a chip 2014, 14 (17), 3290-9.

18. Skardal, A.; Devarasetty, M.; Forsythe, S.; Atala, A.; Soker, S., A reductionist metastasis-on-a-chip platform for in vitro tumor progression modeling and drug screening. Biotechnol Bioeng 2016, 113 (9), 2020-32.

19. Skardal, A.; Devarasetty, M.; Rodman, C.; Atala, A.; Soker, S., Liver-Tumor Hybrid Organoids for Modeling Tumor Growth and Drug Response In Vitro. Ann Biomed Eng 2015, 43 (10), 2361-73.

20. Gerets, H. H. J.; Tilmant, K.; Gerin, B.; Chanteux, H.; Depelchin, B. O.; Dhalluin, S.; Atienzar, F. A., Characterization of primary human hepatocytes, HepG2 cells, and HepaRG cells at the mRNA level and CYP activity in response to inducers and their predictivity for the detection of human hepatotoxins Cell Biology and Toxicology 2012, 28 (2), 69-87.

21. Leite, S. B.; Roosens, T.; El Taghdouini, A.; Mannaerts, I.; Smout, A. J.; Najimi, M.; Sokal, E.; Noor, F.; Chesne, C.; van Grunsven, L. A., Novel human hepatic organoid model enables testing of drug-induced liver fibrosis in vitro. Biomaterials 2016, 78, 1-10.

22. Castell, J. V.; Jover, R.; Martinez-Jimenez, C. P.; Gomez-Lechon, M. J., Hepatocyte cell lines: their use, scope and limitations in drug metabolism studies. Expert opinion on drug metabolism & toxicology 2006, 2 (2), 183-212.

23. Martinez-Hernandez, A.; Amenta, P. S., The hepatic extracellular matrix. II. Ontogenesis, regeneration and cirrhosis. Virchows Archiv. A, Pathological anatomy and histopathology 1993, 423 (2), 77-84.

24. Kawelke, N.; Vasel, M.; Sens, C.; Au, A.; Dooley, S.; Nakchbandi, I. A., Fibronectin protects from excessive liver fibrosis by modulating the availability of and responsiveness of stellate cells to active TGF-beta. PloS one 2011, 6 (11), e28181.

25. Skardal, A.; Devarasetty, M.; Soker, S.; Hall, A. R., In situ patterned micro 3D liver constructs for parallel toxicology testing in a fluidic device. Biofabrication 2015, 7 (3), 031001.

26. Skardal, A.; Murphy, S. V.; Crowell, K.; Mack, D.; Atala, A.; Soker, S., A tunable hydrogel system for long-term release of cell-secreted cytokines and bioprinted in situ wound cell delivery. J Biomed Mater Res B Appl Biomater 2017, 105 (7), 1986-2000.

27. Sivakumar, H.; Strowd, R.; Skardal, A., Exploration of dynamic elastic modulus changes on glioblastoma cell populations with aberrant EGFR expression as a potential therapeutic intervention using a tunable hyaluronic acid hydrogel platform. Gels 2017, 3 (3), 28.

28. Murphy, S. V.; Skardal, A.; Song, L.; Sutton, K.; Haug, R.; Mack, D. L.; Jackson, J.; Soker, S.; Atala, A., Solubilized Amnion Membrane Hyaluronic Acid Hydrogel Accelerates Full-Thickness Wound Healing. Stem Cells Transl Med 2017, 6 (11), 2020-2032.

29. Skardal, A.; Devarasetty, M.; Kang, H. W.; Mead, I.; Bishop, C.; Shupe, T.; Lee, S. J.; Jackson, J.; Yoo, J.; Soker, S.; Atala, A., A hydrogel bioink toolkit for mimicking native tissue biochemical and mechanical properties in bioprinted tissue constructs. Acta Biomater 2015, 25, 24-34.

30. Skardal, A.; Devarasetty, M.; Kang, H. W.; Seol, Y. J.; Forsythe, S. D.; Bishop, C.; Shupe, T.; Soker, S.; Atala, A., Bioprinting Cellularized Constructs Using a Tissue-specific Hydrogel Bioink. J Vis Exp 2016, (110).

31. Skardal, A.; Devarasetty, M.; Soker, S.; Hall, A. R., In situ patterned micro 3D liver constructs for parallel toxicology testing in a fluidic device. Biofabrication 2015, 7 (3), 031001-031001.

32. Shaw, P. J.; Ganey, P. E.; Roth, R. A., Idiosyncratic Drug-Induced Liver Injury and the Role of Inflammatory Stress with an Emphasis on an Animal Model of Trovafloxacin Hepatotoxicity. Toxicological Sciences 2010, 118 (1), 7-18.

33. Mudipalli, A., Lead hepatotoxicity & potential health effects. The Indian journal of medical research 2007, 126 (6), 518-27.

34. Forsythe, S. D.; Devarasetty, M.; Shupe, T.; Bishop, C.; Atala, A.; Soker, S.; Skardal, A., Environmental toxin screening using human-derived 3D bioengineered liver and cardiac organoids. Front Public Health 2018, 6 (103), 1-10.

35. Ben-Shachar, R.; Chen, Y.; Luo, S.; Hartman, C.; Reed, M.; Nijhout, H. F., The biochemistry of acetaminophen hepatotoxicity and rescue: a mathematical model. Theoretical Biology & Medical Modelling 2012, 9, 55-55.

36. Maffei, G.; Magliaro, C.; Giusti, S.; Ramachandran, S. D.; Heinz, S.; Braspenning, J.; Ahluwalia, A., On the adhesion-cohesion balance and oxygen consumption characteristics of liver organoids. PloS one 2017, 12 (3), e0173206.

37. Zhang, J.; Zhao, X.; Liang, L.; Li, J.; Demirci, U.; Wang, S., A Decade of Progress in Liver Regenerative Medicine. Biomaterials.

38. Hughes, J. P.; Rees, S.; Kalindjian, S. B.; Philpott, K. L., Principles of early drug discovery. British Journal of Pharmacology 2011, 162 (6), 1239-1249.

39. Lee, W. M., Drug-induced acute liver failure. Clinics in liver disease 2013, 17 (4), 575-86, viii.

40. Kullak-Ublick, G. A.; Andrade, R. J.; Merz, M.; End, P.; Benesic, A.; Gerbes, A. L.; Aithal, G. P., Drug-induced liver injury: recent advances in diagnosis and risk assessment. Gut 2017, 66 (6), 1154-1164.

41. Zhang, H.; Tan, X.; Yang, D.; Lu, J.; Liu, B.; Baiyun, R.; Zhang, Z., Dietary luteolin attenuates chronic liver injury induced by mercuric chloride via the Nrf2/NF-kappaB/P53 signaling pathway in rats. Oncotarget 2017, 8 (25), 40982-40993.

42. Jasper, R.; Locatelli, G. O.; Pilati, C.; Locatelli, C., Evaluation of biochemical, hematological and oxidative parameters in mice exposed to the herbicide glyphosate-Roundup(®). Interdisciplinary Toxicology 2012, 5 (3), 133-140.

43. Poupon, R.; Homberg, J. C.; Abuaf, N.; Petit, J.; Bodin, F.; Darnis, F., [Tienilic acid-induced hepatitis associated with liver/kidney microsomal antibody (author's transl)]. La Nouvelle presse medicale 1980, 9 (27), 1881-4.

44. Mayoral, W.; Lewis, J. H.; Zimmerman, H., Drug-induced liver disease. Current opinion in gastroenterology 1999, 15 (3), 208-16.

45. Kim, D. E.; Jang, M. J.; Kim, Y. R.; Lee, J. Y.; Cho, E. B.; Kim, E.; Kim, Y.; Kim, M. Y.; Jeong, W. I.; Kim, S.; Han, Y. M.; Lee, S. H., Prediction of drug-induced immune-mediated hepatotoxicity using hepatocyte-like cells derived from human embryonic stem cells. Toxicology 2017, 387, 1-9.

46. Simon, J. B., Acetaminophen Liver Injury. Canadian Family Physician 1985, 31, 2155-2158.

Example 10

Elastic modulus testing was performed on two different compositions on a TA Instruments Discovery HR-2 rheometer. Strain was applied at 10% for 10 seconds, ramped up to 100% at 10-20 seconds, and returned to 10%. Elastic modulus G' and loss modulus G" were calculated and recorded.

Each of the two compositions included: 25% Heprasil® solution including Heprasil® at 10 mg/mL (1% w/v) and photoinitiator (PI) at 0.05% w/v and 75% methacrylated collagen solution including 6.75% mL neutralization solution, 45.5% mL methacrylated collagen I (6 mg/mL), and 22.75% mL acetic acid. The two compositions each included one additional component.

Figure 21:
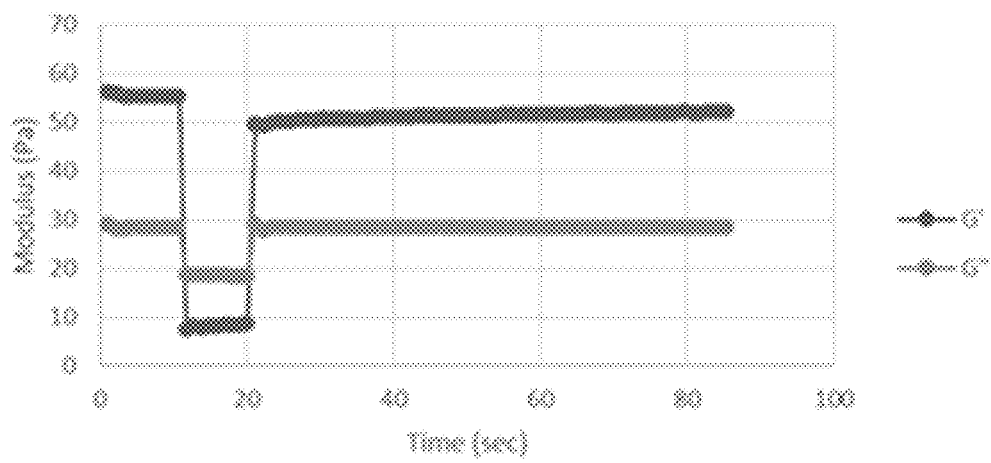
FIG. 21 is a graph showing elastic modulus for a composition according to some embodiments of the present invention.

The first composition additionally included a catecholamine in an amount of 5 mg/mL. The results from the elastic modulus testing on the second composition are shown in FIG. 21.

Figure 22:
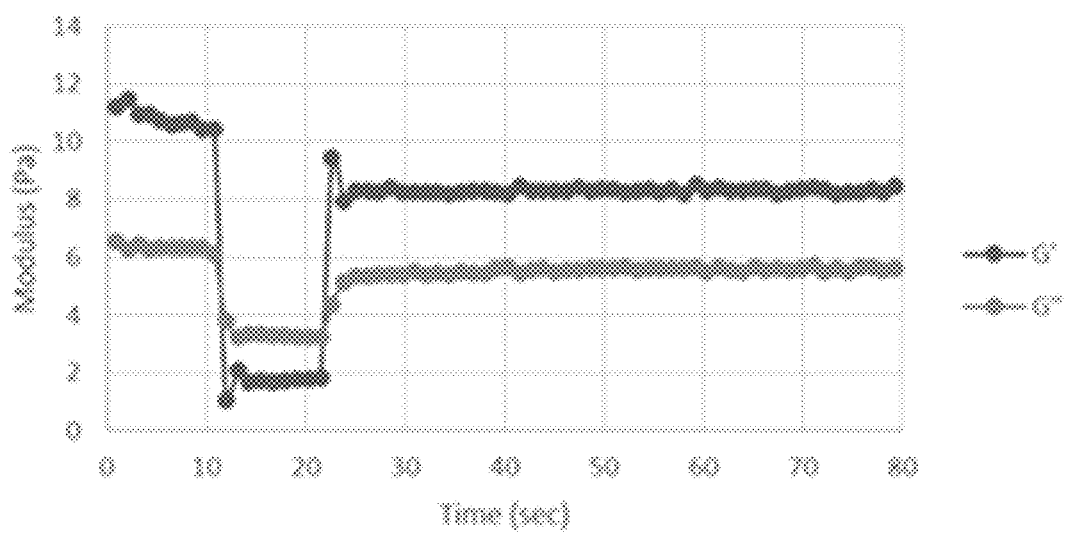
FIG. 22 is a graph showing elastic modulus for another composition according to some embodiments of the present invention.

The second composition additionally included a catecholamine in an amount of 10 mg/mL. The results from the elastic modulus testing on the third composition are shown in FIG. 22.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A composition comprising:
   thiolated hyaluronic acid;
   methacrylated collagen; and
   water.

2. The composition of claim 1, wherein the thiolated hyaluronic acid is present in the composition in an amount of about 0.1% to about 2% w/v of the composition.

3. The composition of claim 1, wherein the methacrylated collagen is present in the composition in an amount of about 0.5 mg/mL of the composition to about 10 mg/mL of the composition.

4. The composition of claim 1, wherein the composition has a ratio of the thiolated hyaluronic acid to the methacrylated collagen in a range from 1:0.5 to 1:10 (thiolated hyaluronic acid:methacrylated collagen) by volume.

5. The composition of claim 1, wherein the composition has a pH of about 6.5 or 7 to about 7.5 or 8.

6. The composition of claim 1, wherein the composition is extrudable with an applied mechanical stress in a range from about 1 kPa to about 80 kPa.

7. The composition of claim 1, wherein the composition comprises a greater number of methacrylate groups as compared to thiol groups.

8. The composition of claim 1, further comprising one or more small molecule(s) comprising a functional group that provides hydrogen bonding.

9. The composition of claim 8, wherein the one or more small molecule(s) comprises a catechol amine, a catechol containing an alkynyl imine, a catechol containing an alkynyl amine, a catechol containing an alkenyl imine, a catechol containing an alkenyl amine, a catechol containing an acrylate imine, a catechol containing an acrylate amine, a catechol containing a methacrylate imine, benzylamine, and/or a catechol containing a methacrylate amine.

10. The composition of claim 1, further comprising a protein and/or proteoglycan.

11. The composition of claim 1, further comprising fibronectin, heparin, and/or laminin.

12. The composition of claim 1, further comprising one or more live cell(s).

13. The composition of claim 1, wherein the composition has an elastic modulus from about 10 or 25 Pa to about 500 or 1,000 Pa.

14. The composition of claim 1, further comprising one or more growth factor(s).

15. The composition of claim 1, further comprising a thermal initiator or photoinitiator.

16. The composition of claim 1, wherein the composition is thixotropic.

17. The composition of claim 6, wherein the composition has an elastic modulus after extrusion that varies by less than about 20% compared to an elastic modulus of the composition prior to extrusion and/or the composition during extrusion has an elastic modulus G' that is less than a loss modulus G".

18. The composition of claim 6, wherein the composition has an elastic modulus G' and a loss modulus G" that are within ±20% of each other.

19. A method of making an organoid, comprising:
   providing a composition of claim 1 having a pH of about 6.5 or 7 to about 7.5 or 8;
   adding one or more live cell(s) to the composition to provide a hyaluronic acid-collagen hydrogel including the cells; and
   forming an organoid from the hyaluronic acid-collagen hydrogel.

20. A method of increasing the viability and/or functional activity of an organoid, the method comprising:
   providing a composition of claim 1 comprising live cells to provide a hyaluronic acid-collagen hydrogel including cells;
   forming an organoid from the hyaluronic acid-collagen hydrogel; and
   culturing the cells in the organoid, thereby increasing the viability and/or functional activity of an organoid compared to an organoid in the absence of the hyaluronic acid-collagen hydrogel.

* * * * *

UNITED STATES PATENT AND TRADEMARK OFFICE
CERTIFICATE OF CORRECTION

Page 1 of 2

PATENT NO. : 11,629,329 B2
APPLICATION NO. : 16/156535
DATED : April 18, 2023
INVENTOR(S) : Aleksander Skardal It is certified that error appears in the above-identified patent and that said Letters Patent is hereby corrected as shown below:

On the Title Page

(56) References Cited, OTHER PUBLICATIONS, Page 4, Column 1, Line 60: Please correct "Sandhi et al." to read --Gandhi et al.--

In the Specification

Column 12, Lines 25-35, Formula I and Formula II: Please delete Formula I and Formula II and replace with the following:

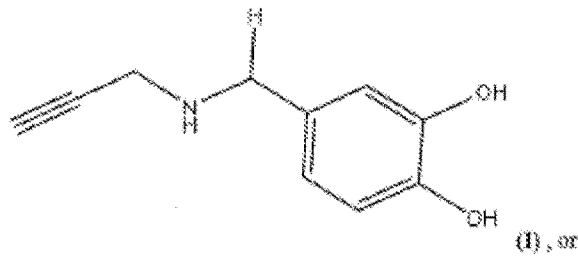

(I), or

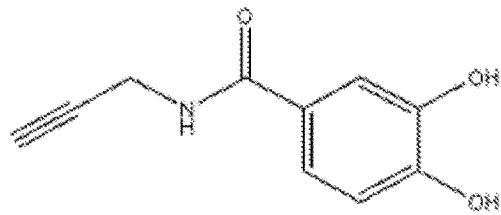

(II).

Signed and Sealed this
Twenty-fifth Day of July, 2023

Katherine Kelly Vidal
*Director of the United States Patent and Trademark Office*

CERTIFICATE OF CORRECTION (continued)
U.S. Pat. No. 11,629,329 B2

Column 23, Line 23: Please correct "100.00 cells" to read --100,00 cells--

Column 44, Lines 44-45: Please correct "toxicity $^{12,}$ $_{33\text{-}34}$." to read --toxicity $^{12, 33\text{-}34}$.--

Column 48, Line 12: Please correct "36. Maffei, G." to read --36. Mattei, G.--